US008637310B2

(12) United States Patent
McBride et al.

(10) Patent No.: US 8,637,310 B2
(45) Date of Patent: Jan. 28, 2014

(54) USE OF A ROCK INHIBITOR TO SUSTAIN PRIMARY HUMAN KERATINOCYTES IN A PROLIFERATIVE STATE

(75) Inventors: Alison McBride, Bethesda, MD (US); Sandra Chapman, Washington, DC (US); Jonathan Vogel, Bethesda, MD (US); Atsushi Terunuma, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 159 days.

(21) Appl. No.: 13/132,391

(22) PCT Filed: Dec. 4, 2009

(86) PCT No.: PCT/US2009/066844
§ 371 (c)(1), (2), (4) Date: Jun. 2, 2011

(87) PCT Pub. No.: WO2010/065907
PCT Pub. Date: Jun. 10, 2010

(65) Prior Publication Data

US 2011/0243903 A1 Oct. 6, 2011

Related U.S. Application Data

(60) Provisional application No. 61/120,272, filed on Dec. 5, 2008.

(51) Int. Cl.
*C12N 5/00* (2006.01)

(52) U.S. Cl.
USPC ........... 435/377; 435/375; 435/373; 435/325; 424/93.7

(58) Field of Classification Search
None
See application file for complete search history.

(56) References Cited

U.S. PATENT DOCUMENTS

2004/0214323 A1 10/2004 Simon et al.
2004/0265787 A9 12/2004 Allen-Hoffmann et al.

FOREIGN PATENT DOCUMENTS

WO WO 97/23602 7/1997

OTHER PUBLICATIONS

Ozturk M et al. 2009. Senescence and immortality in hepatocellular carcinoma. Cancer Lett 286: 103-113.*

Shawi M et al. 2008. Telomerase, senescence, and ageing. Mech Ageing Devel 129: 3-10.*

Kang MK et al. 2003. Senescence-associated genes in normal human oral keratinocytes. Exp Cell Res 287: 272-281.*

Croft DR et al. 2006. The Rho GTPase Effector ROCK Regulates Cyclin A, Cyclin D1, and p27Kip1 Levels by Distinct Mechanisms. Mol Cell Biol 26: 4612-4627.*

Chapman et al, "Human Keratinocytes are Efficiently Immortalized by a Rho Kinase Inhibitor," *J. Clin. Invest.*, vol. 120(7):2619-2626, 2010.

McMullan et al., "Keratinocyte Differentiation is Regulated by the Rho and ROCK Signaling Pathway," *Curr. Bio.*, vol. 13:2185-2189, 2003.

Narumiya et al., "Use and Properties of ROCK-Specific Inhibitor Y-27632," *Meth. Enzym.*, vol. 325:273-284, 2000.

Watanabe et al., "A ROCK Inhibitor Permits Survival of Dissociated Human Embryonic Stem Cells," *Nat. Biotechnol.*, vol. 25(6):681-686, 2007.

Woodworth et al., "Immortalization of Human Foreskin Keratinocytes by Various Human Papillomavirus DNAs Corresponds to their Association with Cervical Carcinoma," *J. Virol.*, vol. 63(1):159-164, 1989.

* cited by examiner

*Primary Examiner* — Lora E Barnhart Driscoll
(74) *Attorney, Agent, or Firm* — Leydig, Voit & Mayer

(57) ABSTRACT

Disclosed herein is the finding that treatment with a ROCK inhibitor increases proliferation and induces immortalization of primary keratinocytes. Accordingly, provided is a method of immortalizing primary keratinocytes by exposure to a ROCK inhibitor. Also provided are immortalized primary keratinocytes produced by the described method, as well as organotypic tissue equivalents and cell cultures comprising the immortalized primary keratinocytes. Furthermore, ROCK inhibitor-treated cells show a greatly increased ability to support viral DNA replication of both "low risk" and "high risk" HPV genomes, indicating that ROCK inhibitors will be useful for studying the life cycles of a wide range of HPVs.

17 Claims, 13 Drawing Sheets

FIG. 13A
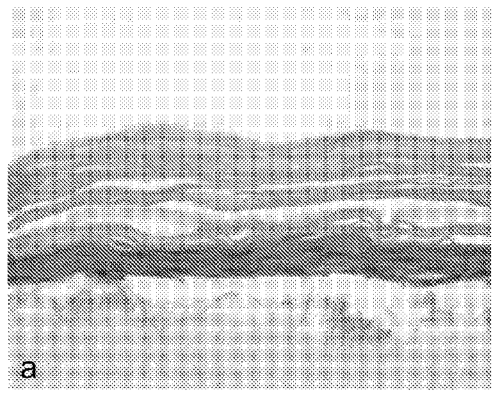
FIG. 13B
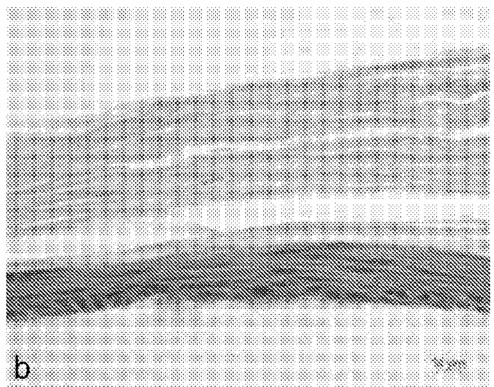
FIG. 13C
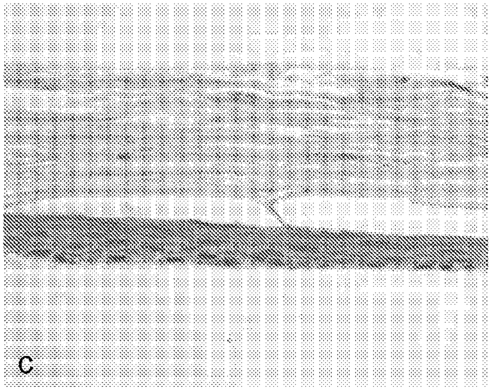
FIG. 13D
d

USE OF A ROCK INHIBITOR TO SUSTAIN PRIMARY HUMAN KERATINOCYTES IN A PROLIFERATIVE STATE

CROSS REFERENCE TO RELATED APPLICATIONS

This application is the U.S. National Stage of International Application No. PCT/US2009/066844, filed Dec. 4, 2009, which was published in English under PCT Article 21(2), which claims the benefit of U.S. Provisional Application No. 61/120,272, filed Dec. 5, 2008, which is herein incorporated by reference in its entirety.

FIELD

This disclosure relates to the use of Rho-associated kinase (ROCK) inhibitors to increase the proliferative capacity and induce immortalization of primary keratinocytes.

BACKGROUND

Somatic cells have a limited lifespan and gradually slow in growth and stop dividing, a process known as cellular senescence. This process is thought to limit the vulnerability of aging cells to disease. Human keratinocytes are invaluable for the study of skin biology and the pathogenesis of skin-related diseases, but their short lifespan in culture is a limitation.

The life cycle of human papillomavirus (HPV) is best studied in primary human keratinocytes, the natural host cells of HPV. Papillomaviruses infect the mitotically active cells of the basal layer of the epithelium, but viral progeny are only produced when these infected precursor cells differentiate. Papillomavirus infections are persistent and the viral genome is maintained in the continuously dividing basal cells for long time periods. The HPV genome can be transfected into isolated keratinocytes where it becomes established as an extrachromosomally replicating element. These infected cells can be induced to differentiate and stratify and support the productive cycle of HPVs (Frattini et al., *Proc. Natl. Acad. Sci, USA* 93:3062-3067, 1996; Meyers et al., *Science* 257:971-973, 1992).

A subset of about 15 papillomaviruses from the alpha genera is associated with cancer, primarily of the uterine cervix (Smith et al., *Int. J. Cancer* 121:621-632, 2007). Almost 100% of cervical carcinomas contain a "high-risk" HPV. These "high-risk" viruses are also associated with a subset of head and neck cancers (Gillison and Shah, *Curr. Opin. Oncol.* 13:183-188, 2001). These cancer-associated HPVs are also able to immortalize primary human keratinocytes in culture (Hawley-Nelson et al., *EMBO J.* 8:3905-3910, 1989; Munger et al., *J. Virol.* 63:4417-4421, 1989). Under the appropriate culture conditions, the viral genome is maintained as an extrachromosomal element and the functions of the viral E6 and E7 oncoproteins provide a selective growth advantage for these cells (Goodwin et al., *Proc. Natl. Acad. Sci. USA* 97: 10978-10983, 2000). These cells can be further cultured as an organotypic raft where progeny virus can be produced (Frattini et al., *Proc. Natl. Acad. Sci, USA* 93:3062-3067, 1996).

Much less is known about the "low-risk" HPVs that are not associated with malignant carcinomas. The genomes of these viruses can be introduced into primary cells, but the E6 and E7 proteins do not provide a growth advantage to the cells which will often senesce before extensive studies can be carried out or before they can be cultured in an organotypic raft. These "low-risk" viruses are, however, the causative agents of a wide range of benign, proliferative lesions that can cause intractable disease. These viruses can be studied in immortalized keratinocyte cell lines, but these lines have been shown to have genetic abnormalities that could interfere with functional analyses of the virus (Lehman et al., *Carcinogenesis* 14:833-839, 1993). Thus, a need exists to increase the proliferative capacity of human primary keratinocytes and to develop an efficient means to induce immortalization of these cells. Such methods are desirable not only for studies of HPV replication, but for a variety of therapeutic purposes.

SUMMARY

It is disclosed herein that treatment of primary keratinocytes with a ROCK inhibitor increases proliferation and leads to immortalization of these cells. The immortalized keratinocytes have a normal karyotype, an intact DNA damage response and are able to differentiate into stratified epithelium. In addition, primary keratinocytes treated with a ROCK inhibitor support viral replication of both low-risk and high risk human papillomaviruses (HPVs).

Thus, provided herein is a method of immortalizing primary keratinocytes by culturing the primary keratinocytes in the presence of an effective amount of a ROCK inhibitor for a period of time sufficient to allow immortalization of the primary keratinocytes. In some embodiments, the method further includes continuing to culture the immortalized keratinocytes in the absence of the ROCK inhibitor. The immortalized keratinocytes retain the capacity to differentiate when cultured in the absence of the ROCK inhibitor. Isolated immortalized primary keratinocytes produced by the disclosed methods, organotypic tissue equivalents comprising the immortalized primary keratinocytes, and cell cultures comprising the immortalized primary keratinocytes, are also provided herein.

Also provided herein is a method of increasing proliferation of primary keratinocytes by culturing the primary keratinocytes in the presence of an effective amount of a ROCK inhibitor. In some embodiments, the method comprises culturing the primary keratinocytes in the presence of the ROCK inhibitor for a period of time sufficient to allow immortalization of the primary keratinocytes.

Further provided are organotypic tissue equivalents comprised of immortalized primary keratinocytes. The primary keratinocytes are immortalized by culturing the primary keratinocytes in the presence of an effective amount of a ROCK inhibitor for a period of time sufficient to allow immortalization of the primary keratinocytes. In some embodiments, the immortalized keratinocytes are further cultured in the absence of the ROCK inhibitor, allowing the keratinocytes to differentiate and form the organotypic tissue equivalent.

Also provided are compositions including an isolated immortalized primary keratinocyte. The primary keratinocyte is immortalized by culturing in the presence of an effective amount of a ROCK inhibitor for a period of time sufficient to allow immortalization of the primary keratinocyte.

A method of promoting HPV replication in primary keratinocytes is also provided. The method includes infecting the primary keratinocytes with HPV or transfecting the primary keratinocytes with an HPV genome, and culturing the primary keratinocytes in the presence of an effective amount of a ROCK inhibitor.

Further provided is a method of preparing an organotypic tissue equivalent including obtaining isolated primary keratinocytes, culturing the primary keratinocytes in the presence of an effective amount of a ROCK inhibitor for a period of time sufficient to allow for proliferation of the primary keratinocytes, and continuing to culture the primary keratinocytes in the absence of the ROCK inhibitor, thereby allowing the primary keratinocytes to differentiate and form an organotypic tissue equivalent. A method of treating a wound or skin disease in a subject by treating the subject with an organotypic tissue equivalent prepared according to the disclosed method is also provided.

Any molecule that inhibits expression or activity of ROCK is contemplated for use with the provided compositions and methods. For example, the ROCK inhibitor can be a small molecule, an antibody, a negative regulator or an antisense compound. In particular examples, the inhibitor is a small molecule ROCK inhibitor, such as Y-27632.

The foregoing and other objects, features, and advantages of the invention will become more apparent from the following detailed description, which proceeds with reference to the accompanying figures.

BRIEF DESCRIPTION OF THE FIGURES

FIG. 11: Telomerase expression increases over time and telomere ends stabilize at a critical threshold length after culture with Y-27632.

FIG. 12: Expression of p16, p53, p21 and Myc in cells cultured with Y-27632.

FIGS. 13A-13D: Keratinocytes are still able to differentiate in organotypic raft culture after long term culture with Y-27632. Shown are H&E stained histological sections of primary keratinocytes grown in the absence of drug at P1 (A) or Y-27632-immortalized cells at P18 (B) in Y-27632, cultured in organotypic raft culture for 17 days, and P1 primary keratinocytes grown in organotypic raft culture for 14 days in raft media without (C) or with 10 μM Y-27632 (D).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 26, 2011, 70.3 KB, which is incorporated by reference herein. In the accompanying sequence listing:

SEQ ID NO: 1 is the nucleotide sequence of human ROCK1 (GenBank Accession No. NM_005406).

SEQ ID NO: 2 is the amino acid sequence of human ROCK1 (GenBank Accession No. NM_005406).

SEQ ID NO: 3 is the nucleotide sequence of human ROCK2 (Genbank Accession No. NM_004850).

SEQ ID NO: 4 is the amino acid sequence of human ROCK2 (Genbank Accession No. NM_004850).

SEQ ID NOs: 5-8 are the nucleotide sequences of primers used in the telomere length assay.

DETAILED DESCRIPTION

I. Introduction

It is disclosed herein that inhibition of Rho-associated kinase (ROCK) significantly increases the proliferation of primary keratinocytes and enables these cells to bypass senescence. This disclosure provides the first description of a defined chemical compound that mediates efficient cell immortalization.

Figure 1:
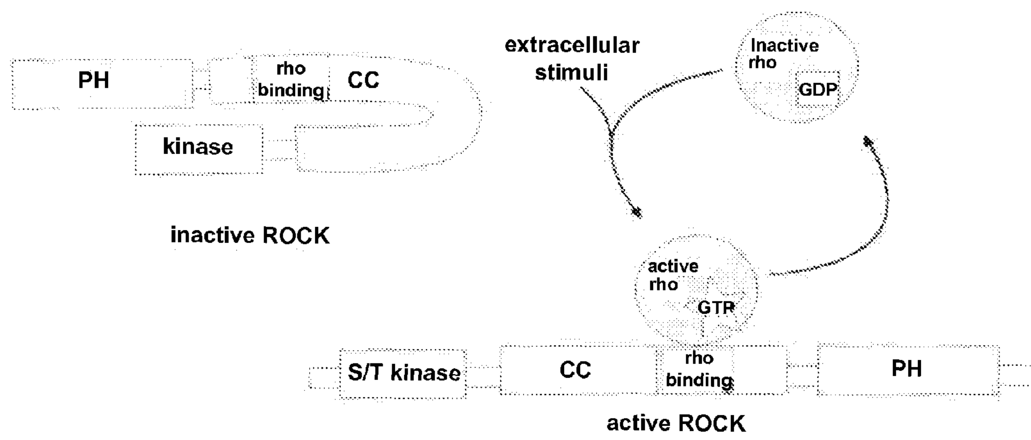
FIG. 1: The kinase activity of ROCK is auto-inhibited by an intramolecular interaction in which the C-terminal PH (Plekstrin homology) domain and the rho binding region of the CC (coiled coil) domain interact with and inhibits the kinase domain. Binding of GTP-bound rho disrupts this interaction and activates the ROCK kinase.
Figure 2:
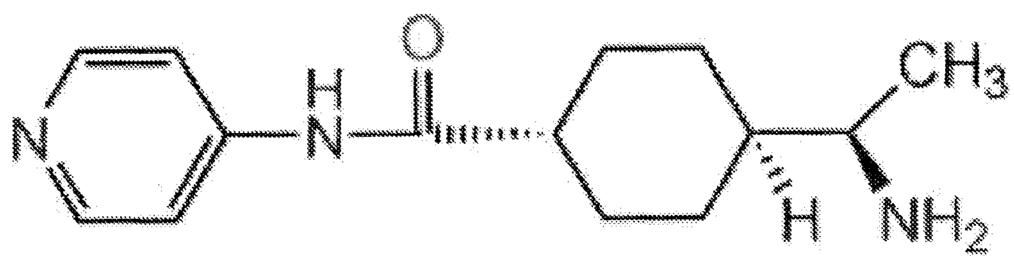
FIG. 2: A schematic of the chemical structure of Y-27632.

Mammalian cells encode two Rho kinases, ROCK1 and ROCK2. These kinases are activated by binding to an active, GTP-bound Rho GTPase (see FIG. 1). ROCK phosphorylates a number of substrates on serine or threonine residues. These substrates are involved in a wide range of cell behavior. For example, myosin light chain phosphatase, involved in stress fiber formation and contractility; LIM kinase, involved in actin stabilization; NHE1 involved in focal adhesions and actin; and PTEN and Ezrin, involved in apoptosis (Mueller et al., *Nat. Rev. Drug Discov.* 4:387-398, 2005; Riento et al., *Nat. Rev. Mol. Cell Biol.* 4:446-456, 2003). ROCK inhibitors such as Y-27632 (see FIG. 2) and fasudil bind to the catalytic site in the kinase domain and displace ATP (Jacobs et al., *J. Biol. Chem.* 281:260-268, 2006). These inhibitors have been found to have diverse and profound effects on cell behavior and have great therapeutic promise in many areas of disease.

The results described herein show that primary keratinocytes treated with a ROCK inhibitor have greatly increased proliferation, become immortalized, retain the ability to differentiate, and can very efficiently support HPV DNA replication. As disclosed herein, treatment with a ROCK inhibitor resulted in bypass of senescence and immortalization of different types of keratinocytes from human foreskin, and vaginal and cervical epithelium. Efficient immortalization occurred in the presence of fibroblast feeder cells. As demonstrated herein, keratinocytes immortalized using a ROCK inhibitor are functionally equivalent to normal cells; they have a normal karyotype, an intact DNA damage response and are able to form a stratified epithelium in organotypic culture. The immortalized keratinocytes exhibit upregulated telomerase mRNA levels and have telomeres that are shortened, but remain at a stable length. Myc mRNA levels also are increased in ROCK inhibitor immortalized keratinocytes.

Thus, these cells are very useful for a variety of therapeutic and research purposes. For example, immortalized keratinocytes are useful for studying the pathogenesis of many different skin-related diseases. Furthermore, since these cells can form organotypic skin equivalents in culture, they can be used as epidermal autographs for wound repair of burns or chronic ulcers. The immortalized keratinocytes disclosed herein are also useful for studying various aspects of the HPV life cycle. They provide the ideal host cell for the long term study of 'low-risk' HPVs that are unable to immortalize keratinocytes. Furthermore, inhibition of the ROCK pathway also increases the replication efficiency of 'high risk' HPVs, most likely because of the increase in cell proliferation and plating efficiency.

The greatly extended proliferative capacity of primary human keratinocytes treated with Rho kinase inhibitors is also invaluable for research of many aspects of keratinocyte biology or keratinocyte associated therapeutics.

II. Abbreviations

EGF Epidermal growth factor
FBS Fetal bovine serum
H&E Hematoxylin & Eosin
HCK Human cervical keratinocytes
HFK Human foreskin keratinocytes
HPV Human papilloma virus
hTERT Human telomerase reverse transcriptase
HVK Human vaginal keratinocytes
PCR Polymerase chain reaction
PH Plekstrin homology
QRT-PCR Quantitative reverse transcription-PCR
ROCK Rho-associated kinase
SDS Sodium dodecyl sulfate III. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. As used herein, the term antibody includes intact immunoglobulins as well as a number of well-characterized fragments produced by digestion with various peptidases, or genetically engineered artificial antibodies. Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

Also specifically contemplated are human antibodies (arising from human genes) and humanized antibodies, either of which is suitable for administration to humans without engendering an adverse immune response by the human against the administered immunoglobulin. Humanized forms of antibodies are chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin. Humanization can be performed following methods known in the art, such as by substituting rodent CDRs or CDR sequences for the corresponding sequences of a human antibody (see, for instance, U.S. Pat. No. 5,225,539; Jones et al., *Nature* 321(6069):522-525, 1986; Riechmann et al., *J Mol Biol.* 203(3):825-828, 1988; Verhoeyen et al., *Science* 239(4847):1534-1536, 1988; Riechmann et al., *Nature* 332(6162):323-327 1988; or Verhoeyen et al., *Bioessays* 8(2):74-78, 1988). Antibodies specific for IaI are known in the art (see, for example, U.S. Pat. No. 6,660,482; U.S. Patent Application Publication No. 2007/0297982; and Lim et al., *J. Infect. Dis.* 188:919-926, 2003).

Antisense compound: Refers to an oligomeric compound that is at least partially complementary to the region of a target nucleic acid molecule to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression. In one embodiment, the target nucleic acid molecule is ROCK1. In another embodiment, the target nucleic acid molecule is ROCK2. Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target mRNA, the duplex is recognized by RNase H (an enzyme that recognizes DNA:RNA duplexes), resulting in cleavage of the mRNA.

Differentiate or differentiation: Refers to the process by which a pluripotent cell becomes distinct in form and function (i.e., develops into a specialized cell, such as a skin cell). For example, an embryonic stem cell can differentiate into an epithelial cell, such as a keratinocyte. Differentiate can also refer to the process a specific cell type undergoes to become more specialized. For example, a keratinocyte can differentiate from a basal keratinocyte to more specialized keratinocytes in a stratified squamous epithelium.

Effective amount: As used herein, an "effective amount of a ROCK inhibitor" is the amount of inhibitor required to inhibit expression of ROCK or inhibit activity of ROCK. For example, when the ROCK inhibitor is a small molecule, antibody or negative regulator of ROCK, an effective amount is the concentration required to partially or completely eliminate ROCK activity, such as its kinase activity. In some examples, the ROCK inhibitor is Y-27632. In one embodiment, an effective amount of Y-27632 is at least 1 μM. In another embodiment, an effective amount of Y-27632 is at least 5 μM. In another embodiment, an effective amount of Y-27632 is at least 10 μM. In some embodiments, the effective amount of ROCK inhibitor is about 1 to about 100 μM, about 5 to about 25 μM, or about 10 μM. In another example, the ROCK inhibitor is an antisense compound. An effective amount of an antisense compound specific for ROCK is an amount required to inhibit ROCK mRNA level by at least about 10%, at least about 20%, at least about 30%, at least about 40% or at least about 50%. An effective amount of a ROCK inhibitor can also refer to the amount required to achieve a particular effect, such as immortalization of a primary keratinocyte.

Epithelial cells: Cells that line the exterior of a organism (e.g., skin, cornea), body lumens (e.g., gastrointestinal tract, urinary tract, reproductive tract, lungs) and mucous membranes (e.g., oesophagus, mouth and rectum). Epithelial cells also make up exocrine and endocrine glands.

Expand: A process by which the number or amount of cells in a cell culture is increased due to cell division. Similarly, the terms "expansion" or "expanded" refers to this process. The terms "proliferate," "proliferation," "proliferated" or "outgrowth" may be used interchangeably with the words "expand," "expansion," or "expanded."

Expose: To bring into contact with. As used herein, exposing cells to an inhibitor generally refers to culturing or incubating the cells in the presence of the inhibitor.

Feeder cells: Cells that are used in culture with other types of cells to assist in their growth. Feeder cells are growth arrested (such as by irradiation), but viable and form a substratum on which other cells can growth. Feeder cell layers provide an intact and functional extracellular matrix and typically secrete factors into the medium, such as matrix-associated factors and cytokines, which can assist in the growth of other cells. In some embodiments, feeder cells are fibroblast cells, such as a fibroblast cell line. In particular examples, the feeder cells are irradiated 3T3 J2 cells. In other examples, the feeder cells are murine embryonic fibroblasts.

Fibroblast: A type of cell that synthesizes the extracellular matrix and collagen, the structural framework (stroma) for animal tissues, and plays a critical role in wound healing. Fibroblasts are the most common cells of connective tissue in animals.

Human papillomavirus (HPV): A type of virus that infects the skin and mucous membranes of humans. HPVs are phylogenetically categorized into five genera: alpha, beta, gamma, mu and nu. Approximately 130 HPV types have been identified, some of which have been shown to cause warts (verrucae) or cancer (such as cervical cancer). Papillomaviruses are DNA viruses with a non-enveloped viron having icosahedral symmetry. The double-stranded, circular HPV DNA genome contains one coding region for late genes, one coding region for early genes, and a non-coding upstream regulatory region with binding sites for the various transcription factors controlling expression of early and late genes. Two separate open reading frames in the late gene coding region encode viral capsid proteins L1 and L2. Capsid protein L1 is the major capsid protein that is highly conserved among different HPV types. Eight open reading frames in the early gene coding region encode eight viral early proteins, designated E1, E2, E3, E4, E5, E6, E7, and E8. Early proteins E6 and E7 are oncoproteins critical for host cell immortalization and transformation, as well as for long term viral replication and survival.

"High-risk" HPV includes HPV types that are associated with malignant cancers, such as cervical carcinoma and head and neck cancers. High-risk HPVs are capable of immortalizing primary keratinocytes in culture. Examples of high-risk HPVs include, but are not limited to, HPV types 16, 18, 31, 33, 35, 39, 45, 51, 52, 56, 58, 59 and 68.

"Low-risk" HPV includes HPV types that are not associated with malignant cancers, but are known to cause a wide range of benign, hyperproliferative conditions such as genital warts, cutaneous warts and respiratory papillomatosis. The E6 and E7 proteins of low-risk HPVs are not capable (in the absence of other factors) of immortalizing primary cells in culture. Examples of low-risk HPVs include, but are not limited to, HPV types 1, 2, 3, 4, 6, 7, 11, 42, 43, 44 and 55.

Immortalized cell: A cell that has bypassed senescence and is capable of continuous growth in culture.

Inhibitor of ROCK: As used herein, a ROCK inhibitor is a protein, nucleic acid, small molecule, antibody or other agent that prevents expression of ROCK or down-regulates ROCK activity, such as its kinase activity. Examples of ROCK inhibitors are disclosed herein. ROCK inhibitors include, but are not limited to, small molecules, antibodies, antisense compounds and negative regulators of ROCK. ROCK inhibitors include inhibitors of ROCK-1, ROCK-2 or both. In some examples, the ROCK inhibitor is Y-27632.

Isolated: An "isolated" biological component (such as a nucleic acid molecule, protein or cell) has been substantially separated or purified away from other biological components in the cell or tissue from which the component naturally occurs. As used herein, an "isolated" cell is a cell that has been substantially separated from the tissue from which it is derived.

Keratinocyte: A cell found in the epidermis that produces keratin. Keratinocytes make up about 90% of epidermal cells. Keratinocytes are produced by keratinocyte stem cells in the basal layer of the epidermis. As used herein, "primary keratinocytes" are keratinocytes isolated from tissue and grown in culture, but are not immortalized. In the context of the present disclosure, an "immortalized primary keratinocyte" is a primary keratinocyte that has become immortalized, such as by culturing the cell in the presence of a ROCK inhibitor. In some embodiments, the primary keratinocyte is a foreskin keratinocyte, a vaginal keratinocyte, a cervical keratinocyte, an oral keratinocyte or a cutaneous keratinocyte.

MicroRNA (miRNA): Single-stranded RNA molecules that regulate gene expression. miRNAs are generally 21-23 nucleotides in length. miRNAs are processed from primary transcripts known as pri-miRNA to short stem-loop structures called pre-miRNA and finally to functional miRNA. Mature miRNA molecules are partially complementary to one or more messenger RNA molecules, and their primary function is to down-regulate gene expression. MicroRNAs regulate gene expression through the RNAi pathway.

Organotypic tissue equivalent: A cell culture characterized by the organized growth of the cells in a form resembling a tissue (also referred to herein as an "organotypic cell culture"). In some embodiments, the organotypic tissue equivalent is an organotypic skin equivalent.

Percent identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Res.* 16:10881-10890, 1988; Pearson and Lipman, *Proc. Natl. Acad. Sci. USA* 85:2444, 1988; and Altschul et al., *Nature Genet.* 6:119-129, 1994. The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Pharmaceutically acceptable carrier: The pharmaceutically acceptable carriers (vehicles) useful in this disclosure are conventional. *Remington's Pharmaceutical Sciences*, by E.W. Martin, Mack Publishing Co., Easton, Pa., 15th Edition (1975), describes compositions and formulations suitable for pharmaceutical delivery of one or more therapeutic compounds or molecules, such as one or more nucleic acid molecules, proteins, antibodies, cells or small molecules, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Primary cell: A non-immortalized cell taken from a living organism or tissue source.

Prolonging viability: As used herein, "prolonging viability" of a cell, such as a primary cell, refers to extending the duration of time the cell is capable of normal growth and/or survival.

Rho-associated kinase (ROCK): Also known as Rho-associated coiled-coil kinase and Rho kinase. The ROCK family includes ROCK1 (also called ROKβ or p160ROCK) and ROCK2 (also called ROKα). ROCK proteins are serine-threonine kinases that interact with Rho GTPases. Nucleotide and amino acid sequence of exemplary human ROCK1 and ROCK2 are set forth herein as SEQ ID NOs: 1-4.

Ribozyme: A catalytic RNA molecule. In some cases, ribozymes can bind to specific sites on other RNA molecules and catalyze the hydrolysis of phosphodiester bonds in the RNA molecules.

Senescence: Refers to the point at which a cell is no longer capable of undergoing mitosis (cell division).

Short hairpin RNA (shRNA): A sequence of RNA that makes a tight hairpin turn and can be used to silence gene expression via the RNAi pathway. The shRNA hairpin structure is cleaved by the cellular machinery into siRNA.

Small interfering RNA (siRNA): A double-stranded nucleic acid molecule that modulates gene expression through the RNAi pathway. siRNA molecules are generally 20-25 nucleotides in length with 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs."

Small molecule inhibitor: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and non-human mammals.

Therapeutically effective amount: A quantity of a specified agent sufficient to achieve a desired effect in a subject, cell or culture being treated with that agent.

Y-27632: A small molecule inhibitor that selectively inhibits activity of Rho-associated kinase. Also known as (+)-trans-N-(4-Pyridyl)-4-(1-aminoethyl)-cyclohexanecarboxamide. Y-27632 is disclosed in U.S. Pat. No. 4,997,834 and PCT Publication No. WO 98/06433.

Unless otherwise explained, all technical and scientific terms used herein have the same meaning as commonly understood by one of ordinary skill in the art to which this invention belongs. The singular terms “a,” “an,” and “the” include plural referents unless context clearly indicates otherwise. Similarly, the word “or” is intended to include “and” unless the context clearly indicates otherwise. Hence “comprising A or B” means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, GenBank accession numbers and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

Described herein is the finding that treatment of primary keratinocytes with a ROCK inhibitor increases their proliferative capacity and induces immortalization of these cells. The immortalized keratinocytes exhibit characteristics typical of normal primary keratinocytes, including having a normal karyotype and an intact DNA damage response. In addition, primary keratinocytes immortalized by exposure to a ROCK inhibitor retain the capacity to differentiate into stratified epithelium upon removal of the ROCK inhibitor. Further disclosed herein is the finding that primary keratinocytes treated with a ROCK inhibitor support viral replication of both low-risk and high-risk human papillomaviruses.

Thus, disclosed herein is a method of immortalizing primary keratinocytes, comprising culturing the primary keratinocytes in the presence of an effective amount of a ROCK inhibitor for a period of time sufficient to allow immortalization of the primary keratinocytes. In some embodiments, the method further comprises continuing to culture the immortalized keratinocytes in the absence of the ROCK inhibitor. As disclosed herein, the immortalized keratinocytes retain the capacity to differentiate when cultured in the absence of the ROCK inhibitor.

As used herein, culturing in the absence of a ROCK inhibitor does not require the complete absence of a ROCK inhibitor. For example, low or trace levels of a ROCK inhibitor may be present in the culture medium such that the level is below the threshold required to enhance proliferation, induce differentiation and/or inhibit differentiation of a primary keratinocyte. In some embodiments, culturing primary keratinocytes in the absence of a ROCK inhibitor comprises culturing the primary keratinocytes in the presence of less than about 1 μM, less than about 0.1 μM, less than about 0.01 μM, or less than about 0.001 μM ROCK inhibitor. In some embodiments, the primary keratinocytes are cultured in the complete absence of a ROCK inhibitor. Culturing in the absence of a ROCK inhibitor refers both to the original ROCK inhibitor present in the culture, as well as other types of ROCK inhibitor.

Culturing primary keratinocytes in the absence of ROCK inhibitor can be achieved by any one of a number of suitable means, such as by replacing ROCK inhibitor-containing media with fresh media lacking ROCK inhibitor. Alternatively, ROCK inhibitor can be removed from the existing media, such as by dialyzing the media.

In some embodiments of the method, continuing to culture the immortalized keratinocytes comprises culturing the immortalized keratinocytes until they form an organotypic tissue equivalent. In some embodiments, culturing the primary keratinocytes comprises culturing the primary keratinocytes in the presence of fibroblast feeder cells.

Also provided herein is a method of increasing proliferation of primary keratinocytes by culturing the primary keratinocytes in the presence of an effective amount of a ROCK inhibitor. In some embodiments, the method comprises culturing the primary keratinocytes in the presence of the ROCK inhibitor for a period of time sufficient to allow immortalization of the primary keratinocytes.

The primary keratinocytes can be any type of primary keratinocyte. In some examples, the primary keratinocyte is a foreskin keratinocyte, vaginal keratinocyte or cervical keratinocyte.

The ROCK inhibitor can be any type of molecule that inhibits expression or activity of ROCK, such as a small molecule inhibitor, antibody, antisense compound or negative regulator. Suitable ROCK inhibitors are discussed in greater detail below. In some embodiments, the ROCK inhibitor is a small molecule inhibitor. In particular examples, the ROCK inhibitor is Y-27632.

In some embodiments, when the ROCK inhibitor is Y-27632, the effective amount of the ROCK inhibitor is about 1 to about 100 μM, or about 5 to about 25 μM, or about 10 μM.

The ROCK inhibitor can also be a negative regulator of ROCK, such as, but not limited to small GTP-binding proteins such as Gem, RhoE and Rad. In other examples, the ROCK inhibitor is an antibody that specifically binds ROCK1 or ROCK2 or both isoforms. In one example, the antibody specifically binds ROCK1 (SEQ ID NO: 2). In another example, the antibody specifically binds ROCK2 (SEQ ID NO: 4).

In other examples, the ROCK inhibitor is an antisense compound. Antisense compounds include, but are not limited to, antisense oligonucleotides, siRNA, miRNA, shRNA and ribozymes. Antisense compounds specifically target ROCK nucleic acids. In one example, a ROCK antisense compound specifically hybridizes with ROCK1 (SEQ ID NO: 1). In another example, a ROCK antisense compound specifically hybridizes with ROCK2 (SEQ ID NO: 3).

As described herein, the primary keratinocytes are cultured in the presence of the ROCK inhibitor for a period of time sufficient to allow immortalization. In some embodiments, the primary keratinocytes are cultured in the presence of the ROCK inhibitor for at least 15 days, at least 20 days, at least 40 days, at least 60 days, at least 100 days, at least 150 days, at least 200 days, at least 250 days, at least 300 days, at least 350 days, at least 400 days, at least 450 days, or at least 500 days.

Also provided herein are isolated immortalized primary keratinocytes produced by the disclosed method.

Further provided are cell cultures comprising isolated immortalized primary keratinocytes produced by the disclosed method.

Organotypic tissue equivalents comprising immortalized primary keratinocytes produced by the disclosed method are also provided.

Further provided are organotypic tissue equivalents comprising immortalized primary keratinocytes. The primary keratinocytes are immortalized by culturing the primary keratinocytes in the presence of an effective amount of a ROCK inhibitor for a period of time sufficient to allow immortalization of the primary keratinocytes and are further cultured in the absence of the ROCK inhibitor. When cultured in the absence of the ROCK inhibitor, the immortalized keratinocytes differentiate to form the organotypic tissue equivalent.

In some examples, the organotypic tissue equivalents described herein comprise primary keratinocytes that have been cultured in the presence of a ROCK inhibitor to increase proliferation of these cells, but the cells are not yet immortalized. Thus, also provided are organotypic tissue equivalents comprising primary keratinocytes that have been cultured in the presence of a ROCK inhibitor for a period of time sufficient to increase proliferation of the primary keratinocytes.

In some embodiments, culturing the primary keratinocytes comprises culturing the primary keratinocytes in the presence of fibroblast feeder cells.

The organotypic tissue equivalent can be comprised of any type of primary keratinocyte. In some embodiments, the primary keratinocytes are foreskin keratinocytes, vaginal keratinocytes, cervical keratinocytes, oral keratinocytes or cutaneous keratinocytes.

Also provided are compositions comprising an isolated immortalized primary keratinocyte. The compositions include a primary keratinocyte immortalized by culturing the primary keratinocyte in the presence of an effective amount of a ROCK inhibitor for a period of time sufficient to allow immortalization of the primary keratinocyte. In some embodiments, the immortalized keratinocyte is further cultured in the absence of the ROCK inhibitor. The immortalized keratinocyte retains the capacity to differentiate when cultured in the absence of the ROCK inhibitor. In some embodiments, culturing the primary keratinocytes comprises culturing the primary keratinocytes in the presence of fibroblast feeder cells.

In some embodiments, the composition further comprises a pharmaceutically acceptable carrier. In some embodiments, the immortalized primary keratinocyte is part of an organotypic tissue equivalent. In some embodiments, the composition is suitable for application to human skin. For example, the composition can include an ointment or viscous material suitable for application to and retention on the skin. Such pharmaceutically acceptable carriers are known in the art.

Further provided is a method of promoting human papilloma virus (HPV) replication in primary keratinocytes. In some embodiments, the method comprises infecting the primary keratinocytes with HPV or transfecting the primary keratinocytes with an HPV genome, and culturing the primary keratinocytes in the presence of an effective amount of a ROCK inhibitor, thereby promoting HPV replication in primary keratinocytes.

In some embodiments, the method further comprises culturing the primary keratinocytes in the presence of the ROCK inhibitor prior to infection with HPV or transfection with the HPV genome. In some embodiments, the primary keratinocytes are cultured in the presence of fibroblast feeder cells.

The primary keratinocytes can be any type of keratinocyte suitable for propagation of HPV. In particular examples, the primary keratinocytes are foreskin keratinocytes, vaginal keratinocytes or cervical keratinocytes.

The ROCK inhibitor can be any type of ROCK inhibitor (discussed in greater detail below). In some embodiments, the ROCK inhibitor is a small molecule inhibitor. In particular examples, the ROCK inhibitor is Y-27632.

In some embodiments, when the ROCK inhibitor is Y-27632, the effective amount of the ROCK inhibitor is about 1 to about 100 μM, about 5 to about 25 μM, or about 10 μM.

The primary keratinocytes are cultured in the presence of the ROCK inhibitor for any suitable period of time to allow for an enhancement in HPV replication. In some embodiments, the primary keratinocytes are cultured in the presence of the ROCK inhibitor for at least 15 days, at least 20 days, at least 40 days, at least 60 days, or at least 100 days. The primary keratinocytes can be cultured in the presence of the ROCK inhibitor before or during, or both before and during infection with HPV.

The HPV can be from any genus (alpha, beta, gamma, mu or nu). In some embodiments, the HPV is an alpha, beta or gamma HPV. The HPV can be a low-risk HPV or a high-risk HPV. In some embodiments, the HPV is a low-risk HPV, such as HPV type 1, 2, 3, 4, 6, 7, 11, 42, 43, 44 and 55. In particular examples, the low-risk HPV is HPV6. In some embodiments, the HPV is high-risk, such as HPV type 16, 18, 31, 33, 35, 39, 45, 51, 52, 56, 58, 59 or 68. In particular examples, the high-risk HPV is HPV18.

Also provided is a method of preparing an organotypic tissue equivalent. The method includes obtaining isolated primary keratinocytes; culturing the primary keratinocytes in the presence of an effective amount of a ROCK inhibitor for a period of time sufficient to allow for proliferation of the primary keratinocytes; and continuing to culture the primary keratinocytes in the absence of the ROCK inhibitor, thereby allowing the primary keratinocytes to differentiate and form an organotypic tissue equivalent.

In some embodiments, the primary keratinocytes are obtained by a tissue biopsy. In some examples, the tissue biopsy is taken from the skin (e.g., the cutaneous and/or mucosal squamous epithelium).

Further provided is a method of treating a wound or skin disease in a subject, comprising treating the subject with an organotypic tissue equivalent prepared according to the method disclosed herein. In some embodiments, the wound is a burn or ulcer. In some embodiments, the primary keratinocytes are obtained by a tissue biopsy of the subject to be treated with the organotypic tissue equivalent (thus, the organotypic tissue equivalent is an autograft). In particular examples, the tissue is skin.

V. Keratinocyte Proliferation, Immortalization and Differentiation

Somatic cells have a limited lifespan and gradually slow in growth and stop dividing, a process known as cellular senescence. This process is thought to limit the vulnerability of aging cells to disease. Human keratinocytes are invaluable for the study of skin biology and the pathogenesis of skin-related diseases, but their short lifespan in culture is a limitation. Different conditions have been developed to optimize the culture of keratinocytes; the presence of fibroblast feeder cells increases the proliferative capacity of primary keratinocytes from approximately 20 to 40-60 population doublings (Ramirez et al. *Genes Dev.* 15: 398-403, 2001).

Spontaneous immortalization of human cells is rare. Primary keratinocytes can only proliferate for a limited number of cell divisions before they undergo replicative senescence (Ben-Porath and Weinberg, *Cell Biol.* 37:961-976, 2005; Liu et al., *J. Virol.* 82: 11568-11576, 2008). Several viral oncogenes can efficiently immortalize cells in culture, such as the E6 and E7 proteins from oncogenic types of HPV, T-antigen from SV40, and E1A and E1B from adenovirus. Retinal pigment epithelial cells and foreskin fibroblasts can be efficiently immortalized by exogenous expression of the catalytic subunit of human telomerase (Bodnar et al., *Science* 279: 349-352, 1998). However, most studies find that expression of hTERT is not sufficient for keratinocyte immortalization and additional changes, such as disruption of $p16^{INK4a}$ function, are also required (Kiyono et al., *Nature* 396: 84-88, 1998; Dickson et al., *Mol. Cell Biol.* 20: 1436-1447, 2000) Immortalization of human keratinocytes is very rare and only a few immortalized cell lines exist. These cell lines have genetic abnormalities such as p53 mutations in HaCaT cells (Lehman et al., *Carcinogenesis* 14:833-839, 1993) or an extra isochromosome of the long arm of chromosome 8 in the NIKs cell line (Allen-Hoffmann et al., *J. Invest Dermatol.* 114:444-455, 2000).

The events leading to senescence of human keratinocytes are well known. Cells in culture demonstrate increasing levels of the $p16^{ink4}$ cyclin dependent kinase inhibitor until the cells reach senescence and cease to proliferate. This is concomitant with a gradual erosion of telomeres which also results in a growth crisis. The high risk HPVs are able to abrogate this process. The E7 protein inactivates and degrades the pRb retinoblastoma protein and induces G1/S phase progression of the cell cycle (Wise-Draper and Wells, *Front Biosci.* 13:1003-1017, 2008). This process increases the levels of $p16^{ink4}$ but the inactivation of the pRb pathway renders it functionless (Kiyono et al., *Nature* 396:84-88, 1998). The E6 protein inactivates the p53 protein that is induced in response to the usurpation of the pRb pathway and activates telomerase which abrogates the erosion of the telomeres and allows the cells to proliferate beyond senescence.

This disclosure describes the effect of a ROCK inhibitor, Y-27632, on keratinocyte proliferation and immortalization and subsequent effects on HPV DNA replication. These observations could have far-reaching implications for the study and treatment of HPV disease. The greatly improved culture and extended lifespan of keratinocytes is also invaluable for both research and therapeutic purposes.

It is also important to determine whether ROCK inhibition changes the ability of the keratinocytes to differentiate. Studies of the complete viral life cycle require that cells containing the replicating viral genome can differentiate to switch the life cycle into the late stage necessary for the production of progeny virions. Studies on the effect of Y-27632 on keratinocyte differentiation have been controversial. Y-27632 enhances the survival rate of human embryonic stem cells following cryopreservation and the resulting treated cells are able to fully differentiate into all three germ layers after long term culture (Li et al., *Stem Cells Dev* 6:1079-1085, 2008). However, ROCK inhibition has also been reported to abrogate suspension-induced differentiation in keratinocytes (McMullan et al., *Current Biology* 13:2185-21 89, 2003), but another study showed that differentiation is negatively regulated by Rho signaling (Grossi et al., *Proc. Natl. Acad. Sci. USA* 102:11313-11318, 2005). It is disclosed herein that ROCK inhibitor immortalized keratinocytes retain the ability to differentiate and express appropriate differentiation markers.

VI. Use of ROCK Inhibitor Immortalized Keratinocytes

A. HPV-related Studies

ROCK-inhibited keratinocytes are useful for studying all modes of HPV replication. It is shown herein that the efficiency of initial replication and maintenance replication is greatly increased in the presence of a ROCK inhibitor. An increase in virion production will be of great research benefit and can provide useful reagents for serological studies, for testing vaccines and for identifying receptors using authentic viral particles.

Efficient replication of "low-risk" HPV genomes will allow a much greater understanding of the life cycle of these less well understood viruses. Although not associated with cancer, these viruses are responsible for a great burden of recalcitrant disease such as genital warts, respiratory papillomatosis and cutaneous warts. These lesions can be especially problematic in individuals who are immunocompromised by HIV infection or organ transplant. Efficient means of studying the viral life cycle will allow testing of anti-viral therapies in a system that closely reflects the in vivo situation.

Most HPV studies use keratinocytes derived from neonatal foreskins because of the availability of this tissue from routine circumcision. However, these keratinocytes might not be the best host for papillomavirus studies as HPV infection of the foreskin is mostly clinically unapparent. A more appropriate cell type for the study of the cancer associated HPVs is that of the uterine cervix and in particular cells from the transformation zone between the ectocervix and the endocervix. Because of the difficulties in obtaining such tissue, only a few HPV studies have used cervical tissue. Different HPVs have a very specific tropism for different regions of epithelia. ROCK inhibitor treatment and expansion of small numbers of keratinocytes derived from different types of epithelia could greatly increase the understanding of HPV biology.

Figure 6:
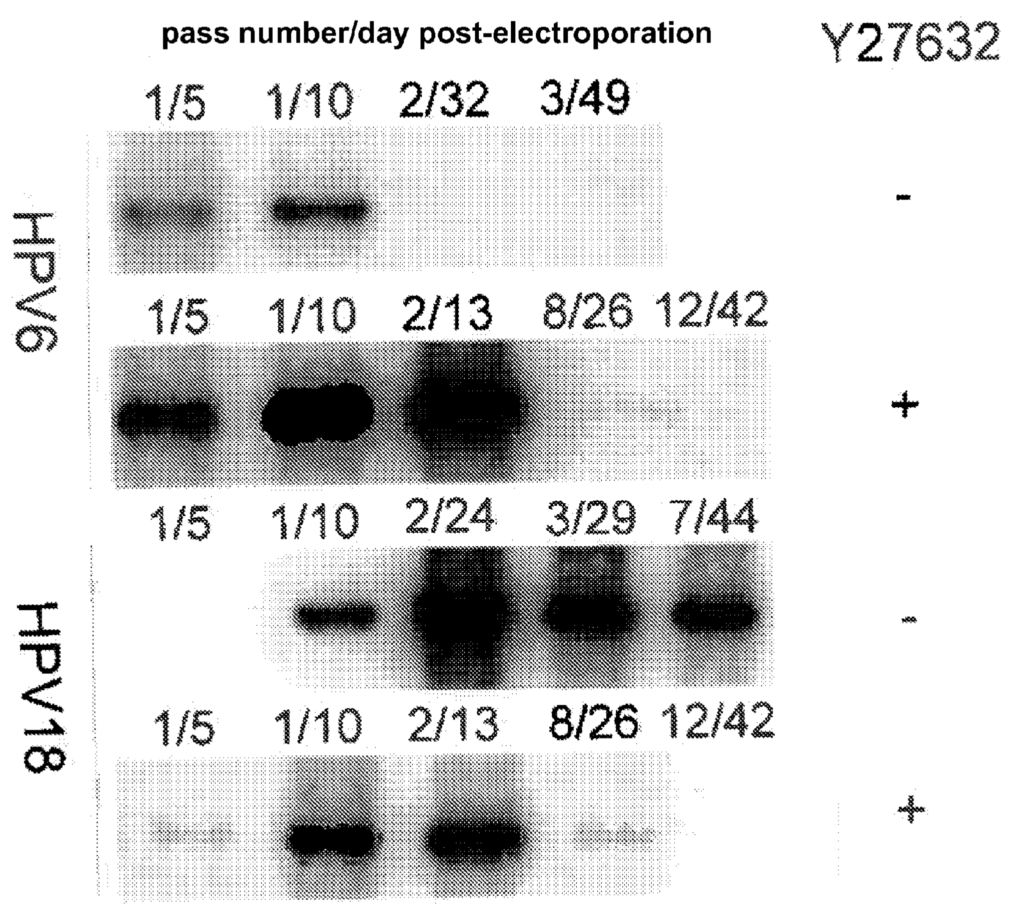
FIG. 6: Long-term replication assay of "low-risk" HPV6 and "high-risk" HPV18 in the presence or absence of 10 μM Y-27632. The pass number of the cells post-electroporation at which DNA was isolated is shown along the bottom of the figure and the corresponding number of days at the top of each image.

Remarkably, cervical carcinoma cell lines that have been in culture for decades still rely on the function of the E6 and E7 oncoproteins for continued proliferation and survival. Down-regulation of E6 and E7 expression results in immediate senescence of these cell lines (Goodwin et al., *Proc. Natl. Acad. Sci. USA* 97: 10978-10983, 2000). Disclosed herein is the finding that treatment of cells with Y-27632 removes the growth advantage conferred by the E6 and E7 oncoproteins (FIG. 6). In the absence of this selection, there is no need to maintain the viral genomes and they are gradually lost. This observation could be the basis of a therapy for persistent HPV infections. A combination of ROCK inhibitor treatment and a therapy to interfere with extrachromosomal viral DNA replication could clear infection from persistently infected cells.

The studies described herein have focused on replication of papillomaviruses in ROCK inhibitor-treated keratinocytes but the same approach can be used for other epitheliotropic viruses. For example, a range of herpesviruses and poxviruses have been shown to infect and replicate in keratinocyte organotypic raft cultures and these are used to test anti-viral therapies in a system that closely resembles natural infection (Jeon et al., *J. Virol.* 69:2989-2997, 1995).

B. Therapeutic Uses

The Rho/ROCK pathway has been shown to function in the cardiovascular system, central nervous system, cancers, and embryonic development (Shi et al., *Arch. Immunol. Ther. Exp. (Warsz.)* 55:61-75, 2007). This pathway is an important therapeutic target and one ROCK inhibitor (fasudil) is already marketed for cerebral vasospasm after surgery (Shihuya et al., *Acta Neurochir. Suppl* 77:201-204, 2001) and is currently being tested for the treatment of angina pectoris, acute cerebral thrombosis and other vascular diseases. Studies in animal models suggest widespread therapeutic benefits in the treatment of inflammation, fibrosis and neurological disorders (Kubo et al., *Ther. Clin. Risk Manag.* 4:605-615, 2008; Olson, *Curr. Opin, Cell Biol.* 20:242-248, 2008).

Large scale production of keratinocytes from a small number of cells, especially from individual hosts, is very valuable therapeutically. A small number of keratinocytes from a biopsy can be isolated, expanded in monolayer culture and developed into organotypic skin equivalents (Phillips, *Arch. Dermatol.* 135:977-978, 1999). These tissue sheets are very useful for epidermal replacement of regions of ulcers and burns.

Increased cell proliferation due to ROCK inhibition would greatly increase the amount of tissue generated and decrease the time required. It could also allow the use of donor graft tissue from more appropriate regions of the epithelium to be expanded.

Keratinocyte-mediated gene therapy is an intensively studied topic of research (Therrien et al., *Toxicol. Pathol.* 36:104-111, 2008). Autologous keratinocytes can be isolated and transfected or transduced with a vehicle expressing a therapeutic gene. Increased cellular proliferation and immortalization due to ROCK inhibition could greatly enhance the efficiency of this process. Notably, it has already been observed that Y-27632 can greatly increase the survival of embryonic stem cells (Watanabe et al., *Nature Biotechnology* 25:681-686, 2007).

In the dawn of the era of personalized medicine, it is becoming more and more important to test therapies directly on cells derived from the patient for which the therapy is eventually intended. Isolation of host keratinocytes and expansion in culture under conditions of ROCK inhibition could greatly increase the efficiency and time frame of this process. Patient-derived keratinocytes or tissue engineered skin equivalents could be used to test specific therapies to determine the outcome on the host. Large quantities of keratinocytes could be expanded from a small tissue biopsy of patients with specific diseases for research purposes. The ability to greatly expand these keratinocytes and derive tissue engineered skin from them will be of great research and therapeutic benefit.

Transplantation of apparently immortalized human keratinocytes onto human hosts raises concerns of uncontrolled growth and tumorogenicity. However, the experiment shown in FIG. 4 demonstrated that keratinocyte growth rate slows after withdrawal of Y-27632. In addition, it is also disclosed herein that ROCK inhibited keratinocytes have a normal karyotype and a normal DNA damage response. Thus, primary keratinocytes immortalized by exposure to a ROCK inhibitor would not be tumorigenic.

C. Organotypic Cultures and Tissue Equivalents

Preparation and use of organotypic cell cultures and tissue equivalents, including organotypic skin equivalents, have been described (see, for example, U.S. Patent Application Publication Nos. 2009/0280095, 2009/04228, 2006/0292126 and 2005/0079578; Stark et al., *Biological Procedures Online* 6: 55-60, 2004). An "organotypic culture" refers to a culture of cells that associate in a way that as closely as possible replicates the biochemical and physiological properties of the organ from which the cells are derived.

An organotypic cell culture is a cell culture characterized by the organized growth of the cells in a form resembling a tissue (also referred to herein as an "organotypic tissue equivalent"). As an example of an organotypic tissue equivalent, human primary keratinocytes are seeded onto a fibroblast-embedded (murine or human fibroblasts) collagen matrix and grown exposed to air. Within about 10 days keratinocytes resemble a stratified epithelia with the characteristic epidermal structure of human skin. These skin-equivalents have already been evaluated in clinical trials (Bell et al., *Science* 211:1052-1054, 1981; Greenberg et al., *Methods Mol. Biol.* 289:425-430, 2005).

Example 2 below describes a method for generating stratified epithelium using primary keratinocytes immortalized by exposure to a ROCK inhibitor. Similar methods can be employed to prepare an organotypic tissue equivalent for therapeutic purposes. As described herein, organotypic tissue equivalents are useful for the treatment of a variety or skin diseases or wounds.

Chronic wounds disrupt the integrity of the skin by tearing, cutting, piercing or breaking the tissue. The causes may be structural, such as injury, or physiological, such as an underlying disease. The most frequently occurring skin wounds are venous ulcers, pressure ulcers and diabetic foot ulcers.

Chronic wounds occur in individuals with underlying diseases of various types whose medical conditions compromise the body's ability to repair injured tissue on its own. Despite the use of a variety of medical and surgical treatments, chronic wounds can take months or even years to heal and frequently recur. These wounds are often large and unsightly and may be painful in some patients.

Chronic wounds are of three major types: venous stasis ulcers, diabetic ulcers and pressure ulcers. A venous ulcer is an ulceration that develops on the ankle or lower leg in patients with chronic vascular disease. In these patients, blood flow in the lower extremities is impaired, leading to edema (swelling) and mild redness and scaling of the skin that gradually progress to ulceration. Venous ulcers are a condition affecting 500,000-700,000 patients in the U.S. and 1.3 million people in the industrialized world.

A diabetic ulcer is a chronic wound that occurs in patients with diabetes. While the actual cause of the ulcer in these patients is an injury such as a callus, blister or foreign body such as a pebble or splinter, it is the patient's underlying disease that places him or her at high risk for developing an ulcer. Important risk factors include: inadequate local blood supply, which impairs their ability to repair injured tissue and ward off infection, and reduced sensation in the extremities, which causes the initial injury to go unrecognized until it becomes a serious, chronic wound. Diabetic ulcers are a condition affecting just under 500,000 patients in the US and 1.2 million people in the industrialized world.

A pressure ulcer is defined as any lesion caused by unrelieved pressure on tissues that are located over a bony prominence on the body. Pressure ulcers were formerly referred to as bedsores or decubitus ulcers. Pressure ulcers develop in immobile patients whose tissues are subjected to continuous pressure from bones on the interior and hard surfaces such as beds or chairs on the exterior. In addition to their immobility, patients at risk for the development of pressure ulcers typically have poor nutritional status, inadequate hydration, and other underlying medical conditions that compromise their ability to heal injuries. Pressure ulcers affect over 1.6 million people in the US and 4.1 million people in the industrialized world.

Organotypic tissue equivalents comprising primary keratinocytes immortalized by exposure to a ROCK inhibitor can be prepared using any technique known in the art. An exemplary procedure is described below (see U.S. Patent Application Publication No. 2006/0292126).

Organotypic tissue cultivation is generally performed in inserts with microporous membranes, which contain homologous or autologous human dermal fibroblasts (HDF), especially postmitotic HDF at their undersurface. HDF secrete factors that condition the medium in order to get a better growth of the epidermal equivalents. The HDF layer can be formed from between about $5\times10^3$ to $1\times10^5$ cells/cm$^2$, and in some cases approximately $1\times10^4$ to $5\times10^4$ cells/cm$^2$. The HDF are preferably postmitotic, but earlier passage cells can be used if they are irradiated, treated with mitomycin-C, or otherwise treated to inhibit their proliferation but maintain their metabolism (for example, by reduction of serum concentration).

Microporous membranes are suitable as a culture substrate because they allow substances to diffuse from one side to the other, but work as a barrier for cells. The pore size of the membrane should be adequate so as to allow diffusion of proteins of up to 100,000 Daltons molecular weight, and preferably of up to 70,000 Daltons molecular weight. The membrane should at least allow diffusion of small hormones such as insulin, and allow passage of proteins of up to 15,000 Daltons molecular weight. Other means than a microporous membrane for performing the function of allowing diffusion of soluble factors to the primary keratinocytes, while preventing mixing of the keratinocytes with the HDF can also be used.

Microporous membranes typical in the art can be used. However, membranes fabricated from a biodegradable material (e.g., polyhyaluronic acid or polylactic acid) can also be used. When a biodegradable microporous membrane is employed, the entire culture, including the differentiated keratinocytes, the microporous membrane and the HDF, can be transplanted into the skin defect. Thus, in this alternative embodiment, the HDF grown on the underside of the membrane need not be post-mitotic or treated to preclude proliferation. While HDF tend to be less immunogenic than keratinocytes, it is preferable that when this embodiment is employed, the HDF be allogeneic cells, preferably autologous cells. In some cases, the thickness of mesh graft can range from 30-300 microns.

In some examples, the mesh graft thickness ranges from 0.5-0.75 mm. A graft of tissue (for example, dermal collagen plus fibroblasts overlaid with keratinocytes tissue) that is too thick can result in a too rapid ischemic cell death, especially for the keratinocyte layer residing above the dermal fibroblast collagen layer. By contrast, this mesh graft tissue can take in wound sites.

To improve the stability of the organotypic tissue equivalents, a carrier membrane can be placed on top. As an adhesive, fibrin glue is can be used, or alternatives include extracellular matrix components such as collagen, fibronectin, proteoglycans (e.g., hyaluronic acid, chondroitin sulfate, and the like), or basement membrane zone components (e.g., laminin, Matrigel™, or L-polylysine), or similar tissue glues, may also be utilized.

The carriers used with the organotypic tissue equivalents can consist of a synthetic membrane, made from one or more of polyester, PTFE or polyurethane; from one or more biodegradable polymers (e.g., hyaluronic acid, polylactic acid or collagen); or a silicone or vaseline gauze dressing, or any other material suitable for wound dressing. These materials that are suitable for wound dressing allow the carrier to remain in place to immobilize the implanted tissue equivalents for several days, rather than requiring the carrier to be removed immediately after the tissue equivalents are transplanted. Thus, the carrier not only enhances stability and improves handling, but it also serves as a protective coat against physical damage as well as the proteolytic milieu and bacteria in the wound. Moreover, it serves for orientation of the graft.

The organotypic tissue equivalents can transplanted by simply placing them in the bed of the wound or other skin defect. The tissue equivalents are then immobilized. In some cases, the method for immobilization is by use of a biodegradable material, such as by using a tissue glue or adequate bandage.

VII. Rho Family Members and their Role in Cell Fate

Rho GTPase family proteins, which include Rho, Rac1 and Cdc42, control a wide variety of cellular processes, such as cell adhesion, motility, proliferation, differentiation and apoptosis (Etienne-Manneville and Hall, *Nature* 420:629-635, 2002; Hagerty et al., *J. Biol. Chem.* 282:4884-4893, 2007; Van Aelst and D'Souza-Schorey, *Genes Dev.* 11:2295-2322, 1997). One of the best characterized effectors of Rho is Rho-associated coiled-coil protein kinase (ROCK).

ROCK proteins are serine/threonine kinases that bind Rho. The catalytic kinase domain of ROCK, which comprises conserved motifs characteristic of serine/threonine kinases, is found at the N-terminus ROCK proteins also have a central coiled-coil domain, which includes a Rho-binding domain (RBD). The C-terminus is made up of a pleckstrin-homology (PH) domain with an internal cysteine-rich domain. The coiled-coil domain is thought to interact with other α-helical proteins. The RBD, located within the coiled-coil domain, interacts only with activated Rho GTPases, including RhoA, RhoB, and RhoC. The PH domain is thought to interact with lipid mediators such as arachidonic acid and sphingosylphosphorylcholine, and may play a role in protein localization. Interaction of the PH domain and RBD with the kinase domain results in an auto-inhibitory loop. In addition, the kinase domain is involved in binding to RhoE, which is a negative regulator of ROCK activity (Shi and Wei, *Arch. Immunol. Ther. Exp.* 55:61-75, 2007).

The ROCK family consists of two members, ROCK1 (also known as ROKβ or p160ROCK) and ROCK2 (also known as ROKα). ROCK1 (1354 amino acids; SEQ ID NO: 2) and ROCK2 (1388 amino acids; SEQ ID NO: 4) share 65% overall identity and 92% identity in the kinase domain.

Although both ROCK isoforms are ubiquitously expressed in tissues, they exhibit differing intensities in some tissues. For example, ROCK2 is more prevalent in brain and skeletal muscle, while ROCK1 is more abundant in liver, testes and kidney. Both isoforms are expressed in vascular smooth muscle and heart. In the resting state, both ROCK1 and ROCK2 are primarily cytosolic, but are translocated to the membrane upon Rho activation (Shi and Wei, Arch. *Immunol. Ther. Exp.* 55:61-75, 2007).

ROCK activity is regulated by several different mechanisms. As a result, Rho-dependent ROCK activation is highly cell-type dependent, ranging from changes in contractility, cell permeability, migration and proliferation to apoptosis. At least 20 ROCK substrates have been identified (Hu and Lee, *Expert Opin. Ther. Targets* 9:715-736, 2005; Loirand et al., *Cir. Res.* 98:322-334, 2006; Riento and Ridley, *Nat. Rev. Mol. Cell Biol.* 4:446-456, 2003), several of which are involved in apoptosis.

The role of ROCK in regulating apoptotic signaling is highly cell-type dependent and stimulus dependent. For example, several studies have demonstrated that Rho/ROCK activation is required for endothelial cell death elicited by cytokine or drug treatment. ROCK also appears to play a pro-apoptotic role in a number of other cell types, including primary thymocytes, embryonic fibroblasts and HeLa cells. In vivo, inhibition of ROCK results in protective effects in a variety of animal models. The protective effects of ROCK inhibition are often accompanied by a reduced inflammatory response (Shi and Wei, *Arch. Immunol. Ther. Exp.* 55:61-75, 2007).

In contrast, ROCK has also been associated with mediating cell-survival signals in vitro and in vivo. A ROCK-mediated pro-survival effect has been reported in epithelial cells, cancer cells and endothelial cells, as well as in other cell types. In airway epithelial cells, inhibition with Y-27632 or HA 1077 (also known as fasudil) induces membrane ruffling, loss of actin stress fibers and apoptosis (Moore et al., *Am. J. Respir. Cell Mol. Biol.* 30:379-387, 2004). Rho/ROCK activation also plays a pro-survival role during oxidative stress-induced intestinal epithelial cell injury (Song et al., *Am. J. Physiol. Cell Physiol.* 290:C1469-1476, 2006). ROCK has also been associated with pro-survival events in thyroid cancer cells (Zhong et al., *Endocrinology* 144:3852-3859, 2003), glioma cells (Rattan et al., *J. Neurosci. Res.* 83:243-255, 2006), human umbilical vein endothelial cells (Li et al., *J. Biol. Chem.* 277:15309-15316, 2002), hepatic stelate cells (Ikeda et al., *Am. J. Physiol. Gastrointest. Liver Physiol.* 285:G880-886, 2003) and human neuroblastoma cells (De Sarno et al., *Brain Res.* 1041:112-115, 2005). Evidence of ROCK playing a pro-survival role has also been reported in vivo, for example in vascular smooth muscle cells (Shibata et al., *Circulation* 103:284-289, 2001) and spinal motor neurons (Kobayashi et al., *J. Neurosci.* 24:3480-3488, 2004).

VIII. Rho-Associated Kinase (ROCK) Inhibitors

In one embodiment, the ROCK inhibitor is a small molecule. Exemplary small molecule ROCK inhibitors include Y-27632 (U.S. Pat. No. 4,997,834) and fasudil (also known as HA 1077; Asano et al., *J. Pharmacol. Exp. Ther.* 241:1033-1040, 1987). These inhibitors bind to the kinase domain to inhibit ROCK enzymatic activity. Other small molecules reported to specifically inhibit ROCK include H-1152 ((S)-(+)-2-Methyl-1-[(4-methyl-5-isoquinolinyl)sulfonyl] homopiperazine, Ikenoya et al., *J. Neurochem.* 81:9, 2002; Sasaki et al., *Pharmacol. Ther.* 93:225, 2002); N-(4-Pyridyl)-N'-(2,4,6-trichlorophenyl)urea (Takami et al., *Bioorg. Med. Chem.* 12:2115, 2004); and 3-(4-Pyridyl)-1H-indole (Yarrow et al., *Chem. Biol.* 12:385, 2005).

Additional small molecule Rho kinase inhibitors include those described in PCT Publication Nos. WO 03/059913, WO 03/064397, WO 05/003101, WO 04/112719, WO 03/062225 and WO 03/062227; U.S. Pat. Nos. 7,217,722 and 7,199,147; and U.S. Patent Application Publication Nos. 2003/0220357, 2006/0241127, 2005/0182040 and 2005/0197328.

In another embodiment, the ROCK inhibitor is a negative regulator of ROCK activity. Negative regulators of ROCK activation include small GTP-binding proteins such as Gem, RhoE, and Rad, which can attenuate ROCK activity. Autoinhibitory activity of ROCK has also been demonstrated upon interaction of the carboxyl terminus with the kinase domain to reduce kinase activity.

In another embodiment, the ROCK inhibitor can be an antibody that specifically binds ROCK1 or ROCK2 or both isoforms. In one example, the antibody specifically binds ROCK1 (SEQ ID NO: 2). In another example, the antibody specifically binds ROCK2 (SEQ ID NO: 4). By way of example and not limitation, an antibody specific for a ROCK protein can interfere with binding of ROCK to Rho or other binding partners, or the antibody can directly disrupt kinase activity of ROCK.

In another embodiment, the ROCK inhibitor is an antisense compound. Generally, the principle behind antisense technology is that an antisense compound hybridizes to a target nucleic acid and effects the modulation of gene expression activity, or function, such as transcription, translation or splicing. The modulation of gene expression can be achieved by, for example, target RNA degradation or occupancy-based inhibition. An example of modulation of target RNA function by degradation is RNase H-based degradation of the target RNA upon hybridization with a DNA-like antisense compound, such as an antisense oligonucleotide. Antisense oligonucleotides can also be used to modulate gene expression, such as splicing, by occupancy-based inhibition, such as by blocking access to splice sites.

Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. Another type of antisense compound that utilizes the RNAi pathway is a microRNA. MicroRNAs are naturally occurring RNAs involved in the regulation of gene expression. However, these compounds can be synthesized to regulate gene expression via the RNAi pathway. Similarly, shRNAs are RNA molecules that form a tight hairpin turn and can be used to silence gene expression via the RNAi pathway. The shRNA hairpin structure is cleaved by the cellular machinery into siRNA.

Other compounds that are often classified as antisense compounds are ribozymes. Ribozymes are catalytic RNA molecules that can bind to specific sites on other RNA molecules and catalyze the hydrolysis of phosphodiester bonds in the RNA molecules. Ribozymes modulate gene expression by direct cleavage of a target nucleic acid, such as a messenger RNA.

Each of the above-described antisense compounds provides sequence-specific target gene regulation. This sequence-specificity makes antisense compounds effective tools for the selective modulation of a target nucleic acid of interest. In one embodiment, the target nucleic acid is ROCK1 (SEQ ID NO: 1; Genbank Accession No. NM_005406). In another embodiment, the target nucleic acid is ROCK2 (SEQ ID NO: 3; Genbank Accession No. NM_004850). However, other known ROCK sequences can be used to design antisense compounds.

Methods of designing, preparing and using antisense compounds that specifically target ROCK are within the abilities of one of skill in the art. Examples of ROCK antisense oligonucleotides are described in U.S. Patent Application No. 2004/0115641.

Antisense compounds specifically targeting ROCK1 or ROCK2 can be prepared by designing compounds that are complementary to a ROCK1 or ROCK2 nucleotide sequence. Antisense compounds targeting ROCK1 or ROCK2 need not be 100% complementary to ROCK1 or ROCK2 to specifically hybridize and regulate expression of the target gene. For example, the antisense compound, or antisense strand of the compound if a double-stranded compound, can be at least 75%, at least 80%, at least 85%, at least 90%, at least 95%, at least 99% or 100% complementary to the selected ROCK1 or ROCK2 nucleic acid sequence. Methods of screening antisense compounds for specificity are well known in the art (see, for example, U.S. Patent Application No. 2003-0228689). Antisense compounds can contain one or more modifications to enhance nuclease resistance and/or increase activity of the compound. Modified antisense compounds include those comprising modified internucleoside linkages, modified sugar moieties and/or modified nucleosides.

The following examples are provided to illustrate certain particular features and/or embodiments. These examples should not be construed to limit the disclosure to the particular features or embodiments described.

EXAMPLES

Example 1

A ROCK Inhibitor Promotes Keratinocyte Proliferation and Differentiation Experimental Procedures Plasmids The HPV6 genome was cloned into the BamHI site of pBR322 (Schwarz et al., *EMBO J.* 2:2341-2348, 1983); the HPV11 genome was cloned into the pML2d plasmid (derivative of pBR322) (Dartmann et al., *Virology* 151: J 24-130, 1986); the HPV18 genome was cloned into the EcoRI site of pBR322 (Boshart et al., *EMBO J.* 3:1151-1157, 1984); and the HPV31 genome was cloned into the EcoRI site of pT713.

Cell Lines and Culture

Primary human foreskin keratinocytes (HFKs) were isolated and pooled from neonatal human foreskins from seven donors and grown in F medium (3: 1(v/v) F-12 Nutrient Mixture: DMEM, 5% FBS, 0.4 μg/ml hydrocortisone, 5 μg/ml insulin, 8.4 ng/ml cholera toxin, 10 ng/ml EGF, and 24 μg/ml adenine) (Jeon et al., *Proc. Natl. Acad. Sci. USA* 92:1654-1658, 1995) in the presence of irradiated J2 feeder cells. HFKs were divided into 10 cm plates, containing F-media with or without the addition of 10 μM Y-27632 (Alexis Biochemicals, San Diego, Calif.).

The 9E and W12 (20863 clone) cell lines were cultured in F-media on irradiated J2 feeder cells. For the Y-27632 experiments they were cultured in F-medium with or without 10 μM Y-27632 and continually passed for the times indicated.

Replication Assay

Cloned viral genomes were cleaved with restriction enzymes to separate viral and vector sequences. The genomes were religated at a concentration of 5 μg/ml to favor intramolecular circularization. Prior to electroporation, J2 feeder cells were removed from the keratinocytes by versene treatment and the HFKs were collected by trypsinization. HFKs ($1\times10^6$) were electroporated with 2 μg of re-circularized viral genomic DNA using the Amaxa Nucleofector II electroporator and the Human Keratinocyte Nucleofector Kit. The Amaxa program optimized for cell survival was used according to the manufacturer's specifications. Cells were removed from the cuvettes immediately following electroporation, and seeded onto 10 cm plates containing irradiated feeder cells and F-medium, in the presence or absence of 10 μM Y-27632, as indicated. At various times post-transfection, low molecular weight DNA was isolated by a modified Hirt extraction procedure (Ustav et al., *EMBO J.* 10:449-457, 1991). For Southern blot analysis, the isolated DNA was linearized with EcoRI or BamHI, depending on cloning site for each viral genome, and DpnI, to digest any unreplicated input DNA. DNA fragments were separated by agarose gel electrophoresis followed by Southern blot hybridization. A $^{32}$P-labeled probe was synthesized from the isolated viral genomic DNA (purified from the vector sequence) by the random prime method and used in Southern hybridizations.

Results

Figure 3:
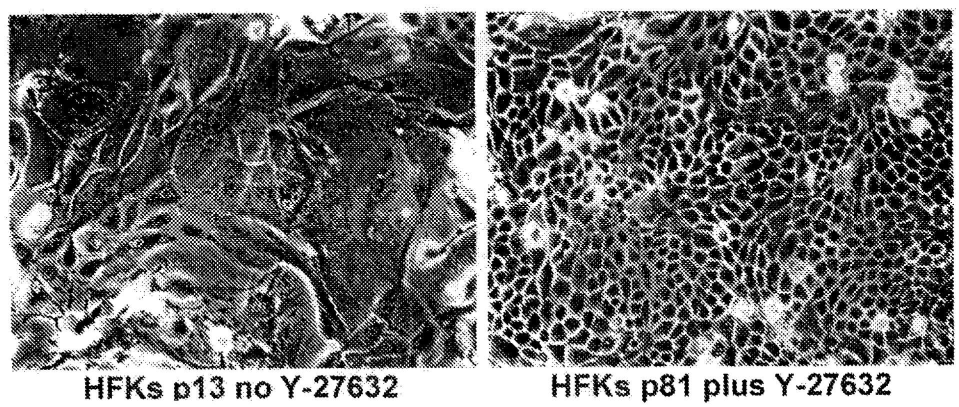
FIG. 3: Morphology of untreated human foreskin keratinocytes at p13 and Y-27632-treated cells at p81.
Figure 4:
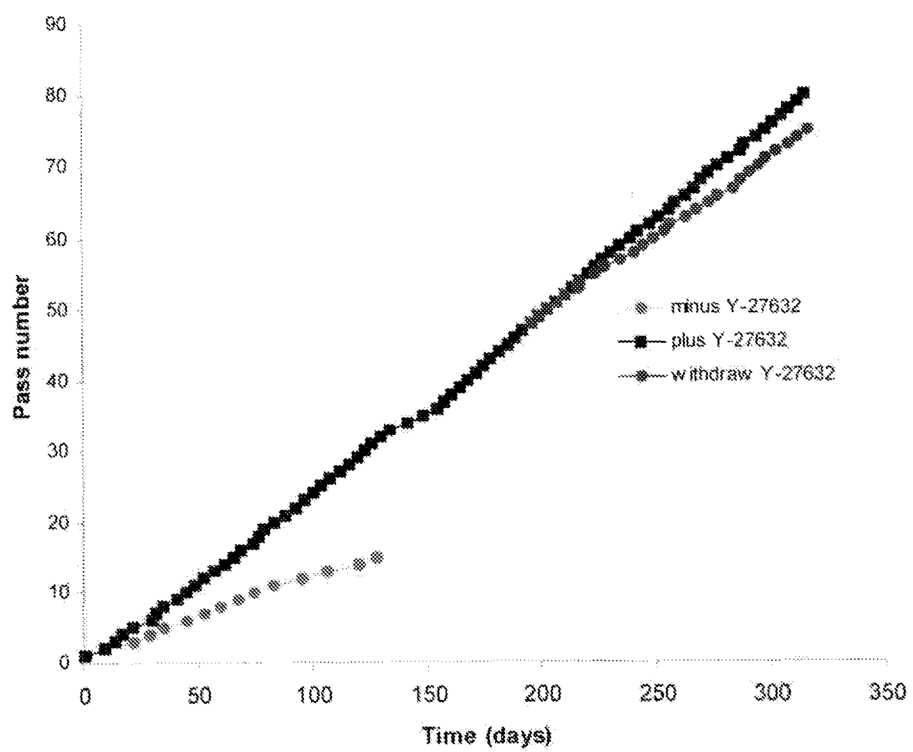
FIG. 4: Growth curves of primary human keratinocytes cultured in the presence or absence of 10 μM Y-27632. After 48 passages, Y-27632 was removed from the culture of treated cells and the resulting growth is indicated.

Inhibition of the Rho associated kinase ROCK by the inhibitor Y-27632 has been shown to increase survival of human embryonic stem cells (Watanabe et al., *Nature Biotechnology* 25:681-686, 2007) and to increase the colony forming ability of primary human foreskin keratinocytes. To determine whether inhibition of this pathway would increase the ability of keratinocytes to support HPV replication and the viral life-cycle, primary human foreskin keratinocytes were cultured in the presence or absence of 10 μM Y-27632. The treated cells proliferated at a rate that exceeded the untreated cells almost immediately. After about 15 passages (120 days in culture), the untreated cells ceased dividing and formed only abortive colonies containing flat cells that appeared senescent. The Y-27632-treated cells continued to divide without any decrease in growth rate. The treated cells were small and cuboidal and grew in closely packed colonies characteristic of basal cells (see FIG. 3). The cells were passed at least 82 times and were in continuous culture for over 10 months. Thus, they can be considered immortal. The growth curves of these cells are shown in FIG. 4. To determine whether the continuous presence of Y-27632 was required for this immortalized state, Y-27632 treatment was withdrawn at passage 48 (p48), after 196 days in culture. These cells continued to grow unchecked with only a gradual slowing in the rate of population doubling.

Figure 5:
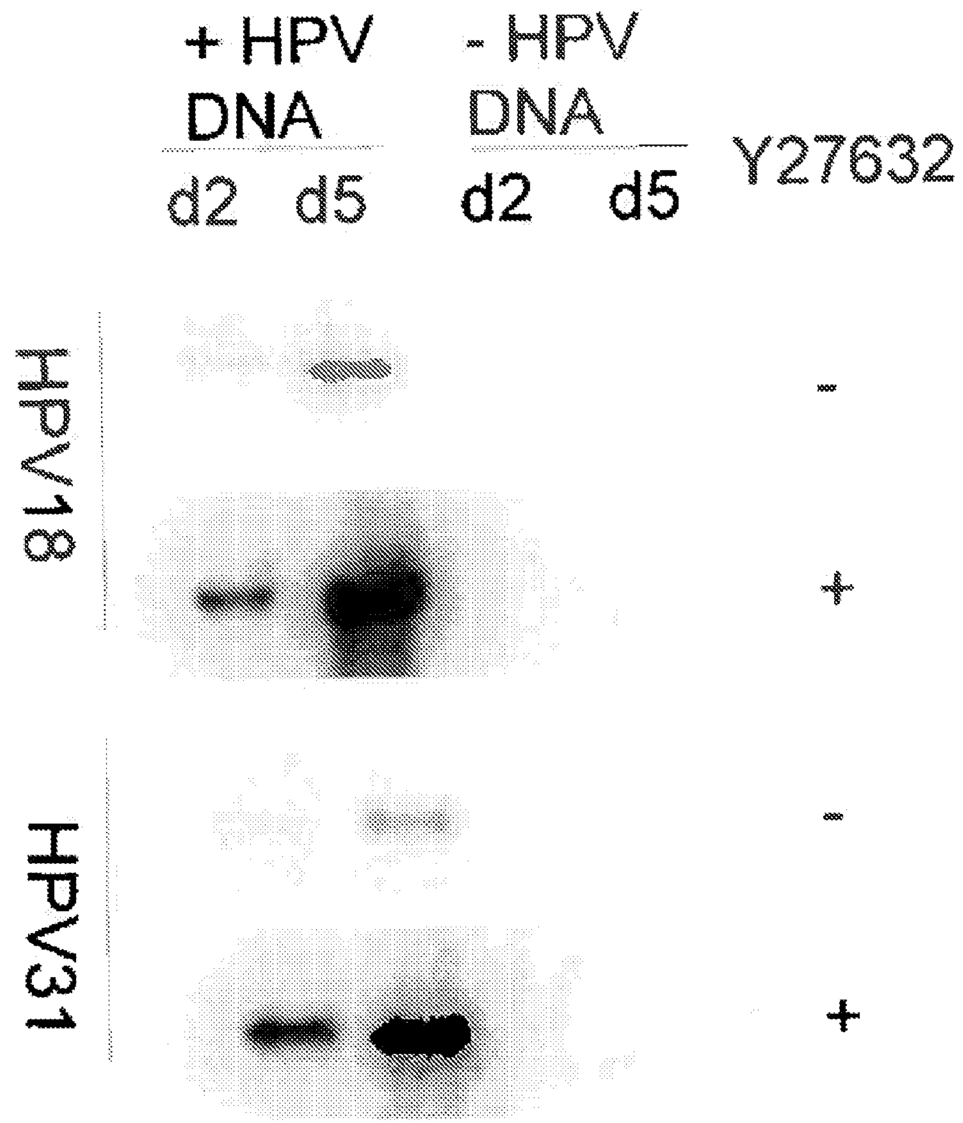
FIG. 5: Replication of HPV18 and HPV31 viral genomes in the presence of 10 μm Y-27632 at two days and five days post-transfection.

To determine whether the greatly improved culture conditions of the primary human keratinocytes would benefit HPV DNA replication, viral genomes from the "high-risk" viruses HPV18 and HPV31 were transfected into early passage primary foreskin keratinocytes using nucleofection. Transfected cultures were maintained in the presence or absence of Y-276328 and low molecular weight extrachromosomal DNA was isolated at two days and five days post-electroporation. The isolated DNA was cleaved with a restriction enzyme that linearized the viral genome and with DpnI which will only cleave unreplicated input DNA that harbors methylation from propagation in bacteria. The levels of replicated DNA were further analyzed by Southern blot analysis. As shown in FIG. 5, treatment with Y-27632 greatly increased the efficiency of HPV replication up to five days.

The great increase in efficiency of "high-risk" HPV DNA replication in the presence of Y-27632 prompted examination of the replication of "low-risk" HPV6. Replication assays are much more difficult with the low risk viruses because the E6 and E7 viral proteins do not provide the cells with a selective growth advantage. FIG. 6 shows a replication experiment with the "low risk" HPV6 and the "high-risk" HPV18 viral genomes. Both genomes were electroporated into primary human keratinocytes and were passed in the presence or absence of Y-27632 for up to 12 passages. In the absence of Y-27632, the keratinocytes containing HPV6 DNA had only reached passage 4 by day 49 after electroporation. The viral DNA was detectable at days five and ten but by the next pass, at day 32, was undetectable. Treatment with Y-27632 greatly increased the efficiency of replication and robust levels of viral DNA were present after three passes. After this, however, the levels of viral DNA declined. This is likely because there is no selective advantage to having the viral genome present. Co-transfection of "low risk" HPV DNA with a drug selectable marker in addition to Y-27632 treatment should enable maintenance of the viral genome for much greater time periods. At early times, replication of the "high risk" HPV18 was greater in the presence of Y-27632 (FIGS. 5 and 6). However, after day 10 there appeared to be greater levels of replication in the absence of Y-27632. HPV18 expresses oncogenic E6 and E7 proteins that give the cells a selective growth advantage. It is most likely that inhibition of the Rho kinase pathway by Y-27632 has negated the selective growth advantage conferred by the "high-risk" E6 and E7 oncoproteins. Again, co-transfection with a drug-selectable marker should increase apparent replication levels by selecting for the transfected cells. It has been reported that HPV replication of "high risk" HPVs requires E6 and E7 functions (Park et al., *J. Virol.* 76: 11359-11364, 2002; Thomas et al., *Proc. Natl. Acad, Sci. USA* 96:8449-8454, 1999). It will be of interest to determine whether these functions are required in the presence of Y-27632.

Figure 7:
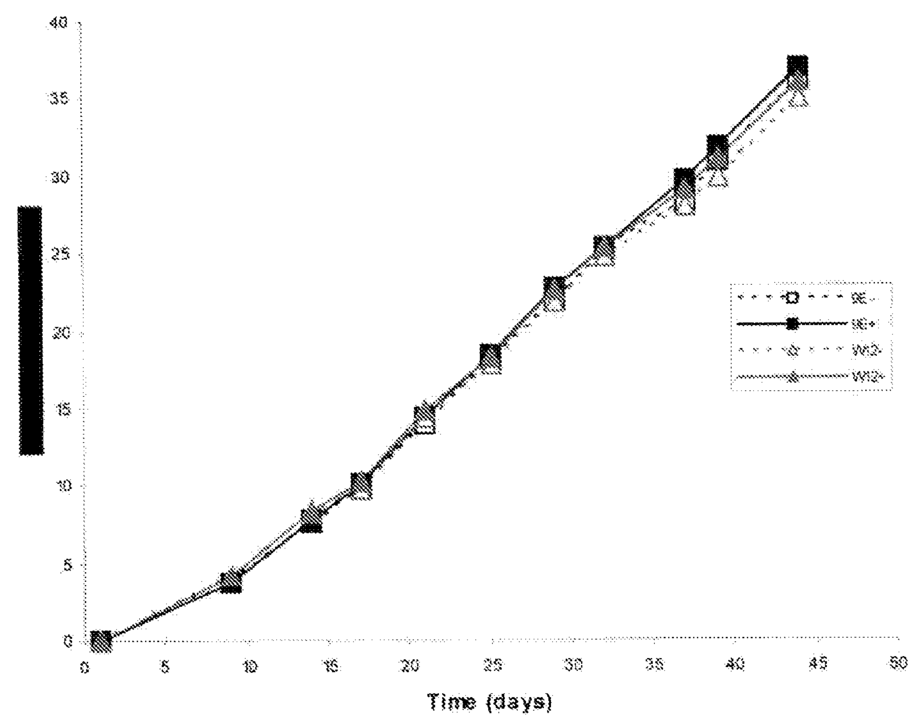
FIG. 7: Growth curves of the immortalized CIN1 patient derived cell lines, W12 and CIN612 9E, containing extrachromosomally replicating HPV DNA in the presence or absence of 10 μM Y-27632.
Figure 8:
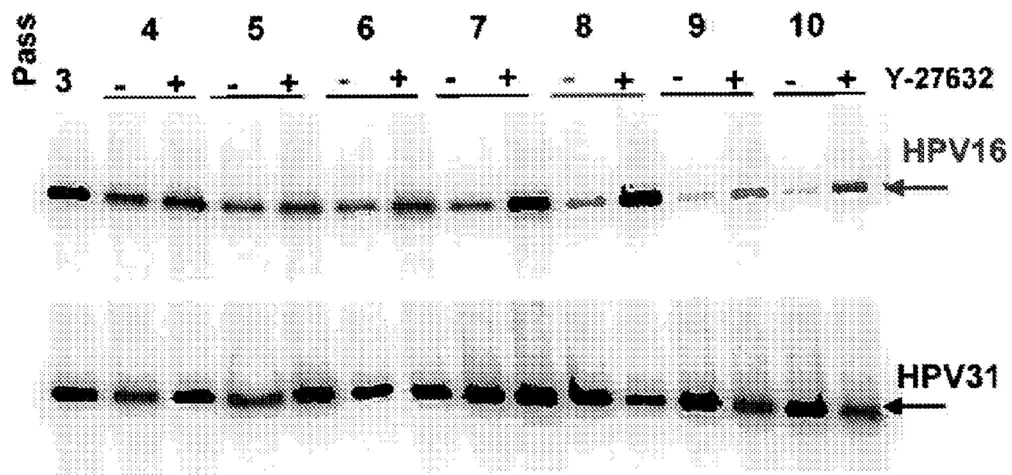
FIG. 8: Effect of 10 μM Y-27632 treatment on the genome copy number of HPV16 in the CIN1-derived line W12, and of HPV31 in the CIN1-derived line CIN612 9E.

Only two cell lines that harbor extrachromosomally replicating HPV DNA have been successfully cultured from patients with early dysplastic cervical lesions. W12 cells (Stanley et al., *Int. J. Cancer* 43:672-676, 1989) and CIN612 9E cells (Rader et al., *Oncogene* 5:571-576, 1990) were isolated from CIN1 lesions containing HPV16 and HPV31, respectively. Both CIN612 9E cells and the 20863 clone (Jeon et al., *J. Virol.* 69:2989-2997, 1995) of W12 cells were cultured in the presence or absence of Y-27632 for 44 days (approximately 35 population doublings) to determine any effects on cell growth and HPV replication levels. As shown in FIG. 7, no differences in growth rate were observed in either cell line in the presence of Y-27632. Low molecular weight DNA was isolated and analyzed for HPV DNA at various time points. As shown in FIG. 8, Y-27632 had somewhat different effects on each cell line. The HPV31 copy number remained constant in the 9E cells, showing that Y-27632 had no direct effect on HPV replication. The copy number of HPV16 declined gradually in the W12 cells, both in the presence and absence of Y-27632. This is likely explained by the previous observation that extrachromosomal maintenance of the viral genome in W12 cells is somewhat unstable and the genomes have the propensity to integrate upon prolonged culture, giving the cells with integrated genomes a selected growth advantage (Jeon et al., *J. Virol.* 69:2989-2997, 1995). Y-27632 partially rescued the decline in copy number and this is likely due to removing the selective advantage provided by integration of the viral genome.

Example 2

Immortalization of Human Keratinocytes Using a Rock Inhibitor

Materials and Methods

Cell Culture

Human foreskin keratinocytes (HFKs) were isolated from pools of at least seven neonatal foreskins and grown in 154 medium supplemented with Human Keratinocyte Growth Supplement and Gentamicin/Amphotericin (Invitrogen, Carlsbad, Calif.) or in F medium [3:1 (v/v) F-12 (Ham)-DMEM, 5% FBS, 0.4 μg/ml hydrocortisone, 5 μg/ml insulin, 8.4 ng/ml cholera toxin, 10 ng/ml EGF, 24 μg/ml adenine, 100 U penicillin, 100 μg/ml streptomycin (Invitrogen, cat no. 15140-148)] in the presence of irradiated 3T3 J2 feeder cells (Jeon et al., *J. Virol.* 69: 2989-2997, 1995).

The HPV18 cell line was established by introducing the HPV18 genome into primary HFKs using the Amaxa human keratinocyte nucleofection system. Primary human cervical keratinocytes (HCKs), human vaginal keratinocytes (HVKs), the HPV18 cell lines and the HPV31 positive cell line (CIN-612 9E) were grown in the presence or absence of 10 μM Y-27632 (Alexis Biochemicals), as indicated. Cells were subcultured by removing the fibroblast feeder cells with versene and keratinocytes were collected by trypsinization. At each pass, $2\times10^5$ cells were plated on a 10 cm plate of J2 feeder cells. Population doubling was calculated as:

$$PD=3.32(\log(\#\text{ cells harvested}/\#\text{ cells seeded})).$$

Immunodetection

Proteins were extracted in 2% sodium dodecyl sulfate (SDS), 50 mM Tris-HCl (pH 6.8), 10% glycerol supplemented with inhibitors Complete and PhosphoSTOP (Roche, Indianapolis, Ind.). Protein samples were resolved on NuPage gels, electrotransferred to Immobilon-P membrane (Millipore, Billerica, Mass.), and probed with the relevant antibodies before detection by chemiluminescence. Monoclonal antibody against p53 (DO-1) was obtained from Santa Cruz Biotechnology (Santa Cruz, Calif.). Monoclonal antibody against α-tubulin (B-5-1-2) was obtained from Sigma-Aldrich. Polyclonal antibodies against Myc (N-262), p21 (C-19), and p16 (C-20) were obtained from Santa Cruz Biotechnology.

Real Time QRT-PCR

Total cellular RNA was isolated with TRIZol™ reagent (Invitrogen, Carlsbad, Calif.) and treated with DNA-free kit (Ambion, Austin, Tex.). First-strand cDNA was synthesized from 8 μg of total cellular RNA using the Superscript III First-Strand Synthesis System (Invitrogen, Carlsbad, Calif.). RNase H-treated cDNA from 20 ng RNA was amplified by quantitative real time PCR using the Taqman Gene Expression Assay for hTERT (Assay ID: Hs00972646_m1, Applied Biosystems) spanning exons 14 and 15 and human RPLP0 (large ribosomal protein) endogenous control, VIC/MGB Probe, primer limited (Applied Biosystems). All samples were run in triplicate using the ABI 7900HT system and the amount of product was calculated with reference to standard curves generated by 4-fold serial dilutions of a mixed set of cDNAs with high telomerase expression. Values were adjusted relative to the level of RPO transcripts.

Telomere Length Assay

Genomic DNA was extracted from cells and the average telomere length was assessed by a modified method of the real-time PCR-based telomere assay described previously (Cawthon et al., *Nucleic Acids Res.* 30: e47, 2002; Cawthon, *Nucleic Acids Res.* 37: e21, 2009). Briefly, the telomere repeat copy number to single gene copy number (T/S) ratio was determined using a Bio-Rad IQ5 thermocycler. Genomic DNA (5 ng) was subjected to PCR reactions and detected with SYBR Green Super Mix (Bio-Rad). The primers for telomere length and HBG1 (a single copy gene) were as follows.

```
                                            (SEQ ID NO: 5)
Tel-1:   CGGTTTGTTTGGGTTTGGGTTTGGGTTTGGGTTTGGGTT

                                            (SEQ ID NO: 6)
Tel-2:   GGCTTGCCTTACCCTTACCCTTACCCTTACCCTTACCCT

                                            (SEQ ID NO: 7)
HBG1:    TGTGCTGGCCCATCACTTTG

                                            (SEQ ID NO: 8)
HBG2:    ACCAGCCACCACTTTCTGATAGG
```

Reaction conditions were: 1 cycle, 95° C., 5 minutes; 41 cycles, 95° C., 15 seconds,; 1 cycle, 60° C. for 45 seconds. All reactions were carried out in triplicate and compared to a standard curve of 0, 0.2, 1, 5, 25 and 125 ng genomic DNA (telomere length 10.4 kb) from Roche Telo-kit. The T/S ratio (dCt) for each sample was calculated by normalizing the average HBG Ct value to the average telomere Ct value.

Karyotype Analysis

This was conducted by Molecular Diagnostic Services, Inc. San Diego, Calif. Metaphase spreads were prepared and stained to observe chromosomal G bands.

Twenty metaphase spreads of each cell line was analyzed and five complete karyotypes were prepared from each.

DNA Genotype Analysis

Cellular DNAs were analyzed using the PowerPlex 1.2 STR genotyping kit (Promega) by Molecular Diagnostic Services, Inc., San Diego, Calif.

Organotypic Raft Culture

Organotypic cultures were generated as described previously with modifications. (Banerjee et al., *Methods Mol. Med.* 119: 187-202, 2005). Briefly, $1\times10^5$ keratinocytes were seeded onto a rat tail type 1 collagen dermal equivalent containing $1-2\times10^6$ J2 3T3 feeder cells. The rafts were lifted onto stainless steel grids and were fed by diffusion from below with raft medium [3:1 (v/v) DMEM-F-12 (Ham), 10% FBS, 0.4 μg/ml hydrocortisone, 0.1 nM cholera toxin, and 5 μg/ml transferring]. Raft cultures were allowed to stratify and differentiate for 11-17 days. The collagen-epithelial rafts were fixed in formalin for 4 hours, paraffin embedded, sectioned and stained with hematoxylin and eosin (H&E) or by immunofluorescence as described in Pei et al. (*Methods Mol. Med.* 119: 49-59, 2005). Monoclonal antibody against anti-keratin 14 (K14) (Ab-1) was from Thermo Fisher Scientific, Fremont, Calif. Goat polyclonal antiserum against Filaggrin (N-20) and rabbit polyclonal antiserum against involucrin (H-120) were from Santa Cruz Biotechnology.

Growth Arrest Assay

Keratinocytes (1-2×$10^6$) were seeded on a 10 cm plate. Forty-eight hours later they were treated with 0.5 nM actinomycin D for 24 hours. Protein extracts were prepared, as described above, and analyzed for p53 and p21 protein levels.

Results

Y-27632 Immortalizes Primary Human Keratinocytes

Figure 9:
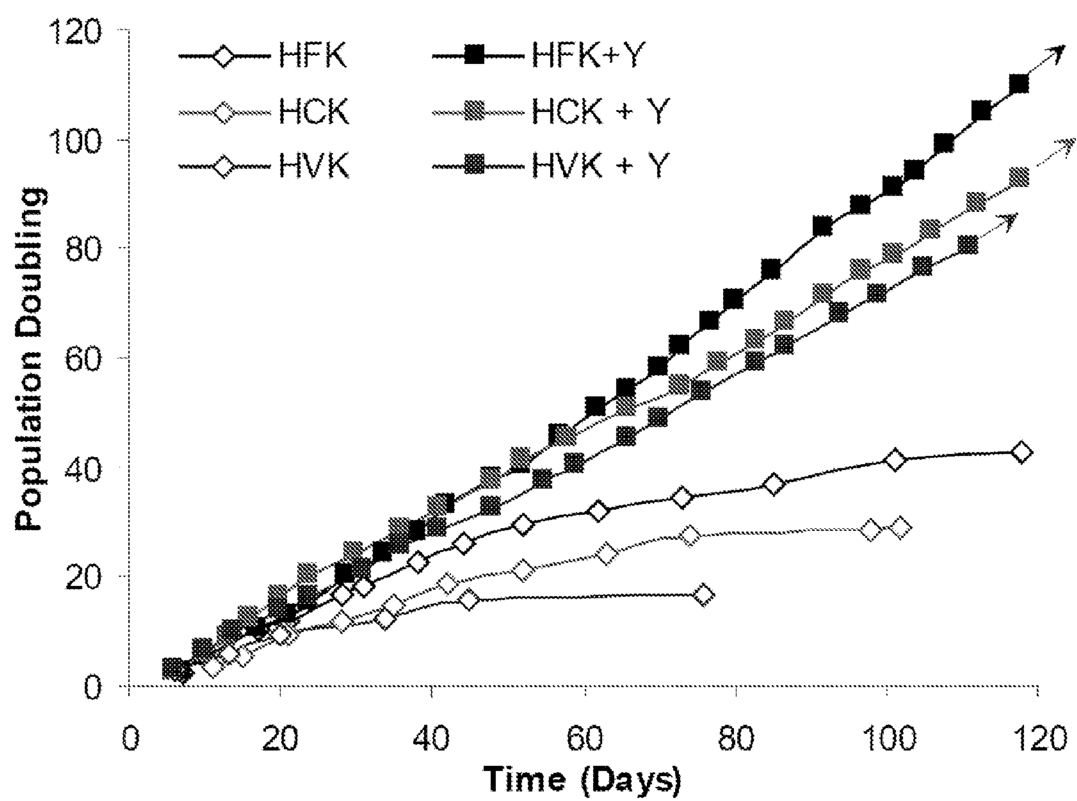
FIG. 9: Y-27632 stabilizes the growth rate of primary keratinocytes. Shown is the growth rate of human keratinocytes from foreskin (HFK strain c), ectocervix (HCK) and vaginal tissue (HVK) cultured in the presence (solid squares) or absence (open diamonds) of 10 μM Y-27634. The arrows indicate that these cells lines continued to divide indefinitely. Growth rate is measured as population doubling time.
Figure 14:
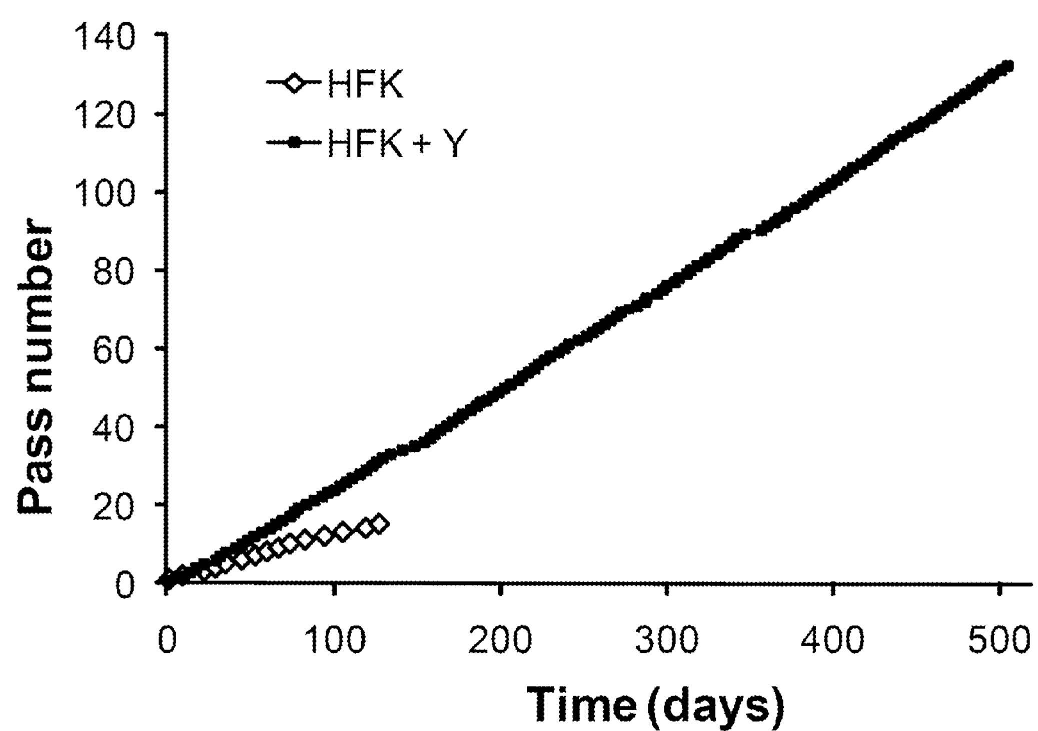
FIG. 14: Treatment with Y-27632 immortalizes primary keratinocytes. Human foreskin keratinocytes (HFK strain a) were cultured in the presence (solid squares) or absence (open diamonds) of 10 μM Y-27632. Cells were passed when confluent and split at a ratio 1:10, with a few exceptions when cells were split 1:20.

Rho kinase inhibition has been reported to affect keratinocyte proliferation and differentiation (Terunuma et al., *Tissue Eng Part A*, Nov. 15, 2009 [Epub]; McMullan et al., *Current Biology* 13: 2185-2189, 2003). To further explore the effect of Rho kinase inhibition on the long term growth of keratinocytes, human neonatal foreskin keratinocytes and adult vaginal and ectocervical keratinocytes were cultured in the presence or absence of 10 μM Y-27632, a well-characterized inhibitor of the Rho-associated kinase, ROCK. As shown in FIG. 9, the growth rate of all three keratinocyte types slowed with time and senescence was observed at approximately population doubling 20-40, depending on the specific cell type. In the presence of Y-27632, a dramatic increase in cellular proliferation of all three types of keratinocytes was observed within days and continued indefinitely. Y-27632-treated cells had a constant and steady growth rate, as indicated by the constant slope of population doublings against time. All three types of keratinocytes efficiently bypassed senescence with no observed decline in growth rate. As shown in Table 1, efficient keratinocyte immortalization was observed at least eight times with three different donor pools of foreskin keratinocytes (strains a, b, and c) and twice each with ectocervical and vaginal keratinocytes. Foreskin keratinocytes have been cultured for up to 150 passages for a period of 500 days and can be considered immortal (see FIG. 14). Occasionally, spontaneously immortalized cells grew out from quiescent cells that were close to senescence in the absence of Y-27632, but this only occurred after a long lag period suggesting that individual cells had picked up rare mutations allowing them to escape senescence. In contrast, Y-27632-treated cells grew steadily at all times.

TABLE 1

Keratinocyte immortalization in the presence and absence of Y-27632

| Keratinocyte strain | | +Y-27632[1] | −Y-27632[2] |
|---|---|---|---|
| HFK | a | PD195 | PD62 |
| | | PD193 | PD51 |
| | | PD177 | PD42 |
| | | PD183 | PD29 |
| | | PD145 | PD29 |
| | b | PD199 | PD34 |
| | c | PD150 | PD69 |
| | | PD105 | PD41 |
| HCK | | PD93 | PD28 |
| | | PD67 | PD22 |
| HVK | | PD80 | PD17 |
| | | PD66 | PD15 |

[1]Cells were cultured to the population doubling (PD) shown and were considered to be immortal.
[2]Cells were determined to be senescent at the population doubling shown. Senescence was defined as growth rate (population doubling/day) less than or equal to 0.2 within the time period of one month.
HFK: human foreskin keratinocyte;
HCK: human cervical keratinocytes;
HVK: human vaginal keratinocyte Genetic analysis was carried out on two of the immortalized foreskin keratinocyte strains (a and b) to ensure that they were identical to the original donor cells. Short tandem repeat analysis, a method used to distinguish individuals based on the highly polymorphic nature of certain regions of chromosomes, showed that the immortalized cells were genetically indistinguishable from the original keratinocytes, eliminating the possibility of contamination by an immortalized cell line.

Immortalization by Y-27632 is Dependent on Co-culture with Fibroblasts

Culturing keratinocytes in the presence of fibroblast feeder cells increases the lifespan of keratinocytes (Fu et al., *Cancer Res.* 63: 7815-7824, 2003; Rheinwald et al., *Mol. Cell Biol.* 22: 5157-5172, 2002) and might contribute to the observed immortalization by Y-27632. Therefore, the effect of Y-27632 on foreskin keratinocytes grown in the absence of fibroblast feeder cells, cultured on plastic and in serum-free medium was analyzed. Y-27632 treatment resulted in somewhat increased proliferation but this was not as pronounced as in the presence of feeders. Furthermore, in repeated experiments, these cells did not bypass senescence. Therefore, co-culture with feeder fibroblasts is required in concert with ROCK inhibition to immortalize keratinocytes.

Figure 10:
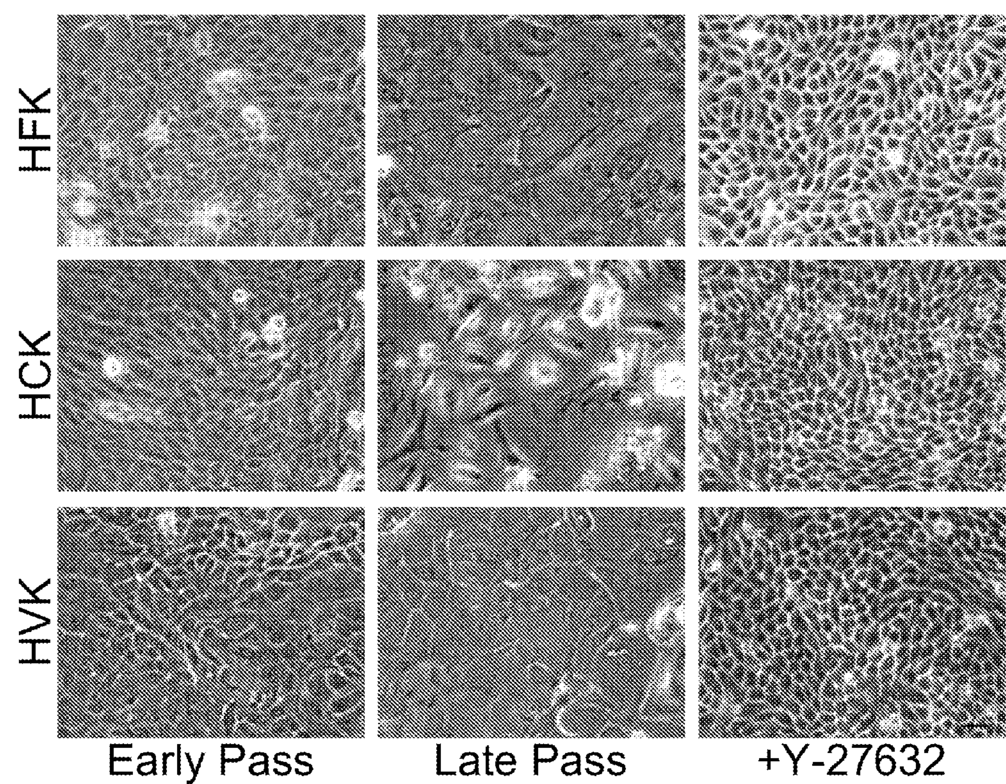
FIG. 10: Morphology of Y-27632-immortalized cells resembles early pass primary keratinocytes. The left column shows images of human foreskin keratinocytes (HFK), ectocervical keratinocytes (HCK), and vaginal keratinocytes (HVK) at pass P1. The middle column shows keratinocytes near senescence (HFK P15, HCK P9 and HVK P5). The right column shows keratinocytes immortalized by 10 μM Y-27632 (HFK P100, HCK P29 and HVK P26). Scale bar, 10 μm.

Morphology of Y-27632 Immortalized Keratinocytes Resembles Early Passage, Basal-like Keratinocytes At early passages, primary keratinocytes are actively dividing and are small, cuboidal and homogeneous in shape (FIG. 10). When cultured with fibroblast feeder cells, they grow in tightly packed colonies and resemble basal keratinocytes. As they approach senescence, their morphology changes and they becomes flat, and heterogeneous with enlarged cytoplasmic volume. The morphology of the Y-27632 immortalized cells was similar to early passage keratinocytes and is typical of actively dividing cells.

The Karyotype of Y-27632 Immortalized Cells is Normal

Immortalization of primary human keratinocytes is rare and the resulting cell lines have genetic changes and abnormal karyotypes. The karyotype was analyzed for one of the foreskin keratinocyte lines (strain a) that had been cultured in the presence of Y-27632 for 95 passages. The karyotype of the immortalized cells was identical to that of the donor cells with the correct number of chromosomes with no apparent abnormalities.

Telomerase is Upregulated in Y-27632-immortalized Cells

Figure 11A:
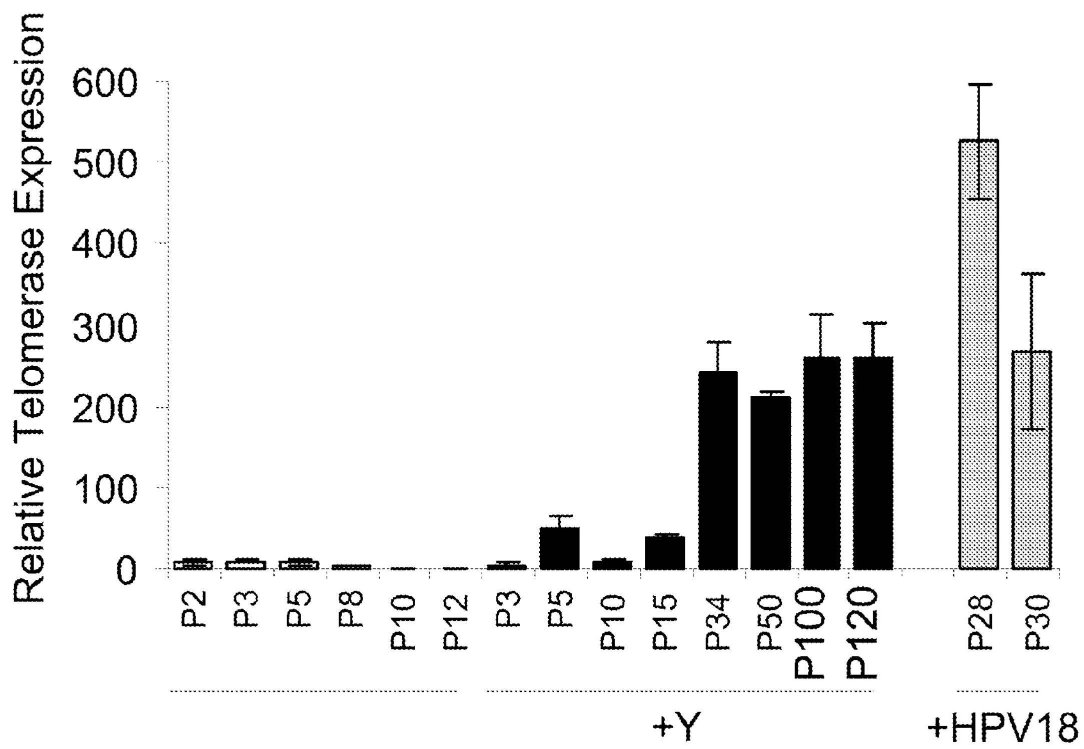
FIG. 11A is a graph showing the relative levels of hTERT mRNA from HFK strain a, cultured in the absence or presence of 10 μM Y-27632, at the pass indicated, as quantitated by real-time PCR.
Figure 15:
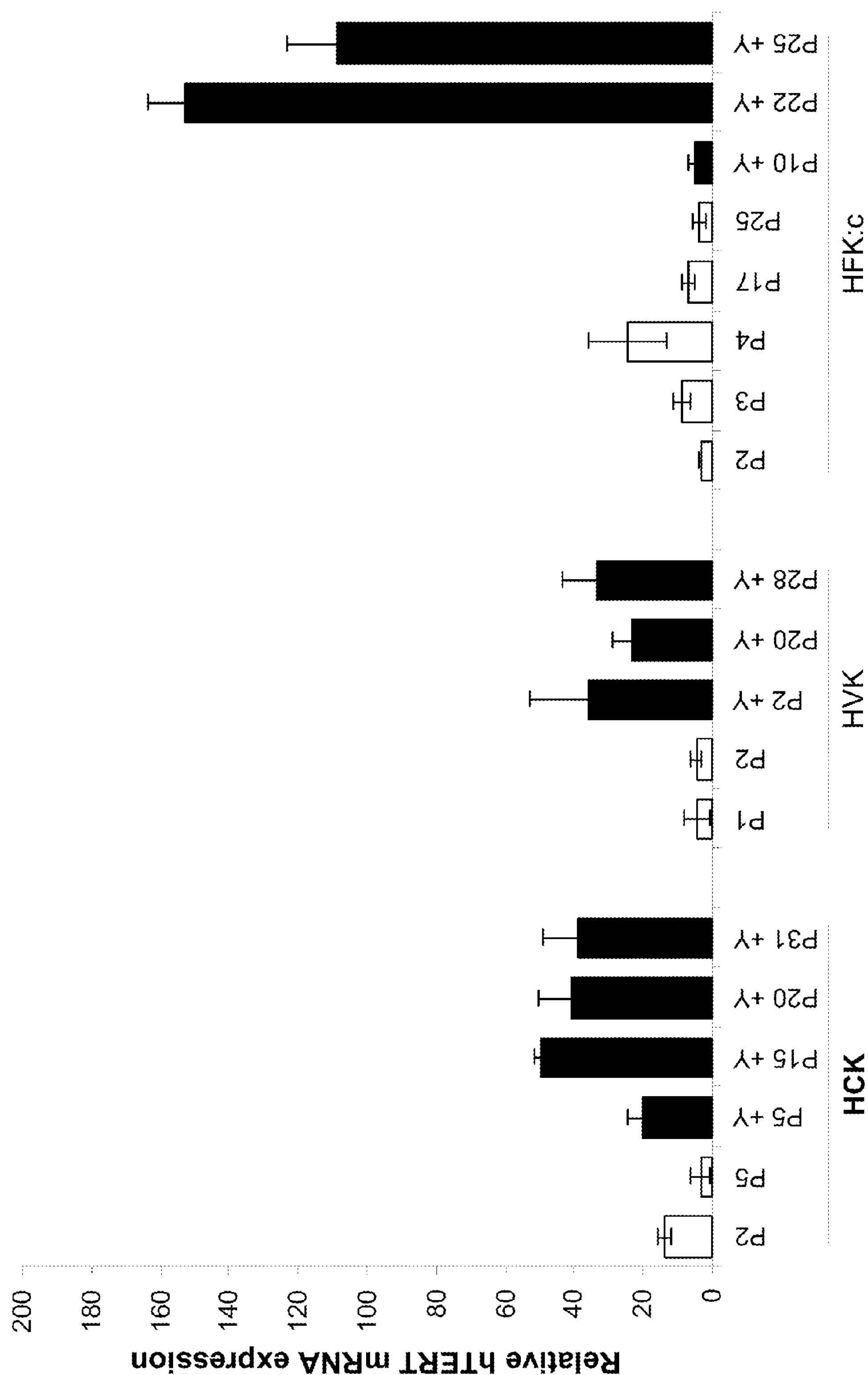
FIG. 15: Telomerase expression in Y-27632-treated cells increases with passage. Relative levels of hTERT mRNA in HFK strain c, HCK and HVK cells cultured in the absence or presence of Y-27632, as quantitated by real-time PCR.

Human telomerase verse transcriptase (hTERT) is a subunit of telomerase, which maintains the telomere caps throughout the multiple cell divisions of development. hTERT expression is turned off in most somatic cells and so the telomere ends become progressively shorter over multiple cell divisions. Replicative senescence is triggered when these protective ends become critically short (Harley et al, *Nature* 345: 458-460, 1990). To overcome this constraint, most tumor-derived or immortal cell lines have reactivated hTERT expression to maintain the telomere ends. Quantitative RT-PCR analysis showed that the level of hTERT mRNA increased with passage of foreskin keratinocytes in the presence of Y-27632 (FIG. 11A). As a comparison, hTERT mRNA levels were also determined in keratinocytes immortalized with HPV18. The "high risk" HPV E6 protein directly upregulates hTERT transcription as part of the immortalization process (Klingelhutz et al., *Nature* 380: 79-82, 1996). By passage 34 in Y-27632, hTERT mRNA levels were comparable to those in HPV18-immortalized keratinocytes. A similar induction of hTERT mRNA was observed in vaginal and cervical keratinocytes immortalized by Y-27632, as well as in another strain of foreskin keratinocytes (FIG. 15).

The Lengths of Telomeres Shorten, but are Stabilized, in Keratinocytes Immortalized by Y-27632

Figure 11B:
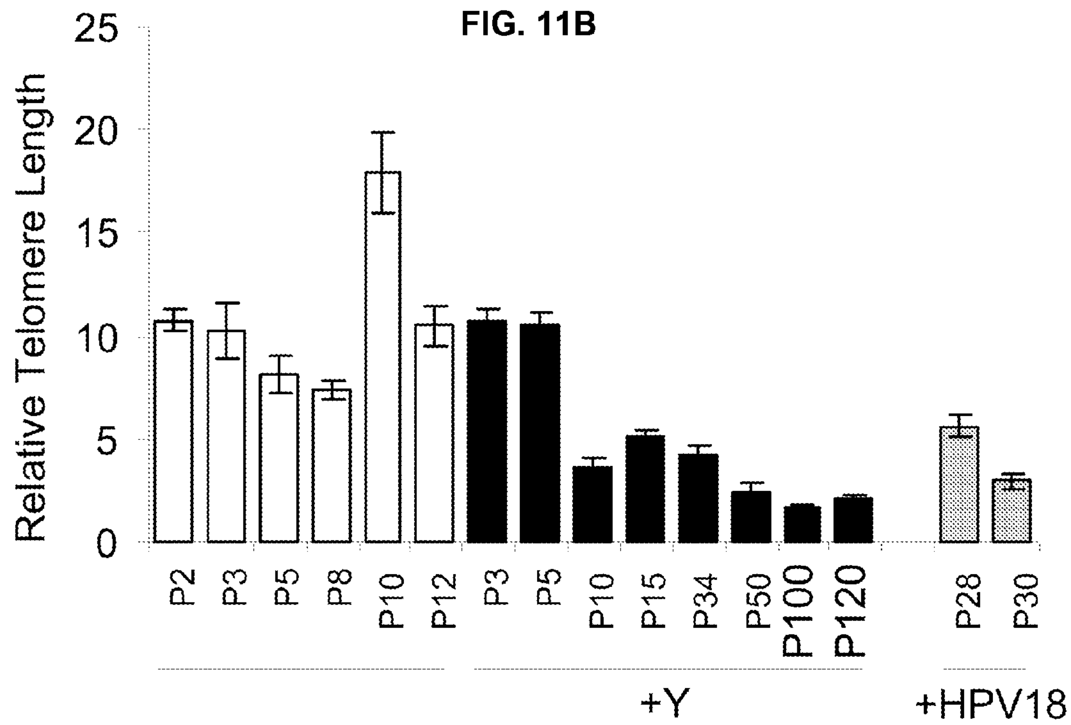
FIG. 11B is a graph showing the relative length of telomeres in HFK strain a cultured in the absence or presence of 10 μM Y-27632, at the pass indicated, as quantitated by real-time PCR.

In HPV immortalized cells, telomere ends erode despite telomerase induction, but the shortened length becomes stable (Stoppler et al., *J. Biol. Chem.* 272: 13332-13337, 1997). A similar phenomenon was observed in Y-27632 immortalized cells. The relative length of telomeres was measured using a quantitative PCR assay. Despite increased levels of telomerase expression, the length of the telomeres in cells cultured with Y-27632 became progressively shorter with passage (FIG. 11B). However, the length became stable from passage 50 to 120 and was similar to the length of telomeres in HPV18 immortalized cells.

P16$^{INK4a}$ is Expressed in Y-27632-immortalized Cells

Unlike the situation for fibroblasts, telomerase expression is not sufficient for immortalization of human keratinocytes and the pRB/p16$^{INK4a}$ pathway must also be inactivated (Dickson et al., *Mol. Cell Biol.* 20: 1436-1447, 2000). p16$^{INK4a}$ mRNA and protein levels were examined in keratinocytes during long term culture with Y-27632. p16$^{INK4a}$ mRNA and protein expression were still observed, albeit at a low level, after long-term culture with Y-27632 (see FIG. 12A). However, at this point it is unknown whether the observed p16$^{INK4a}$ is functional. In contrast, the level of p16$^{INK4a}$ in HPV immortalized cells is very high, but non-functional because of inactivation of the pRb pathway. Y-27632 treatment had no effect on the p16$^{INK4a}$ levels in these cells.

c-Myc is Upregulated in Y-27632-immortalized Cells

Figure 12A:
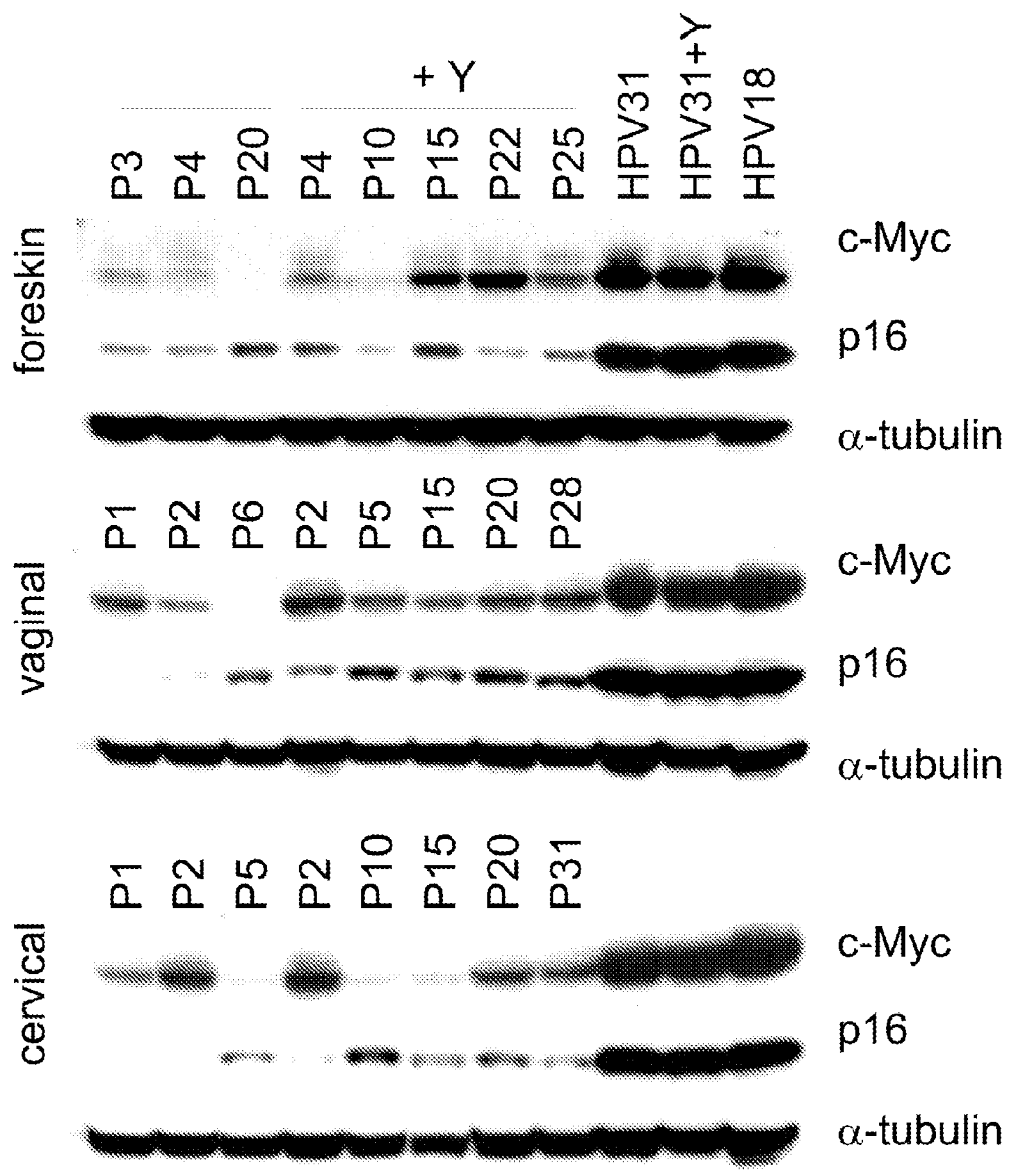
FIG. 12A shows an immunoblot analysis of Myc and p16 proteins in cells cultured in HFK strain c, HVK, and HCK cells in the absence or presence of 10 μM Y-27632, collected at the pass indicated. Cells containing oncogenic HPV31 and HPV18 viruses are included as controls. α-tubulin is included as a loading control.
Figure 16:
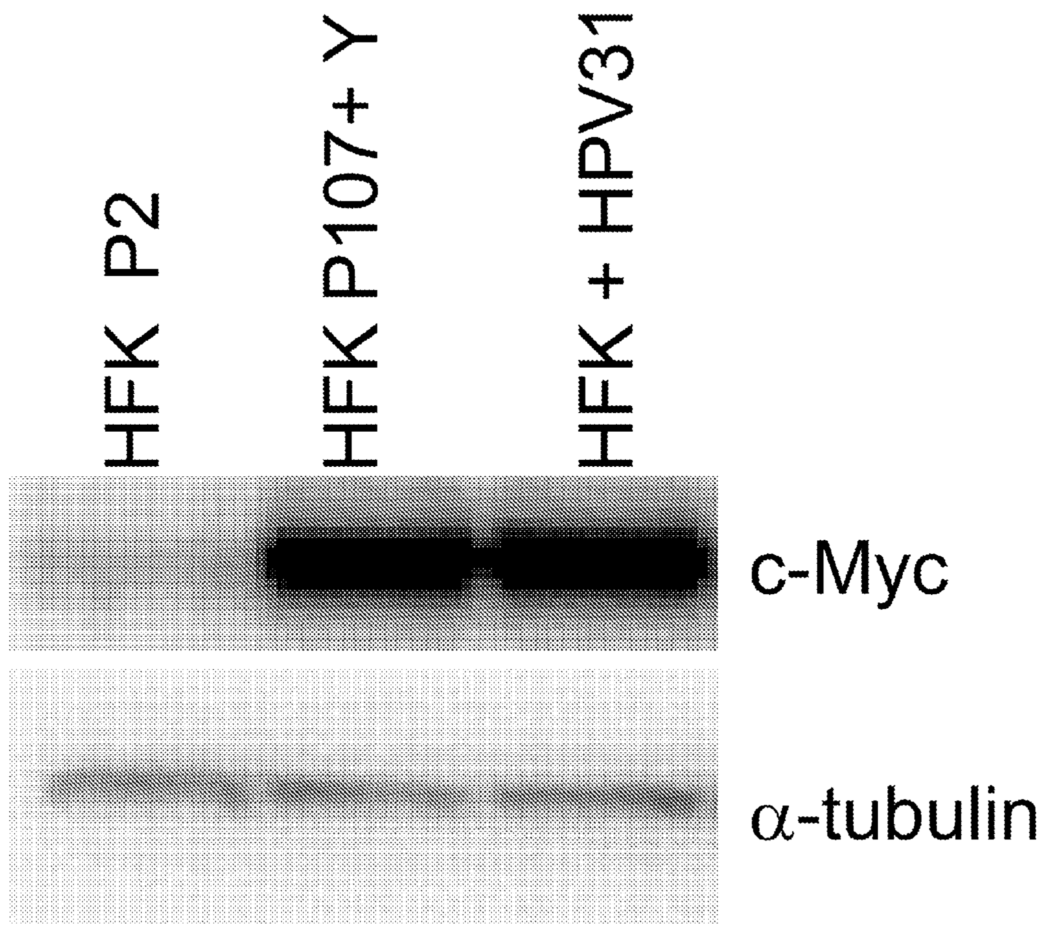
FIG. 16: Expression level of Myc is upregulated in Y-27632 immortalized cells at a late passage. Shown is an immunoblot analysis of Myc protein in HFK strain a P2 or after 107 passages in 10 μM Y-27632. Cells containing the oncogenic HPV31 are included as a comparison. α-tubulin is included as a loading control.

The Myc protein binds to the E-boxes of the hTERT promoter to induce transcription (Wang et al., *Genes Dev.* 12: 1769-1774, 1998) and HPV E6 requires Myc for cellular immortalization (Liu, et al., *J. Virol.* 82: 11568-11576, 2008). As shown in FIG. 12A, Y-27632 has both short term and long term effects on Myc expression in all three keratinocyte types. Myc protein levels are induced transiently immediately after culture with Y-27632 (compare p4 for HFK and P2s for HCK and HVK). After this initial induction there is a decrease in Myc expression but then a general increase over time in all three cell types. At very late passages (p107), the level of Myc is equivalent to that of an HPV31-containing cell line (FIG. 16A). The long term increase in Myc levels is similar to the increase in hTERT expression implying that increased telomerase expression might be due to Myc induction.

Figure 12B:
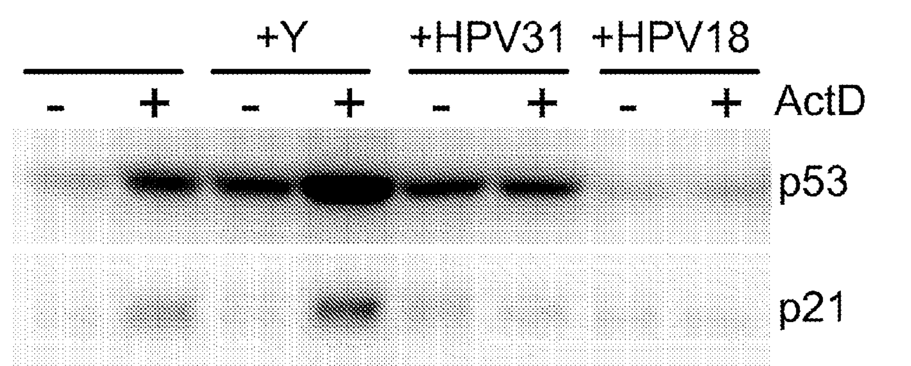
FIG. 12B is an immunoblot showing that DNA damage was induced by treatment of cells with 0.5 nM actinomycin D. The response was measured by immunoblot analysis of p53 protein levels and its downstream target p21. HFKs grown in the absence of Y-27632 were used at P4, and the Y-27632-treated HFKs were used at P122.

The Tumor Suppressor Gene p53 is Expressed in Y-27632 Immortalized Cells and can Mediate a Normal DNA Damage Response The tumor suppressor gene, p53, prevents aberrant proliferation and arrests the growth of cells that have sustained genetic damage. In most cancer-derived or immortalized cell lines the p53 pathway is either mutated or suppressed to allow cells to proliferate in conditions of aberrant growth regulation. p53 protein levels gradually increase in keratinocytes cultured with Y-27632, but this does not appear to be inhibitory to cell growth and p21 is not induced. To test whether the p53 pathway was functional in the Y-27632 immortalized cells, the response of the cells to p53-induced growth arrest mediated by DNA damage was analyzed. Normal cells exhibit growth arrest when exposed to a mutagen but this arrest is abrogated in cells immortalized by the human papillomavirus E6 and E7 oncoproteins (Foster et al., *J Virol* 68: 5698-5705, 1994). Keratinocytes were treated with 0.5 nM actinomycin D, which induces DNA strand breaks and induces a p53-mediated growth arrest (Abrams et al., *Cell Immunol.* 182: 137-151, 1997). Early passage keratinocytes and Y-27632-treated keratinocytes exhibited a normal DNA damage response; both p53 and the p53-responsive protein, p21, were upregulated (see FIG. 12B). In contrast, the HPV31 immortalized cell line CIN612, as well as HPV18 immortalized cells, did not induce p53 levels or the p53 pathway in response to the DNA damage. Therefore, Y27632 immortalized keratinocytes retain a normal DNA damage response.

Y-27632-treated Cells Retain the Ability to Differentiate

McMullan et al. (*Current Biology* 13: 2185-2189, 2003) have shown that blocking ROCK function inhibits suspension induced differentiation of human keratinocytes. To determine whether keratinocytes grown in the presence of Y-27632 retain their differentiation potential, their ability to form a stratified epithelium in organotypic raft culture was assayed. Early passage HFKs and Y-27632-treated keratinocytes were seeded onto a fibroblast-collagen matrix, and cultured as a "raft" at the liquid-air interphase for 17 days in the absence of Y-27632 in the raft media. As shown in FIG. 13 (panel a), this induces primary keratinocytes to produce a stratified epithelial tissue. Similarly, keratinocytes cultured in the presence of Y-27632 for 18 passages (FIG. 13 panel b) and late pass Y-27632 immortalized cells could also produce a stratified epithelium in organotypic culture. However, when 10 μM Y-27632 was added to the organotypic raft culture medium, no differentiation or stratification were observed (compare FIG. 13 panel c and panel d), confirming the findings of McMullan et al. in a different differentiation system.

To further demonstrate that the stratified epithelial tissue grown from Y-27632 immortalized cells expressed appropriate differentiation markers, the expression of keratin 14 (expressed in the basal layer), involucrin (upper spinous layer) and filaggrin (granular/cornified layer) was analyzed by immunofluorescence on fixed tissue sections. The results demonstrated that raft tissue grown from either untreated or Y-27632-treated cells expressed these differentiation markers in the appropriate layer (Pommerencke et al., *BMC Bioinformatics.* 9: 473, 2008). Thus, epithelial tissue generated from Y-27632 treated keratinocytes retains the ability to differentiate normally.

Example 3

Treatment of a Chronic Wound with an Organotypic Tissue Equivalent

Organotypic tissue equivalents comprised of primary keratinocytes that have been exposed to a ROCK inhibitor to increase their proliferation (and induce immortalization if cultured for a sufficient period of time) can be used to treat a subject with a chronic wound, such as a venous statis ulcer, diabetic ulcer or pressure ulcer. As described herein, primary keratinocytes are obtained from a donor. In some cases, the donor is the subject to be treated. The primary keratinocytes are obtained by skin biopsy and expanded in a monolayer culture containing an effective amount of a ROCK inhibitor, such as 10 μM Y-27632, to allow for expansion of the primary keratinocytes. The expanded primary keratinocytes are developed into an organotypic tissue equivalent by seeding onto a suitable matrix, such as a fibroblast-embedded collagen matrix and growing the cells exposed to air. After culturing for approximately, 7-14 days, the keratinocytes resemble a stratified epithelium with the characteristic epidermal structure of the human skin. The organotypic tissue equivalent is transplanted directly onto the ulcer and immobilized using a suitable bandage.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. A method of immortalizing primary keratinocytes, comprising (i) culturing the primary keratinocytes in the presence of fibroblast feeder cells and in media containing an effective amount of a ROCK inhibitor for a period of time sufficient to allow immortalization of the primary keratinocytes; and (ii) continuing to culture the immortalized keratinocytes in media lacking the ROCK inhibitor, wherein the immortalized keratinocytes retain the capacity to differentiate when cultured in media lacking ROCK inhibitor.

2. The method of claim 1, wherein continuing to culture the immortalized keratinocytes comprises culturing the immortalized keratinocytes until they form an organotypic tissue equivalent.

3. The method of claim 1, wherein the primary keratinocytes are foreskin keratinocytes, vaginal keratinocytes or cervical keratinocytes.

4. The method of claim 1, wherein the ROCK inhibitor is Y-27632.

5. The method of claim 4, wherein the effective amount of Y-27632 is about 1 to about 100 μM.

6. The method of claim 4, wherein the effective amount of Y27632 is about 5 to about 25 μM.

7. The method of claim 1, wherein the primary keratinocytes are cultured in media containing the ROCK inhibitor for at least 15 days.

8. The method of claim 4, wherein the effective amount of Y-27632 is about 10 μM.

9. The method of claim 1, wherein the ROCK inhibitor is a small molecule inhibitor.

10. The method of claim 9, wherein the effective amount of the ROCK inhibitor is about 1 to about 100 μM.

11. The method of claim 9, wherein the effective amount of the ROCK inhibitor is about 5 to about 25 μM.

12. The method of claim 9, wherein the effective amount of the ROCK inhibitor is about 10 μM.

13. The method of claim 1, wherein the ROCK inhibitor is fasudil.

14. The method of claim 1, wherein the primary keratinocytes are cultured in media containing the ROCK inhibitor for at least 20 days.

15. The method of claim 1, wherein the primary keratinocytes are cultured in media containing the ROCK inhibitor for at least 40 days.

16. The method of claim 1, wherein the primary keratinocytes are cultured in media containing the ROCK inhibitor for at least 60 days.

17. The method of claim 1, wherein the primary keratinocytes are cultured in media containing the ROCK inhibitor for at least 100 days.

* * * * *

SEQUENCE LISTING

```
<160> NUMBER OF SEQ ID NOS: 8

<210> SEQ ID NO 1
<211> LENGTH: 6650
<212> TYPE: DNA
<213> ORGANISM: Homo sapiens
<220> FEATURE:
<221> NAME/KEY: CDS
<222> LOCATION: (942)..(5006)

<400> SEQUENCE: 1

gctggttccc cttccgagcg tccgcgcccc gcatgcgcag tctgccccgg cggtctccgt      60

ttgtttgaac aggaaggcgg acatattagt ccctctcagc ccccctcgcc ccacccccca     120

ggcattcgcc gccgcgactc gccctttccc cggctgggac cgcagcccct cccagaagct     180

cccccatcag cagccgccgg gacccaacta tcgtcttcct cttcgcccgc tctccagcct     240

ttcctctgct aagtctccat cgggcatcga cctcgccctg ccccaccgga caccgtagca     300

gcagccccag cagcgacggg acaaaatggg agagtgaggc tgtcctgcgt ggaccagctc     360

gtggccgaga ctgatcggtg cgtcgggccg ggccgagtag agccggggac gcggggctag     420

accgtctaca gcgcctctga gcggagcggg cccggcccgt ggcccgagcg gcggccgcag     480

ctggcacagc tcctcacccg ccctttgctt tcgcctttcc tcttctccct cccttgttgc     540

ccggagggag tctccaccct gcttctcttt ctctacccgc tcctgcccat ctcgggacgg     600

ggacccctcc atggcgacgg cggccggggc ccgctagact gaagcacctc gccggagcga     660

cgaggctggt ggcgacggcg ctgtcggctg tcgtgagggg ctgccgggtg ggatgcgact     720

ttgggcgtcc gagcggctgt gggtcgctgt tgcccccggc ccggggtctg gagagcggag     780

gtcccctcag tgaggggaag acgggggaac cgggcgcacc tggtgaccct gaggttccgg     840

ctcctccgcc ccgcggctgc gaacccaccg cggaggaagt tggttgaaat tgctttccgc     900

tgctggtgct ggtaagaggg cattgtcaca gcagcagcaa c atg tcg act ggg gac     956
                                              Met Ser Thr Gly Asp
                                              1               5

agt ttt gag act cga ttt gaa aaa atg gac aac ctg ctg cgg gat ccc      1004
Ser Phe Glu Thr Arg Phe Glu Lys Met Asp Asn Leu Leu Arg Asp Pro
                10                  15                  20

aaa tcg gaa gtg aat tcg gat tgt ttg ctg gat gga ttg gat gct ttg      1052
Lys Ser Glu Val Asn Ser Asp Cys Leu Leu Asp Gly Leu Asp Ala Leu
            25                  30                  35

gta tat gat ttg gat ttt cct gcc tta aga aaa aac aaa aat att gac      1100
Val Tyr Asp Leu Asp Phe Pro Ala Leu Arg Lys Asn Lys Asn Ile Asp
        40                  45                  50

aac ttt tta agc aga tat aaa gac aca ata aat aaa atc aga gat tta      1148
Asn Phe Leu Ser Arg Tyr Lys Asp Thr Ile Asn Lys Ile Arg Asp Leu
    55                  60                  65

cga atg aaa gct gaa gat tat gaa gta gtg aag gtg att ggt aga ggt      1196
Arg Met Lys Ala Glu Asp Tyr Glu Val Val Lys Val Ile Gly Arg Gly
70                  75                  80                  85

gca ttt gga gaa gtt caa ttg gta agg cat aaa tcc acc agg aag gta      1244
Ala Phe Gly Glu Val Gln Leu Val Arg His Lys Ser Thr Arg Lys Val
                90                  95                  100

tat gct atg aag ctt ctc agc aaa ttt gaa atg ata aag aga tct gat      1292
Tyr Ala Met Lys Leu Leu Ser Lys Phe Glu Met Ile Lys Arg Ser Asp
```

```
            105                 110                 115

tct gct ttt ttc tgg gaa gaa agg gac atc atg gct ttt gcc aac agt     1340
Ser Ala Phe Phe Trp Glu Glu Arg Asp Ile Met Ala Phe Ala Asn Ser
        120                 125                 130

cct tgg gtt gtt cag ctt ttt tat gca ttc caa gat gat cgt tat ctc     1388
Pro Trp Val Val Gln Leu Phe Tyr Ala Phe Gln Asp Asp Arg Tyr Leu
    135                 140                 145

tac atg gtg atg gaa tac atg cct ggt gga gat ctt gta aac tta atg     1436
Tyr Met Val Met Glu Tyr Met Pro Gly Gly Asp Leu Val Asn Leu Met
150                 155                 160                 165

agc aac tat gat gtg cct gaa aaa tgg gca cga ttc tat act gca gaa     1484
Ser Asn Tyr Asp Val Pro Glu Lys Trp Ala Arg Phe Tyr Thr Ala Glu
                170                 175                 180

gta gtt ctt gca ttg gat gca atc cat tcc atg ggt ttt att cac aga     1532
Val Val Leu Ala Leu Asp Ala Ile His Ser Met Gly Phe Ile His Arg
            185                 190                 195

gat gtg aag cct gat aac atg ctg ctg gat aaa tct gga cat ttg aag     1580
Asp Val Lys Pro Asp Asn Met Leu Leu Asp Lys Ser Gly His Leu Lys
        200                 205                 210

tta gca gat ttt ggt act tgt atg aag atg aat aag gaa ggc atg gta     1628
Leu Ala Asp Phe Gly Thr Cys Met Lys Met Asn Lys Glu Gly Met Val
    215                 220                 225

cga tgt gat aca gcg gtt gga aca cct gat tat att tcc cct gaa gta     1676
Arg Cys Asp Thr Ala Val Gly Thr Pro Asp Tyr Ile Ser Pro Glu Val
230                 235                 240                 245

tta aaa tcc caa ggt ggt gat ggt tat tat gga aga gaa tgt gac tgg     1724
Leu Lys Ser Gln Gly Gly Asp Gly Tyr Tyr Gly Arg Glu Cys Asp Trp
                250                 255                 260

tgg tcg gtt ggg gta ttt tta tac gaa atg ctt gta ggt gat aca cct     1772
Trp Ser Val Gly Val Phe Leu Tyr Glu Met Leu Val Gly Asp Thr Pro
            265                 270                 275

ttt tat gca gat tct ttg gtt gga act tac agt aaa att atg aac cat     1820
Phe Tyr Ala Asp Ser Leu Val Gly Thr Tyr Ser Lys Ile Met Asn His
        280                 285                 290

aaa aat tca ctt acc ttt cct gat gat aat gac ata tca aaa gaa gca     1868
Lys Asn Ser Leu Thr Phe Pro Asp Asp Asn Asp Ile Ser Lys Glu Ala
    295                 300                 305

aaa aac ctt att tgt gcc ttc ctt act gac agg gaa gtg agg tta ggg     1916
Lys Asn Leu Ile Cys Ala Phe Leu Thr Asp Arg Glu Val Arg Leu Gly
310                 315                 320                 325

cga aat ggt gta gaa gaa atc aaa cga cat ctc ttc ttc aaa aat gac     1964
Arg Asn Gly Val Glu Glu Ile Lys Arg His Leu Phe Phe Lys Asn Asp
                330                 335                 340

cag tgg gct tgg gaa acg ctc cga gac act gta gca cca gtt gta ccc     2012
Gln Trp Ala Trp Glu Thr Leu Arg Asp Thr Val Ala Pro Val Val Pro
            345                 350                 355

gat tta agt agt gac att gat act agt aat ttt gat gac ttg gaa gaa     2060
Asp Leu Ser Ser Asp Ile Asp Thr Ser Asn Phe Asp Asp Leu Glu Glu
        360                 365                 370

gat aaa gga gag gaa gaa aca ttc cct att cct aaa gct ttc gtt ggc     2108
Asp Lys Gly Glu Glu Glu Thr Phe Pro Ile Pro Lys Ala Phe Val Gly
    375                 380                 385

aat caa cta cct ttt gta gga ttt aca tat tat agc aat cgt aga tac     2156
Asn Gln Leu Pro Phe Val Gly Phe Thr Tyr Tyr Ser Asn Arg Arg Tyr
390                 395                 400                 405

tta tct tca gca aat cct aat gat aac aga act agc tcc aat gca gat     2204
Leu Ser Ser Ala Asn Pro Asn Asp Asn Arg Thr Ser Ser Asn Ala Asp
                410                 415                 420

aaa agc ttg cag gaa agt ttg caa aaa aca atc tat aag ctg gaa gaa     2252
Lys Ser Leu Gln Glu Ser Leu Gln Lys Thr Ile Tyr Lys Leu Glu Glu
```

```
            425                 430                 435

cag ctg cat aat gaa atg cag tta aaa gat gaa atg gag cag aag tgc      2300
Gln Leu His Asn Glu Met Gln Leu Lys Asp Glu Met Glu Gln Lys Cys
        440                 445                 450

aga acc tca aac ata aaa cta gac aag ata atg aaa gaa ttg gat gaa      2348
Arg Thr Ser Asn Ile Lys Leu Asp Lys Ile Met Lys Glu Leu Asp Glu
    455                 460                 465

gag gga aat caa aga aga aat cta gaa tct aca gtg tct cag att gag      2396
Glu Gly Asn Gln Arg Arg Asn Leu Glu Ser Thr Val Ser Gln Ile Glu
470                 475                 480                 485

aag gag aaa atg ttg cta cag cat aga att aat gag tac caa aga aaa      2444
Lys Glu Lys Met Leu Leu Gln His Arg Ile Asn Glu Tyr Gln Arg Lys
                490                 495                 500

gct gaa cag gaa aat gag aag aga aga aat gta gaa aat gaa gtt tct      2492
Ala Glu Gln Glu Asn Glu Lys Arg Arg Asn Val Glu Asn Glu Val Ser
            505                 510                 515

aca tta aag gat cag ttg gaa gac tta aag aaa gtc agt cag aat tca      2540
Thr Leu Lys Asp Gln Leu Glu Asp Leu Lys Lys Val Ser Gln Asn Ser
        520                 525                 530

cag ctt gct aat gag aag ctg tcc cag tta caa aag cag cta gaa gaa      2588
Gln Leu Ala Asn Glu Lys Leu Ser Gln Leu Gln Lys Gln Leu Glu Glu
    535                 540                 545

gcc aat gac tta ctt agg aca gaa tcg gac aca gct gta aga ttg agg      2636
Ala Asn Asp Leu Leu Arg Thr Glu Ser Asp Thr Ala Val Arg Leu Arg
550                 555                 560                 565

aag agt cac aca gag atg agc aag tca att agt cag tta gag tcc ctg      2684
Lys Ser His Thr Glu Met Ser Lys Ser Ile Ser Gln Leu Glu Ser Leu
                570                 575                 580

aac aga gag ttg caa gag aga aat cga att tta gag aat tct aag tca      2732
Asn Arg Glu Leu Gln Glu Arg Asn Arg Ile Leu Glu Asn Ser Lys Ser
            585                 590                 595

caa aca gac aaa gat tat tac cag ctg caa gct ata tta gaa gct gaa      2780
Gln Thr Asp Lys Asp Tyr Tyr Gln Leu Gln Ala Ile Leu Glu Ala Glu
        600                 605                 610

cga aga gac aga ggt cat gat tct gag atg att gga gac ctt caa gct      2828
Arg Arg Asp Arg Gly His Asp Ser Glu Met Ile Gly Asp Leu Gln Ala
    615                 620                 625

cga att aca tct tta caa gag gag gtg aag cat ctc aaa cat aat ctc      2876
Arg Ile Thr Ser Leu Gln Glu Glu Val Lys His Leu Lys His Asn Leu
630                 635                 640                 645

gaa aaa gtg gaa gga gaa aga aaa gag gct caa gac atg ctt aat cac      2924
Glu Lys Val Glu Gly Glu Arg Lys Glu Ala Gln Asp Met Leu Asn His
                650                 655                 660

tca gaa aag gaa aag aat aat tta gag ata gat tta aac tac aaa ctt      2972
Ser Glu Lys Glu Lys Asn Asn Leu Glu Ile Asp Leu Asn Tyr Lys Leu
            665                 670                 675

aaa tca tta caa caa cgg tta gaa caa gag gta aat gaa cac aaa gta      3020
Lys Ser Leu Gln Gln Arg Leu Glu Gln Glu Val Asn Glu His Lys Val
        680                 685                 690

acc aaa gct cgt tta act gac aaa cat caa tct att gaa gag gca aag      3068
Thr Lys Ala Arg Leu Thr Asp Lys His Gln Ser Ile Glu Glu Ala Lys
    695                 700                 705

tct gtg gca atg tgt gag atg gaa aaa aag ctg aaa gaa gaa aga gaa      3116
Ser Val Ala Met Cys Glu Met Glu Lys Lys Leu Lys Glu Glu Arg Glu
710                 715                 720                 725

gct cga gag aag gct gaa aat cgg gtt gtt cag att gag aaa cag tgt      3164
Ala Arg Glu Lys Ala Glu Asn Arg Val Val Gln Ile Glu Lys Gln Cys
                730                 735                 740

tcc atg cta gac gtt gat ctg aag caa tct cag cag aaa cta gaa cat      3212
Ser Met Leu Asp Val Asp Leu Lys Gln Ser Gln Gln Lys Leu Glu His
```

```
            745                 750                 755

ttg act gga aat aaa gaa agg atg gag gat gaa gtt aag aat cta acc      3260
Leu Thr Gly Asn Lys Glu Arg Met Glu Asp Glu Val Lys Asn Leu Thr
        760                 765                 770

ctg caa ctg gag cag gaa tca aat aag cgg ctg ttg tta caa aat gaa      3308
Leu Gln Leu Glu Gln Glu Ser Asn Lys Arg Leu Leu Leu Gln Asn Glu
    775                 780                 785

ttg aag act caa gca ttt gag gca gac aat tta aaa ggt tta gaa aag      3356
Leu Lys Thr Gln Ala Phe Glu Ala Asp Asn Leu Lys Gly Leu Glu Lys
790                 795                 800                 805

cag atg aaa cag gaa ata aat act tta ttg gaa gca aag aga tta tta      3404
Gln Met Lys Gln Glu Ile Asn Thr Leu Leu Glu Ala Lys Arg Leu Leu
                810                 815                 820

gaa ttt gag tta gct cag ctt acg aaa cag tat aga gga aat gaa gga      3452
Glu Phe Glu Leu Ala Gln Leu Thr Lys Gln Tyr Arg Gly Asn Glu Gly
            825                 830                 835

cag atg cgg gag cta caa gat cag ctt gaa gct gag caa tat ttc tcg      3500
Gln Met Arg Glu Leu Gln Asp Gln Leu Glu Ala Glu Gln Tyr Phe Ser
        840                 845                 850

aca ctt tat aaa acc cag gta aag gaa ctt aaa gaa gaa att gaa gaa      3548
Thr Leu Tyr Lys Thr Gln Val Lys Glu Leu Lys Glu Glu Ile Glu Glu
    855                 860                 865

aaa aac aga gaa aat tta aag aaa ata cag gaa cta caa aat gaa aaa      3596
Lys Asn Arg Glu Asn Leu Lys Lys Ile Gln Glu Leu Gln Asn Glu Lys
870                 875                 880                 885

gaa act ctt gct act cag ttg gat cta gca gaa aca aaa gct gag tct      3644
Glu Thr Leu Ala Thr Gln Leu Asp Leu Ala Glu Thr Lys Ala Glu Ser
                890                 895                 900

gag cag ttg gcg cga ggc ctt ctg gaa gaa cag tat ttt gaa ttg acg      3692
Glu Gln Leu Ala Arg Gly Leu Leu Glu Glu Gln Tyr Phe Glu Leu Thr
            905                 910                 915

caa gaa agc aag aaa gct gct tca aga aat aga caa gag att aca gat      3740
Gln Glu Ser Lys Lys Ala Ala Ser Arg Asn Arg Gln Glu Ile Thr Asp
        920                 925                 930

aaa gat cac act gtt agt cgg ctt gaa gaa gca aac agc atg cta acc      3788
Lys Asp His Thr Val Ser Arg Leu Glu Glu Ala Asn Ser Met Leu Thr
    935                 940                 945

aaa gat att gaa ata tta aga aga gag aat gaa gag cta aca gag aaa      3836
Lys Asp Ile Glu Ile Leu Arg Arg Glu Asn Glu Glu Leu Thr Glu Lys
950                 955                 960                 965

atg aag aag gca gag gaa gaa tat aaa ctg gag aag gag gag gag atc      3884
Met Lys Lys Ala Glu Glu Glu Tyr Lys Leu Glu Lys Glu Glu Glu Ile
                970                 975                 980

agt aat ctt aag gct gcc ttt gaa aag aat atc aac act gaa cga acc      3932
Ser Asn Leu Lys Ala Ala Phe Glu Lys Asn Ile Asn Thr Glu Arg Thr
            985                 990                 995

ctt aaa aca  cag gct gtt aac aaa  ttg gca gaa ata atg  aat cga      3977
Leu Lys Thr  Gln Ala Val Asn Lys  Leu Ala Glu Ile Met  Asn Arg
        1000                 1005                 1010

aaa gat ttt  aaa att gat aga aag  aaa gct aat aca caa  gat ttg      4022
Lys Asp Phe  Lys Ile Asp Arg Lys  Lys Ala Asn Thr Gln  Asp Leu
        1015                 1020                 1025

aga aag aaa  gaa aag gaa aat cga  aag ctg caa ctg gaa  ctc aac      4067
Arg Lys Lys  Glu Lys Glu Asn Arg  Lys Leu Gln Leu Glu  Leu Asn
        1030                 1035                 1040

caa gaa aga  gag aaa ttc aac cag  atg gta gtg aaa cat  cag aag      4112
Gln Glu Arg  Glu Lys Phe Asn Gln  Met Val Val Lys His  Gln Lys
        1045                 1050                 1055

gaa ctg aat  gac atg caa gcg caa  ttg gta gaa gaa tgt  gca cat      4157
Glu Leu Asn  Asp Met Gln Ala Gln  Leu Val Glu Glu Cys  Ala His
```

```
        1060                1065                1070

agg aat gag  ctt cag atg cag ttg  gcc agc aaa gag agt  gat att      4202
Arg Asn Glu  Leu Gln Met Gln Leu  Ala Ser Lys Glu Ser  Asp Ile
        1075                1080                1085

gag caa ttg  cgt gct aaa ctt ttg  gac ctc tcg gat tct  aca agt      4247
Glu Gln Leu  Arg Ala Lys Leu Leu  Asp Leu Ser Asp Ser  Thr Ser
        1090                1095                1100

gtt gct agt  ttt cct agt gct gat  gaa act gat ggt aac  ctc cca      4292
Val Ala Ser  Phe Pro Ser Ala Asp  Glu Thr Asp Gly Asn  Leu Pro
        1105                1110                1115

gag tca aga  att gaa ggt tgg ctt  tca gta cca aat aga  gga aat      4337
Glu Ser Arg  Ile Glu Gly Trp Leu  Ser Val Pro Asn Arg  Gly Asn
        1120                1125                1130

atc aaa cga  tat ggc tgg aag aaa  cag tat gtt gtg gta  agc agc      4382
Ile Lys Arg  Tyr Gly Trp Lys Lys  Gln Tyr Val Val Val  Ser Ser
        1135                1140                1145

aaa aaa att  ttg ttc tat aat gac  gaa caa gat aag gag  caa tcc      4427
Lys Lys Ile  Leu Phe Tyr Asn Asp  Glu Gln Asp Lys Glu  Gln Ser
        1150                1155                1160

aat cca tct  atg gta ttg gac ata  gat aaa ctg ttt cac  gtt aga      4472
Asn Pro Ser  Met Val Leu Asp Ile  Asp Lys Leu Phe His  Val Arg
        1165                1170                1175

cct gta acc  caa gga gat gtg tat  aga gct gaa act gaa  gaa att      4517
Pro Val Thr  Gln Gly Asp Val Tyr  Arg Ala Glu Thr Glu  Glu Ile
        1180                1185                1190

cct aaa ata  ttc cag ata cta tat  gca aat gaa ggt gaa  tgt aga      4562
Pro Lys Ile  Phe Gln Ile Leu Tyr  Ala Asn Glu Gly Glu  Cys Arg
        1195                1200                1205

aaa gat gta  gag atg gaa cca gta  caa caa gct gaa aaa  act aat      4607
Lys Asp Val  Glu Met Glu Pro Val  Gln Gln Ala Glu Lys  Thr Asn
        1210                1215                1220

ttc caa aat  cac aaa ggc cat gag  ttt att cct aca ctc  tac cac      4652
Phe Gln Asn  His Lys Gly His Glu  Phe Ile Pro Thr Leu  Tyr His
        1225                1230                1235

ttt cct gcc  aat tgt gat gcc tgt  gcc aaa cct ctc tgg  cat gtt      4697
Phe Pro Ala  Asn Cys Asp Ala Cys  Ala Lys Pro Leu Trp  His Val
        1240                1245                1250

ttt aag cca  ccc cct gcc cta gag  tgt cga aga tgc cat  gtt aag      4742
Phe Lys Pro  Pro Pro Ala Leu Glu  Cys Arg Arg Cys His  Val Lys
        1255                1260                1265

tgc cac aga  gat cac tta gat aag  aaa gag gac tta att  tgt cca      4787
Cys His Arg  Asp His Leu Asp Lys  Lys Glu Asp Leu Ile  Cys Pro
        1270                1275                1280

tgt aaa gta  agt tat gat gta aca  tca gca aga gat atg  ctg ctg      4832
Cys Lys Val  Ser Tyr Asp Val Thr  Ser Ala Arg Asp Met  Leu Leu
        1285                1290                1295

tta gca tgt  tct cag gat gaa caa  aaa aaa tgg gta act  cat tta      4877
Leu Ala Cys  Ser Gln Asp Glu Gln  Lys Lys Trp Val Thr  His Leu
        1300                1305                1310

gta aag aaa  atc cct aag aat cca  cca tct ggt ttt gtt  cgt gct      4922
Val Lys Lys  Ile Pro Lys Asn Pro  Pro Ser Gly Phe Val  Arg Ala
        1315                1320                1325

tcc cct cga  acg ctt tct aca aga  tcc act gca aat cag  tct ttc      4967
Ser Pro Arg  Thr Leu Ser Thr Arg  Ser Thr Ala Asn Gln  Ser Phe
        1330                1335                1340

cgg aaa gtg  gtc aaa aat aca tct  gga aaa act agt taa ccatgtgact    5016
Arg Lys Val  Val Lys Asn Thr Ser  Gly Lys Thr Ser
        1345                1350

gagtgccctg tggaatcgtg tgggatgcta cctgataaac caggcttctt taaccatgca   5076
```

```
gagcagacag gctgtttctt tgacacaaat atcacaggct tcagggttaa gattgctgtt   5136

tttctgtcct tgctttggca caacacactg agggtttttt ttattgcggg tttgcctaca   5196

ggtagattag attaattatt actatgtaat gcaagtacag ttgggggaaa gcttaggtag   5256

atatattttt tttaaaaggt gctgcctttt tggatttata agaaaatgcc tgtcagtcgt   5316

gatagaacag agttttcctc atatgagtaa gaggaaggga ctttcacttt caagtggaac   5376

agccatcact atcaagatca gctcatggaa ggagtaaaga aaatatctca aaatgagaca   5436

aactgaagtt ttgttttttt tttaatgact taagtttttg tgctcttgca agactataca   5496

aaactatttt aagaaagcag tgatatcact tgaacttcag tgccctcact gtagaattta   5556

aaagccttac tgttgattgc ccatgttgga cttgatggag aaattaaata tctttcatta   5616

tgctttacaa aatactgtat atgtttcagc aagtttgggg aatgggagag gacaaaaaaa   5676

agttacattt aatctatgca tttttgccaa gccatattga gttattttac tactagagac   5736

attaggaaac taactgtaca aaagaaccaa gtttaaaagc attttgtggg gtacatcatt   5796

tctataattg tataatgtat ttctttgtgg ttttaaatga taaagacatt aagttaacaa   5856

acatataaga aatgtatgca ctgtttgaaa tgtaaattat tcttagaaca ctttcaatgg   5916

gggttgcatt gtccttttag tgccttaatt tgagataatt attttactgc catgagtaag   5976

tatagaaatt tcaaaaaatg tattttcaaa aaattatgtg tgtcagtgag tttttcattg   6036

ataattggtt taatttaaaa tatttagagg tttgttggac tttcataaat tgagtacaat   6096

ctttgcatca aactacctgc tacaataatg actttataaa actgcaaaaa atgtagaagg   6156

ttgcaccaac ataaaaagga aatatggcaa tacatccatg atgttttcca gttaacatag   6216

gaattaccag ataaatactg ttaaactctt gtccagtaac aagagttgat tcatatggac   6276

agtatgattt attgtttatt tttttaacca aatacctcct cagtaattta taatggcttt   6336

gcagtaatgt gtatcagata agaagcactg gaaaaccgat cgtctctagg atgatatgca   6396

tgtttcaagt ggtattgaaa gccgcactga tggatatgta ataataaaca tatctgttat   6456

taatatacta atgactctgt gctcatttaa tgagaaataa aagtaattta tggatgggta   6516

tctttaattt ttactgcaat gtgttttctc atggctgaaa tgaatggaaa acatacttca   6576

aattagtctc tgattgtata taaatgtttg tgaaattcca tggttagatt aaagtgtatt   6636

tttaaaagat aaaa                                                      6650
```

<210> SEQ ID NO 2
<211> LENGTH: 1354
<212> TYPE: PRT
<213> ORGANISM: Homo sapiens

<400> SEQUENCE: 2

```
Met Ser Thr Gly Asp Ser Phe Glu Thr Arg Phe Glu Lys Met Asp Asn
1               5                   10                  15

Leu Leu Arg Asp Pro Lys Ser Glu Val Asn Ser Asp Cys Leu Leu Asp
            20                  25                  30

Gly Leu Asp Ala Leu Val Tyr Asp Leu Asp Phe Pro Ala Leu Arg Lys
        35                  40                  45

Asn Lys Asn Ile Asp Asn Phe Leu Ser Arg Tyr Lys Asp Thr Ile Asn
    50                  55                  60

Lys Ile Arg Asp Leu Arg Met Lys Ala Glu Asp Tyr Glu Val Val Lys
65                  70                  75                  80

Val Ile Gly Arg Gly Ala Phe Gly Glu Val Gln Leu Val Arg His Lys
                85                  90                  95
```

```
Ser Thr Arg Lys Val Tyr Ala Met Lys Leu Leu Ser Lys Phe Glu Met
            100                 105                 110

Ile Lys Arg Ser Asp Ser Ala Phe Phe Trp Glu Glu Arg Asp Ile Met
        115                 120                 125

Ala Phe Ala Asn Ser Pro Trp Val Val Gln Leu Phe Tyr Ala Phe Gln
    130                 135                 140

Asp Asp Arg Tyr Leu Tyr Met Val Met Glu Tyr Met Pro Gly Gly Asp
145                 150                 155                 160

Leu Val Asn Leu Met Ser Asn Tyr Asp Val Pro Glu Lys Trp Ala Arg
                165                 170                 175

Phe Tyr Thr Ala Glu Val Val Leu Ala Leu Asp Ala Ile His Ser Met
            180                 185                 190

Gly Phe Ile His Arg Asp Val Lys Pro Asp Asn Met Leu Leu Asp Lys
        195                 200                 205

Ser Gly His Leu Lys Leu Ala Asp Phe Gly Thr Cys Met Lys Met Asn
    210                 215                 220

Lys Glu Gly Met Val Arg Cys Asp Thr Ala Val Gly Thr Pro Asp Tyr
225                 230                 235                 240

Ile Ser Pro Glu Val Leu Lys Ser Gln Gly Gly Asp Gly Tyr Tyr Gly
                245                 250                 255

Arg Glu Cys Asp Trp Trp Ser Val Gly Val Phe Leu Tyr Glu Met Leu
            260                 265                 270

Val Gly Asp Thr Pro Phe Tyr Ala Asp Ser Leu Val Gly Thr Tyr Ser
        275                 280                 285

Lys Ile Met Asn His Lys Asn Ser Leu Thr Phe Pro Asp Asp Asn Asp
    290                 295                 300

Ile Ser Lys Glu Ala Lys Asn Leu Ile Cys Ala Phe Leu Thr Asp Arg
305                 310                 315                 320

Glu Val Arg Leu Gly Arg Asn Gly Val Glu Glu Ile Lys Arg His Leu
                325                 330                 335

Phe Phe Lys Asn Asp Gln Trp Ala Trp Glu Thr Leu Arg Asp Thr Val
            340                 345                 350

Ala Pro Val Val Pro Asp Leu Ser Ser Asp Ile Asp Thr Ser Asn Phe
        355                 360                 365

Asp Asp Leu Glu Glu Asp Lys Gly Glu Glu Glu Thr Phe Pro Ile Pro
    370                 375                 380

Lys Ala Phe Val Gly Asn Gln Leu Pro Phe Val Gly Phe Thr Tyr Tyr
385                 390                 395                 400

Ser Asn Arg Arg Tyr Leu Ser Ser Ala Asn Pro Asn Asp Asn Arg Thr
                405                 410                 415

Ser Ser Asn Ala Asp Lys Ser Leu Gln Glu Ser Leu Gln Lys Thr Ile
            420                 425                 430

Tyr Lys Leu Glu Glu Gln Leu His Asn Glu Met Gln Leu Lys Asp Glu
        435                 440                 445

Met Glu Gln Lys Cys Arg Thr Ser Asn Ile Lys Leu Asp Lys Ile Met
    450                 455                 460

Lys Glu Leu Asp Glu Glu Gly Asn Gln Arg Arg Asn Leu Glu Ser Thr
465                 470                 475                 480

Val Ser Gln Ile Glu Lys Glu Lys Met Leu Leu Gln His Arg Ile Asn
                485                 490                 495

Glu Tyr Gln Arg Lys Ala Glu Gln Glu Asn Glu Lys Arg Arg Asn Val
            500                 505                 510

Glu Asn Glu Val Ser Thr Leu Lys Asp Gln Leu Glu Asp Leu Lys Lys
        515                 520                 525
```

```
Val Ser Gln Asn Ser Gln Leu Ala Asn Glu Lys Leu Ser Gln Leu Gln
    530                 535                 540

Lys Gln Leu Glu Glu Ala Asn Asp Leu Leu Arg Thr Glu Ser Asp Thr
545                 550                 555                 560

Ala Val Arg Leu Arg Lys Ser His Thr Glu Met Ser Lys Ser Ile Ser
                565                 570                 575

Gln Leu Glu Ser Leu Asn Arg Glu Leu Gln Glu Arg Asn Arg Ile Leu
            580                 585                 590

Glu Asn Ser Lys Ser Gln Thr Asp Lys Asp Tyr Tyr Gln Leu Gln Ala
        595                 600                 605

Ile Leu Glu Ala Glu Arg Arg Asp Arg Gly His Asp Ser Glu Met Ile
    610                 615                 620

Gly Asp Leu Gln Ala Arg Ile Thr Ser Leu Gln Glu Glu Val Lys His
625                 630                 635                 640

Leu Lys His Asn Leu Glu Lys Val Glu Gly Glu Arg Lys Glu Ala Gln
                645                 650                 655

Asp Met Leu Asn His Ser Glu Lys Glu Lys Asn Asn Leu Glu Ile Asp
            660                 665                 670

Leu Asn Tyr Lys Leu Lys Ser Leu Gln Gln Arg Leu Glu Gln Glu Val
        675                 680                 685

Asn Glu His Lys Val Thr Lys Ala Arg Leu Thr Asp Lys His Gln Ser
    690                 695                 700

Ile Glu Glu Ala Lys Ser Val Ala Met Cys Glu Met Glu Lys Lys Leu
705                 710                 715                 720

Lys Glu Glu Arg Glu Ala Arg Glu Lys Ala Glu Asn Arg Val Val Gln
                725                 730                 735

Ile Glu Lys Gln Cys Ser Met Leu Asp Val Asp Leu Lys Gln Ser Gln
            740                 745                 750

Gln Lys Leu Glu His Leu Thr Gly Asn Lys Glu Arg Met Glu Asp Glu
        755                 760                 765

Val Lys Asn Leu Thr Leu Gln Leu Glu Gln Glu Ser Asn Lys Arg Leu
    770                 775                 780

Leu Leu Gln Asn Glu Leu Lys Thr Gln Ala Phe Glu Ala Asp Asn Leu
785                 790                 795                 800

Lys Gly Leu Glu Lys Gln Met Lys Gln Glu Ile Asn Thr Leu Leu Glu
                805                 810                 815

Ala Lys Arg Leu Leu Glu Phe Glu Leu Ala Gln Leu Thr Lys Gln Tyr
            820                 825                 830

Arg Gly Asn Glu Gly Gln Met Arg Glu Leu Gln Asp Gln Leu Glu Ala
        835                 840                 845

Glu Gln Tyr Phe Ser Thr Leu Tyr Lys Thr Gln Val Lys Glu Leu Lys
    850                 855                 860

Glu Glu Ile Glu Glu Lys Asn Arg Glu Asn Leu Lys Lys Ile Gln Glu
865                 870                 875                 880

Leu Gln Asn Glu Lys Glu Thr Leu Ala Thr Gln Leu Asp Leu Ala Glu
                885                 890                 895

Thr Lys Ala Glu Ser Glu Gln Leu Ala Arg Gly Leu Leu Glu Glu Gln
            900                 905                 910

Tyr Phe Glu Leu Thr Gln Glu Ser Lys Lys Ala Ala Ser Arg Asn Arg
        915                 920                 925

Gln Glu Ile Thr Asp Lys Asp His Thr Val Ser Arg Leu Glu Glu Ala
    930                 935                 940

Asn Ser Met Leu Thr Lys Asp Ile Glu Ile Leu Arg Arg Glu Asn Glu
```

```
945                 950                 955                 960

Glu Leu Thr Glu Lys Met Lys Lys Ala Glu Glu Glu Tyr Lys Leu Glu
                965                 970                 975

Lys Glu Glu Glu Ile Ser Asn Leu Lys Ala Ala Phe Glu Lys Asn Ile
            980                 985                 990

Asn Thr Glu Arg Thr Leu Lys Thr  Gln Ala Val Asn Lys  Leu Ala Glu
        995                 1000                 1005

Ile Met  Asn Arg Lys Asp Phe  Lys Ile Asp Arg Lys  Lys Ala Asn
    1010                 1015                 1020

Thr Gln  Asp Leu Arg Lys Lys  Glu Lys Glu Asn Arg  Lys Leu Gln
    1025                 1030                 1035

Leu Glu  Leu Asn Gln Glu Arg  Glu Lys Phe Asn Gln  Met Val Val
    1040                 1045                 1050

Lys His  Gln Lys Glu Leu Asn  Asp Met Gln Ala Gln  Leu Val Glu
    1055                 1060                 1065

Glu Cys  Ala His Arg Asn Glu  Leu Gln Met Gln Leu  Ala Ser Lys
    1070                 1075                 1080

Glu Ser  Asp Ile Glu Gln Leu  Arg Ala Lys Leu Leu  Asp Leu Ser
    1085                 1090                 1095

Asp Ser  Thr Ser Val Ala Ser  Phe Pro Ser Ala Asp  Glu Thr Asp
    1100                 1105                 1110

Gly Asn  Leu Pro Glu Ser Arg  Ile Glu Gly Trp Leu  Ser Val Pro
    1115                 1120                 1125

Asn Arg  Gly Asn Ile Lys Arg  Tyr Gly Trp Lys Lys  Gln Tyr Val
    1130                 1135                 1140

Val Val  Ser Ser Lys Lys Ile  Leu Phe Tyr Asn Asp  Glu Gln Asp
    1145                 1150                 1155

Lys Glu  Gln Ser Asn Pro Ser  Met Val Leu Asp Ile  Asp Lys Leu
    1160                 1165                 1170

Phe His  Val Arg Pro Val Thr  Gln Gly Asp Val Tyr  Arg Ala Glu
    1175                 1180                 1185

Thr Glu  Glu Ile Pro Lys Ile  Phe Gln Ile Leu Tyr  Ala Asn Glu
    1190                 1195                 1200

Gly Glu  Cys Arg Lys Asp Val  Glu Met Glu Pro Val  Gln Gln Ala
    1205                 1210                 1215

Glu Lys  Thr Asn Phe Gln Asn  His Lys Gly His Glu  Phe Ile Pro
    1220                 1225                 1230

Thr Leu  Tyr His Phe Pro Ala  Asn Cys Asp Ala Cys  Ala Lys Pro
    1235                 1240                 1245

Leu Trp  His Val Phe Lys Pro  Pro Pro Ala Leu Glu  Cys Arg Arg
    1250                 1255                 1260

Cys His  Val Lys Cys His Arg  Asp His Leu Asp Lys  Lys Glu Asp
    1265                 1270                 1275

Leu Ile  Cys Pro Cys Lys Val  Ser Tyr Asp Val Thr  Ser Ala Arg
    1280                 1285                 1290

Asp Met  Leu Leu Leu Ala Cys  Ser Gln Asp Glu Gln  Lys Lys Trp
    1295                 1300                 1305

Val Thr  His Leu Val Lys Lys  Ile Pro Lys Asn Pro  Pro Ser Gly
    1310                 1315                 1320

Phe Val  Arg Ala Ser Pro Arg  Thr Leu Ser Thr Arg  Ser Thr Ala
    1325                 1330                 1335

Asn Gln  Ser Phe Arg Lys Val  Val Lys Asn Thr Ser  Gly Lys Thr
    1340                 1345                 1350
```

```
Ser


<210> SEQ ID NO 3
<211> LENGTH: 6401
<212> TYPE: DNA
<213> ORGANISM: Homo sapiens
<220> FEATURE:
<221> NAME/KEY: CDS
<222> LOCATION: (450)..(4616)

<400> SEQUENCE: 3

caaggcggcc ggcggcgacc atggcagcgg gccggcggcg gccgtagtgg cccaggcctg      60

ggcttcagcc tcccggggcc ccagagggcg gggcggtccg ggccgcggcg gtggcggcgc     120

cacttccctg ctcccgcccg aggactcctg cgggcactcg ctgaggacca gcggaccggc     180

ggcgcgaatc tgactgaggg gcggggacgc cgtctgttcc ccgccgctcc cggcagggcc     240

gggccgggct gggccgggct gggccgggcg ggcccctggg agcagccccc aggcggggga     300

ccgccttgga gacccgaagc cggagctaga ggcaggcggt gggcccgggt ggagtcccgg     360

ccggagctgg tggttcgggg gcggtgctag gccccgaggc tgcgggacct gagcgcgagg     420

agcctgagtg cgggtccagc ggtggcggc atg agc cgg ccc ccg ccg acg ggg       473
                                Met Ser Arg Pro Pro Pro Thr Gly
                                1               5

aaa atg ccc ggc gcc ccc gag acc gcg ccg ggg gac ggg gca ggc gcg       521
Lys Met Pro Gly Ala Pro Glu Thr Ala Pro Gly Asp Gly Ala Gly Ala
    10                  15                  20

agc cgc cag agg aag ctg gag gcg ctg atc cga gac cct cgc tcc ccc       569
Ser Arg Gln Arg Lys Leu Glu Ala Leu Ile Arg Asp Pro Arg Ser Pro
25                  30                  35                  40

atc aac gtg gag agc ttg ctg gat ggc tta aat tcc ttg gtc ctt gat       617
Ile Asn Val Glu Ser Leu Leu Asp Gly Leu Asn Ser Leu Val Leu Asp
                45                  50                  55

tta gat ttt cct gct ttg agg aaa aac aag aac ata gat aat ttc tta       665
Leu Asp Phe Pro Ala Leu Arg Lys Asn Lys Asn Ile Asp Asn Phe Leu
            60                  65                  70

aat aga tat gag aaa att gtg aaa aaa atc aga ggt cta cag atg aag       713
Asn Arg Tyr Glu Lys Ile Val Lys Lys Ile Arg Gly Leu Gln Met Lys
        75                  80                  85

gca gaa gac tat gat gtt gta aaa gtt att gga aga ggt gct ttt ggt       761
Ala Glu Asp Tyr Asp Val Val Lys Val Ile Gly Arg Gly Ala Phe Gly
    90                  95                  100

gaa gtg cag ttg gtt cgt cac aag gca tcg cag aag gtt tat gct atg       809
Glu Val Gln Leu Val Arg His Lys Ala Ser Gln Lys Val Tyr Ala Met
105                 110                 115                 120

aag ctt ctt agt aag ttt gaa atg ata aaa aga tca gat tct gcc ttt       857
Lys Leu Leu Ser Lys Phe Glu Met Ile Lys Arg Ser Asp Ser Ala Phe
                125                 130                 135

ttt tgg gaa gaa aga gat att atg gcc ttt gcc aat agc ccc tgg gtg       905
Phe Trp Glu Glu Arg Asp Ile Met Ala Phe Ala Asn Ser Pro Trp Val
            140                 145                 150

gtt cag ctt ttt tat gcc ttt caa gat gat agg tat ctg tac atg gta       953
Val Gln Leu Phe Tyr Ala Phe Gln Asp Asp Arg Tyr Leu Tyr Met Val
        155                 160                 165

atg gag tac atg cct ggt gga gac ctt gta aac ctt atg agt aat tat      1001
Met Glu Tyr Met Pro Gly Gly Asp Leu Val Asn Leu Met Ser Asn Tyr
    170                 175                 180

gat gtg cct gaa aaa tgg gcc aaa ttt tac act gct gaa gtt gtt ctt      1049
Asp Val Pro Glu Lys Trp Ala Lys Phe Tyr Thr Ala Glu Val Val Leu
185                 190                 195                 200

gct ctg gat gca ata cac tcc atg ggt tta ata cac aga gat gtg aag      1097
```

```
Ala Leu Asp Ala Ile His Ser Met Gly Leu Ile His Arg Asp Val Lys
                205                 210                 215

cct gac aac atg ctc ttg gat aaa cat gga cat cta aaa tta gca gat     1145
Pro Asp Asn Met Leu Leu Asp Lys His Gly His Leu Lys Leu Ala Asp
            220                 225                 230

ttt ggc acg tgt atg aag atg gat gaa aca ggc atg gta cat tgt gat     1193
Phe Gly Thr Cys Met Lys Met Asp Glu Thr Gly Met Val His Cys Asp
        235                 240                 245

aca gca gtt gga aca ccg gat tat ata tca cct gag gtt ctg aaa tca     1241
Thr Ala Val Gly Thr Pro Asp Tyr Ile Ser Pro Glu Val Leu Lys Ser
    250                 255                 260

caa ggg ggt gat ggt ttc tat ggg cga gaa tgt gat tgg tgg tct gta     1289
Gln Gly Gly Asp Gly Phe Tyr Gly Arg Glu Cys Asp Trp Trp Ser Val
265                 270                 275                 280

ggt gtt ttc ctt tat gag atg cta gtg ggg gat act cca ttt tat gcg     1337
Gly Val Phe Leu Tyr Glu Met Leu Val Gly Asp Thr Pro Phe Tyr Ala
                285                 290                 295

gat tca ctt gta gga aca tat agc aaa att atg gat cat aag aat tca     1385
Asp Ser Leu Val Gly Thr Tyr Ser Lys Ile Met Asp His Lys Asn Ser
            300                 305                 310

ctg tgt ttc cct gaa gat gca gaa att tcc aaa cat gca aag aat ctc     1433
Leu Cys Phe Pro Glu Asp Ala Glu Ile Ser Lys His Ala Lys Asn Leu
        315                 320                 325

atc tgt gct ttc tta aca gat agg gag gta cga ctt ggg aga aat ggg     1481
Ile Cys Ala Phe Leu Thr Asp Arg Glu Val Arg Leu Gly Arg Asn Gly
    330                 335                 340

gtg gaa gaa atc aga cag cat cct ttc ttt aag aat gat cag tgg cat     1529
Val Glu Glu Ile Arg Gln His Pro Phe Phe Lys Asn Asp Gln Trp His
345                 350                 355                 360

tgg gat aac ata aga gaa acg gca gct cct gta gta cct gaa ctc agc     1577
Trp Asp Asn Ile Arg Glu Thr Ala Ala Pro Val Val Pro Glu Leu Ser
                365                 370                 375

agt gac ata gac agc agc aat ttc gat gac att gaa gat gac aaa gga     1625
Ser Asp Ile Asp Ser Ser Asn Phe Asp Asp Ile Glu Asp Asp Lys Gly
            380                 385                 390

gat gta gaa acc ttc cca att cct aaa gct ttt gtt gga aat cag ctg     1673
Asp Val Glu Thr Phe Pro Ile Pro Lys Ala Phe Val Gly Asn Gln Leu
        395                 400                 405

cct ttc atc gga ttt acc tac tat aga gaa aat tta tta tta agt gac     1721
Pro Phe Ile Gly Phe Thr Tyr Tyr Arg Glu Asn Leu Leu Leu Ser Asp
    410                 415                 420

tct cca tct tgt aga gaa act gat tcc ata caa tca agg aaa aat gaa     1769
Ser Pro Ser Cys Arg Glu Thr Asp Ser Ile Gln Ser Arg Lys Asn Glu
425                 430                 435                 440

gaa agt caa gag att cag aaa aaa ctg tat aca tta gaa gaa cat ctt     1817
Glu Ser Gln Glu Ile Gln Lys Lys Leu Tyr Thr Leu Glu Glu His Leu
                445                 450                 455

agc aat gag atg caa gcc aaa gag gaa ctg gaa cag aag tgc aaa tct     1865
Ser Asn Glu Met Gln Ala Lys Glu Glu Leu Glu Gln Lys Cys Lys Ser
            460                 465                 470

gtt aat act cgc cta gaa aaa aca gca aag gag cta gaa gag gag att     1913
Val Asn Thr Arg Leu Glu Lys Thr Ala Lys Glu Leu Glu Glu Glu Ile
        475                 480                 485

acc tta cgg aaa agt gtg gaa tca gca tta aga cag tta gaa aga gaa     1961
Thr Leu Arg Lys Ser Val Glu Ser Ala Leu Arg Gln Leu Glu Arg Glu
    490                 495                 500

aag gcg ctt ctt cag cac aaa aat gca gaa tat cag agg aaa gct gat     2009
Lys Ala Leu Leu Gln His Lys Asn Ala Glu Tyr Gln Arg Lys Ala Asp
505                 510                 515                 520

cat gaa gca gac aaa aaa cga aat ttg gaa aat gat gtt aac agc tta     2057
```

```
His Glu Ala Asp Lys Lys Arg Asn Leu Glu Asn Asp Val Asn Ser Leu
                525                 530                 535

aaa gat caa ctt gaa gat ttg aaa aaa aga aat caa aac tct caa ata     2105
Lys Asp Gln Leu Glu Asp Leu Lys Lys Arg Asn Gln Asn Ser Gln Ile
            540                 545                 550

tcc act gag aaa gtg aat caa ctc cag aga caa ctg gat gaa acc aat     2153
Ser Thr Glu Lys Val Asn Gln Leu Gln Arg Gln Leu Asp Glu Thr Asn
        555                 560                 565

gct tta ctg cga aca gag tct gat act gca gcc cgg tta agg aaa acc     2201
Ala Leu Leu Arg Thr Glu Ser Asp Thr Ala Ala Arg Leu Arg Lys Thr
    570                 575                 580

cag gca gaa agt tca aaa cag att cag cag ctg gaa tct aac aat aga     2249
Gln Ala Glu Ser Ser Lys Gln Ile Gln Gln Leu Glu Ser Asn Asn Arg
585                 590                 595                 600

gat cta caa gat aaa aac tgc ctg ctg gag act gcc aag tta aaa ctt     2297
Asp Leu Gln Asp Lys Asn Cys Leu Leu Glu Thr Ala Lys Leu Lys Leu
                605                 610                 615

gaa aag gaa ttt atc aat ctt cag tca gct cta gaa tct gaa agg agg     2345
Glu Lys Glu Phe Ile Asn Leu Gln Ser Ala Leu Glu Ser Glu Arg Arg
            620                 625                 630

gat cga acc cat gga tca gag ata att aat gat tta caa ggt aga ata     2393
Asp Arg Thr His Gly Ser Glu Ile Ile Asn Asp Leu Gln Gly Arg Ile
        635                 640                 645

tgt ggc cta gaa gaa gat tta aag aac ggc aaa atc tta cta gcg aaa     2441
Cys Gly Leu Glu Glu Asp Leu Lys Asn Gly Lys Ile Leu Leu Ala Lys
    650                 655                 660

gta gaa ctg gag aag aga caa ctt cag gag aga ttt act gat ttg gaa     2489
Val Glu Leu Glu Lys Arg Gln Leu Gln Glu Arg Phe Thr Asp Leu Glu
665                 670                 675                 680

aag gaa aaa agc aac atg gaa ata gat atg aca tac caa cta aaa gtt     2537
Lys Glu Lys Ser Asn Met Glu Ile Asp Met Thr Tyr Gln Leu Lys Val
                685                 690                 695

ata cag cag agc cta gaa caa gaa gaa gct gaa cat aag gcc aca aag     2585
Ile Gln Gln Ser Leu Glu Gln Glu Glu Ala Glu His Lys Ala Thr Lys
            700                 705                 710

gca cga cta gca gat aaa aat aag atc tat gag tcc atc gaa gaa gcc     2633
Ala Arg Leu Ala Asp Lys Asn Lys Ile Tyr Glu Ser Ile Glu Glu Ala
        715                 720                 725

aaa tca gaa gcc atg aaa gaa atg gag aag aag ctc ttg gag gaa aga     2681
Lys Ser Glu Ala Met Lys Glu Met Glu Lys Lys Leu Leu Glu Glu Arg
    730                 735                 740

act tta aaa cag aaa gtg gag aac cta ttg cta gaa gct gag aaa aga     2729
Thr Leu Lys Gln Lys Val Glu Asn Leu Leu Leu Glu Ala Glu Lys Arg
745                 750                 755                 760

tgt tct cta tta gac tgt gac ctc aaa cag tca cag cag aaa ata aat     2777
Cys Ser Leu Leu Asp Cys Asp Leu Lys Gln Ser Gln Gln Lys Ile Asn
                765                 770                 775

gag ctc ctt aaa cag aaa gat gtg cta aat gag gat gtt aga aac ctg     2825
Glu Leu Leu Lys Gln Lys Asp Val Leu Asn Glu Asp Val Arg Asn Leu
            780                 785                 790

aca tta aaa ata gag caa gaa act cag aag cgc tgc ctt aca caa aat     2873
Thr Leu Lys Ile Glu Gln Glu Thr Gln Lys Arg Cys Leu Thr Gln Asn
        795                 800                 805

gac ctg aag atg caa aca caa cag gtt aac aca cta aaa atg tca gaa     2921
Asp Leu Lys Met Gln Thr Gln Gln Val Asn Thr Leu Lys Met Ser Glu
    810                 815                 820

aag cag tta aag caa gaa aat aac cat ctc atg gaa atg aaa atg aac     2969
Lys Gln Leu Lys Gln Glu Asn Asn His Leu Met Glu Met Lys Met Asn
825                 830                 835                 840

ttg gaa aaa caa aat gct gaa ctt cga aaa gaa cgt cag gat gca gat     3017
```

```
Leu Glu Lys Gln Asn Ala Glu Leu Arg Lys Glu Arg Gln Asp Ala Asp
                845                 850                 855

ggg caa atg aaa gag ctc cag gat cag ctc gaa gca gaa cag tat ttc      3065
Gly Gln Met Lys Glu Leu Gln Asp Gln Leu Glu Ala Glu Gln Tyr Phe
            860                 865                 870

tca acc ctt tat aaa aca caa gtt agg gag ctt aaa gaa gaa tgt gaa      3113
Ser Thr Leu Tyr Lys Thr Gln Val Arg Glu Leu Lys Glu Glu Cys Glu
        875                 880                 885

gaa aag acc aaa ctt ggt aaa gaa ttg cag cag aag aaa cag gaa tta      3161
Glu Lys Thr Lys Leu Gly Lys Glu Leu Gln Gln Lys Lys Gln Glu Leu
    890                 895                 900

cag gat gaa cgg gac tct ttg gct gcc caa ctg gag atc acc ttg acc      3209
Gln Asp Glu Arg Asp Ser Leu Ala Ala Gln Leu Glu Ile Thr Leu Thr
905                 910                 915                 920

aaa gca gat tct gag caa ctg gct cgt tca att gct gaa gaa caa tat      3257
Lys Ala Asp Ser Glu Gln Leu Ala Arg Ser Ile Ala Glu Glu Gln Tyr
                925                 930                 935

tct gat ttg gaa aaa gag aag atc atg aaa gag ctg gag atc aaa gag      3305
Ser Asp Leu Glu Lys Glu Lys Ile Met Lys Glu Leu Glu Ile Lys Glu
            940                 945                 950

atg atg gct aga cac aaa cag gaa ctt acg gaa aaa gat gct aca att      3353
Met Met Ala Arg His Lys Gln Glu Leu Thr Glu Lys Asp Ala Thr Ile
        955                 960                 965

gct tct ctt gag gaa act aat agg aca cta act agt gat gtt gcc aat      3401
Ala Ser Leu Glu Glu Thr Asn Arg Thr Leu Thr Ser Asp Val Ala Asn
    970                 975                 980

ctt gca aat gag aaa gaa gaa tta aat aac aaa ttg aaa gat gtt caa      3449
Leu Ala Asn Glu Lys Glu Glu Leu Asn Asn Lys Leu Lys Asp Val Gln
985                 990                 995                 1000

gag caa ctg tca aga  ttg aaa gat gaa gaa  ata agc gca gca gct       3494
Glu Gln Leu Ser Arg  Leu Lys Asp Glu Glu  Ile Ser Ala Ala Ala
                1005                1010                1015

att aaa gca cag ttt  gag aag cag cta tta  aca gaa aga aca ctc       3539
Ile Lys Ala Gln Phe  Glu Lys Gln Leu Leu  Thr Glu Arg Thr Leu
                1020                1025                1030

aaa act caa gct gtg  aat aag ttg gct gag  atc atg aat cga aaa       3584
Lys Thr Gln Ala Val  Asn Lys Leu Ala Glu  Ile Met Asn Arg Lys
                1035                1040                1045

gaa cct gtc aag cgt  ggt aat gac aca gat  gtg cgg aga aaa gag       3629
Glu Pro Val Lys Arg  Gly Asn Asp Thr Asp  Val Arg Arg Lys Glu
                1050                1055                1060

aag gag aat aga aag  cta cat atg gag ctt  aaa tct gaa cgt gag       3674
Lys Glu Asn Arg Lys  Leu His Met Glu Leu  Lys Ser Glu Arg Glu
                1065                1070                1075

aaa ttg acc cag cag  atg atc aag tat cag  aaa gaa ctg aat gaa       3719
Lys Leu Thr Gln Gln  Met Ile Lys Tyr Gln  Lys Glu Leu Asn Glu
                1080                1085                1090

atg cag gca caa ata  gct gaa gag agc cag  att cga att gaa ctg       3764
Met Gln Ala Gln Ile  Ala Glu Glu Ser Gln  Ile Arg Ile Glu Leu
                1095                1100                1105

cag atg aca ttg gac  agt aaa gac agt gac  att gag cag ctg cgg       3809
Gln Met Thr Leu Asp  Ser Lys Asp Ser Asp  Ile Glu Gln Leu Arg
                1110                1115                1120

tca caa ctc caa gcc  ttg cat att ggt ctg  gat agt tcc agt ata       3854
Ser Gln Leu Gln Ala  Leu His Ile Gly Leu  Asp Ser Ser Ser Ile
                1125                1130                1135

ggc agt gga cca ggg  gat gct gag gca gat  gat ggg ttt cca gaa       3899
Gly Ser Gly Pro Gly  Asp Ala Glu Ala Asp  Asp Gly Phe Pro Glu
                1140                1145                1150

tca aga tta gaa gga  tgg ctt tca ttg cct  gta cga aac aac act       3944
```

```
Ser Arg Leu Glu Gly  Trp Leu Ser Leu Pro  Val Arg Asn Asn Thr
                1155                 1160                 1165

aag aaa ttt gga tgg  gtt aaa aag tat gtg  att gta agc agt aag      3989
Lys Lys Phe Gly Trp  Val Lys Lys Tyr Val  Ile Val Ser Ser Lys
                1170                 1175                 1180

aag att ctt ttc tat  gac agt gaa caa gat  aaa gaa caa tcc aat      4034
Lys Ile Leu Phe Tyr  Asp Ser Glu Gln Asp  Lys Glu Gln Ser Asn
                1185                 1190                 1195

cct tac atg gtt tta  gat ata gac aag tta  ttt cat gtc cga cca      4079
Pro Tyr Met Val Leu  Asp Ile Asp Lys Leu  Phe His Val Arg Pro
                1200                 1205                 1210

gtt aca cag aca gat  gtg tat aga gca gat  gct aaa gaa att cca      4124
Val Thr Gln Thr Asp  Val Tyr Arg Ala Asp  Ala Lys Glu Ile Pro
                1215                 1220                 1225

agg ata ttc cag att  ctg tat gcc aat gaa  gga gaa agt aag aag      4169
Arg Ile Phe Gln Ile  Leu Tyr Ala Asn Glu  Gly Glu Ser Lys Lys
                1230                 1235                 1240

gaa caa gaa ttt cca  gtg gag cca gtt gga  gaa aaa tct aat tat      4214
Glu Gln Glu Phe Pro  Val Glu Pro Val Gly  Glu Lys Ser Asn Tyr
                1245                 1250                 1255

att tgc cac aag gga  cat gag ttt att cct  act ctt tat cat ttc      4259
Ile Cys His Lys Gly  His Glu Phe Ile Pro  Thr Leu Tyr His Phe
                1260                 1265                 1270

cca acc aac tgt gag  gct tgt atg aag ccc  ctg tgg cac atg ttt      4304
Pro Thr Asn Cys Glu  Ala Cys Met Lys Pro  Leu Trp His Met Phe
                1275                 1280                 1285

aag cct cct cct gct  ttg gag tgc cgc cgt  tgc cat att aag tgt      4349
Lys Pro Pro Pro Ala  Leu Glu Cys Arg Arg  Cys His Ile Lys Cys
                1290                 1295                 1300

cat aaa gat cat atg  gac aaa aag gag gag  att ata gca cct tgc      4394
His Lys Asp His Met  Asp Lys Lys Glu Glu  Ile Ile Ala Pro Cys
                1305                 1310                 1315

aaa gta tat tat gat  att tca acg gca aag  aat ctg tta tta cta      4439
Lys Val Tyr Tyr Asp  Ile Ser Thr Ala Lys  Asn Leu Leu Leu Leu
                1320                 1325                 1330

gca aat tct aca gaa  gag cag cag aag tgg  gtt agt cgg ttg gtg      4484
Ala Asn Ser Thr Glu  Glu Gln Gln Lys Trp  Val Ser Arg Leu Val
                1335                 1340                 1345

aaa aag ata cct aaa  aag ccc cca gct cca  gac cct ttt gcc cga      4529
Lys Lys Ile Pro Lys  Lys Pro Pro Ala Pro  Asp Pro Phe Ala Arg
                1350                 1355                 1360

tca tct cct aga act  tca atg aag ata cag  caa aac cag tct att      4574
Ser Ser Pro Arg Thr  Ser Met Lys Ile Gln  Gln Asn Gln Ser Ile
                1365                 1370                 1375

aga cgg cca agt cga  cag ctt gcc cca aac  aaa cct agc taa          4616
Arg Arg Pro Ser Arg  Gln Leu Ala Pro Asn  Lys Pro Ser
                1380                 1385

ctgccttcta tgaaagcagt cattattcaa ggtgatcgta ttcttccagt gaaaacaaga   4676

ctgaaatatg atggcccaaa atttattaaa aagctatatt ttcctgagag actgatacat   4736

acactcatac atatatgtgt tcccctttc cctgtaatat aaattacaaa tctgggctcc   4796

tttgaagcaa caggttgaac caacaatgat tggttgatag actaaggata tatgcaactc   4856

ttccagactt ttccataaag ctctctcggc agtcgctcac actacaatgc acacaaggat   4916

tgagaagagt taaaggctaa agaaaacatc ttttctagct tcaacagaga ggtttcacca   4976

gcacatttac cagaagaatc tgggaatgga ttccactaca gtgatattga ctgcatcttt   5036

aagaagtgac cattatactg tgtatatata tataaacaca cacacatata tatatatata   5096

tatagtactc taatactgca agaaggtttt ttaaacttcc cactttattt tttatacaca   5156
```

```
ttaatcagat atcattactt gctgcagttg caactatgca cttgtataaa gccataatgt   5216

tggagtttat atcactcatt cctgtgtacc tgatggaagt tgcatgttca tgtttaagca   5276

gttactgtaa caagaagttt aaagttaatt atatcagttt cctaatgctt catgataggc   5336

aactttaccc attttgaatg ccttaattta attttttca aagtctcagc cctgtctgta   5396

ttaaaaaaca aaaaaagcgt ttaccagctc ttaggatgta aactagcttt gtggaagata   5456

aatcgtgcac tatttttaca cataaatagt tatatcaatg tcagcctatt ttgattaaca   5516

aatgttttta aagtattatt ggttatagaa acaataatgg atggtgttgg aactaatata   5576

tccttgatgt ctgtctatta ttcattcaac tctttttaca gacctcagta ttagtctgtg   5636

actacaaaat attttatttg ctttaaattt gctggctacc ctagatgtgt ttttattcct   5696

ggtaaagaca tttgtgatta cattttcaca cttaagattc aaaatttttc ccaaatataa   5756

agaaaactaa gacagactgt agatgcattt taaatattta aatatgatcc tcagacatgc   5816

agctgtgtgt ggcagtattt tagtaccggg ttaagaaaac tggcaactgg gaagaagtgg   5876

cctcaaaggc acttaatttg atttttattt tttaaatgct gtcaaagtta cagtttacgc   5936

aggacattct tgccgtattc tcatgatccc agataagtgt gtgttttata ctgcaacaat   5996

atgcagcaat ggtaagcgta aagttttttt tttgttttttg tttttttta tattatgaag   6056

tcttttaaca gtctctcttt atataaatac acagagtttg gtatgatatt taaatacatc   6116

atctggccag gcatggtggc ttacgcctgt aatcctagca ctttgggagg ccaagacggg   6176

cggatcacct gaggtgagga gttcaagacc agcctgccca acatagtgaa actccgtctc   6236

taccaatata caaaaaattag ccgggcatga tggtggtggc ctgtaatccc agctacttgg   6296

gaggctgaga caggagaatc gcttgaaccc aggagacggt ggttgcagtg agcgaagatc   6356

gagccactgc actccagcct gggcagctga acaagactcc gtctc                   6401
```

```
<210> SEQ ID NO 4
<211> LENGTH: 1388
<212> TYPE: PRT
<213> ORGANISM: Homo sapiens

<400> SEQUENCE: 4

Met Ser Arg Pro Pro Pro Thr Gly Lys Met Pro Gly Ala Pro Glu Thr
1               5                   10                  15

Ala Pro Gly Asp Gly Ala Gly Ala Ser Arg Gln Arg Lys Leu Glu Ala
            20                  25                  30

Leu Ile Arg Asp Pro Arg Ser Pro Ile Asn Val Glu Ser Leu Leu Asp
        35                  40                  45

Gly Leu Asn Ser Leu Val Leu Asp Leu Asp Phe Pro Ala Leu Arg Lys
    50                  55                  60

Asn Lys Asn Ile Asp Asn Phe Leu Asn Arg Tyr Glu Lys Ile Val Lys
65                  70                  75                  80

Lys Ile Arg Gly Leu Gln Met Lys Ala Glu Asp Tyr Asp Val Val Lys
                85                  90                  95

Val Ile Gly Arg Gly Ala Phe Gly Glu Val Gln Leu Val Arg His Lys
            100                 105                 110

Ala Ser Gln Lys Val Tyr Ala Met Lys Leu Leu Ser Lys Phe Glu Met
        115                 120                 125

Ile Lys Arg Ser Asp Ser Ala Phe Phe Trp Glu Glu Arg Asp Ile Met
    130                 135                 140

Ala Phe Ala Asn Ser Pro Trp Val Val Gln Leu Phe Tyr Ala Phe Gln
145                 150                 155                 160
```

```
Asp Asp Arg Tyr Leu Tyr Met Val Met Glu Tyr Met Pro Gly Gly Asp
                165                 170                 175

Leu Val Asn Leu Met Ser Asn Tyr Asp Val Pro Glu Lys Trp Ala Lys
            180                 185                 190

Phe Tyr Thr Ala Glu Val Val Leu Ala Leu Asp Ala Ile His Ser Met
        195                 200                 205

Gly Leu Ile His Arg Asp Val Lys Pro Asp Asn Met Leu Leu Asp Lys
    210                 215                 220

His Gly His Leu Lys Leu Ala Asp Phe Gly Thr Cys Met Lys Met Asp
225                 230                 235                 240

Glu Thr Gly Met Val His Cys Asp Thr Ala Val Gly Thr Pro Asp Tyr
                245                 250                 255

Ile Ser Pro Glu Val Leu Lys Ser Gln Gly Gly Asp Gly Phe Tyr Gly
            260                 265                 270

Arg Glu Cys Asp Trp Trp Ser Val Gly Val Phe Leu Tyr Glu Met Leu
        275                 280                 285

Val Gly Asp Thr Pro Phe Tyr Ala Asp Ser Leu Val Gly Thr Tyr Ser
    290                 295                 300

Lys Ile Met Asp His Lys Asn Ser Leu Cys Phe Pro Glu Asp Ala Glu
305                 310                 315                 320

Ile Ser Lys His Ala Lys Asn Leu Ile Cys Ala Phe Leu Thr Asp Arg
                325                 330                 335

Glu Val Arg Leu Gly Arg Asn Gly Val Glu Glu Ile Arg Gln His Pro
            340                 345                 350

Phe Phe Lys Asn Asp Gln Trp His Trp Asp Asn Ile Arg Glu Thr Ala
        355                 360                 365

Ala Pro Val Val Pro Glu Leu Ser Ser Asp Ile Asp Ser Ser Asn Phe
    370                 375                 380

Asp Asp Ile Glu Asp Asp Lys Gly Asp Val Glu Thr Phe Pro Ile Pro
385                 390                 395                 400

Lys Ala Phe Val Gly Asn Gln Leu Pro Phe Ile Gly Phe Thr Tyr Tyr
                405                 410                 415

Arg Glu Asn Leu Leu Leu Ser Asp Ser Pro Ser Cys Arg Glu Thr Asp
            420                 425                 430

Ser Ile Gln Ser Arg Lys Asn Glu Glu Ser Gln Glu Ile Gln Lys Lys
        435                 440                 445

Leu Tyr Thr Leu Glu Glu His Leu Ser Asn Glu Met Gln Ala Lys Glu
    450                 455                 460

Glu Leu Glu Gln Lys Cys Lys Ser Val Asn Thr Arg Leu Glu Lys Thr
465                 470                 475                 480

Ala Lys Glu Leu Glu Glu Glu Ile Thr Leu Arg Lys Ser Val Glu Ser
                485                 490                 495

Ala Leu Arg Gln Leu Glu Arg Glu Lys Ala Leu Leu Gln His Lys Asn
            500                 505                 510

Ala Glu Tyr Gln Arg Lys Ala Asp His Glu Ala Asp Lys Lys Arg Asn
        515                 520                 525

Leu Glu Asn Asp Val Asn Ser Leu Lys Asp Gln Leu Glu Asp Leu Lys
    530                 535                 540

Lys Arg Asn Gln Asn Ser Gln Ile Ser Thr Glu Lys Val Asn Gln Leu
545                 550                 555                 560

Gln Arg Gln Leu Asp Glu Thr Asn Ala Leu Leu Arg Thr Glu Ser Asp
                565                 570                 575

Thr Ala Ala Arg Leu Arg Lys Thr Gln Ala Glu Ser Ser Lys Gln Ile
```

```
            580                 585                 590

Gln Gln Leu Glu Ser Asn Asn Arg Asp Leu Gln Asp Lys Asn Cys Leu
        595                 600                 605

Leu Glu Thr Ala Lys Leu Lys Leu Glu Lys Glu Phe Ile Asn Leu Gln
    610                 615                 620

Ser Ala Leu Glu Ser Glu Arg Arg Asp Arg Thr His Gly Ser Glu Ile
625                 630                 635                 640

Ile Asn Asp Leu Gln Gly Arg Ile Cys Gly Leu Glu Glu Asp Leu Lys
                645                 650                 655

Asn Gly Lys Ile Leu Leu Ala Lys Val Glu Leu Glu Lys Arg Gln Leu
            660                 665                 670

Gln Glu Arg Phe Thr Asp Leu Glu Lys Glu Lys Ser Asn Met Glu Ile
        675                 680                 685

Asp Met Thr Tyr Gln Leu Lys Val Ile Gln Gln Ser Leu Glu Gln Glu
    690                 695                 700

Glu Ala Glu His Lys Ala Thr Lys Ala Arg Leu Ala Asp Lys Asn Lys
705                 710                 715                 720

Ile Tyr Glu Ser Ile Glu Glu Ala Lys Ser Glu Ala Met Lys Glu Met
                725                 730                 735

Glu Lys Lys Leu Leu Glu Glu Arg Thr Leu Lys Gln Lys Val Glu Asn
            740                 745                 750

Leu Leu Leu Glu Ala Glu Lys Arg Cys Ser Leu Leu Asp Cys Asp Leu
        755                 760                 765

Lys Gln Ser Gln Gln Lys Ile Asn Glu Leu Leu Lys Gln Lys Asp Val
    770                 775                 780

Leu Asn Glu Asp Val Arg Asn Leu Thr Leu Lys Ile Glu Gln Glu Thr
785                 790                 795                 800

Gln Lys Arg Cys Leu Thr Gln Asn Asp Leu Lys Met Gln Thr Gln Gln
                805                 810                 815

Val Asn Thr Leu Lys Met Ser Glu Lys Gln Leu Lys Gln Glu Asn Asn
            820                 825                 830

His Leu Met Glu Met Lys Met Asn Leu Glu Lys Gln Asn Ala Glu Leu
        835                 840                 845

Arg Lys Glu Arg Gln Asp Ala Asp Gly Gln Met Lys Glu Leu Gln Asp
    850                 855                 860

Gln Leu Glu Ala Glu Gln Tyr Phe Ser Thr Leu Tyr Lys Thr Gln Val
865                 870                 875                 880

Arg Glu Leu Lys Glu Glu Cys Glu Glu Lys Thr Lys Leu Gly Lys Glu
                885                 890                 895

Leu Gln Gln Lys Lys Gln Glu Leu Gln Asp Glu Arg Asp Ser Leu Ala
            900                 905                 910

Ala Gln Leu Glu Ile Thr Leu Thr Lys Ala Asp Ser Glu Gln Leu Ala
        915                 920                 925

Arg Ser Ile Ala Glu Glu Gln Tyr Ser Asp Leu Glu Lys Glu Lys Ile
    930                 935                 940

Met Lys Glu Leu Glu Ile Lys Glu Met Met Ala Arg His Lys Gln Glu
945                 950                 955                 960

Leu Thr Glu Lys Asp Ala Thr Ile Ala Ser Leu Glu Glu Thr Asn Arg
                965                 970                 975

Thr Leu Thr Ser Asp Val Ala Asn Leu Ala Asn Glu Lys Glu Glu Leu
            980                 985                 990

Asn Asn Lys Leu Lys Asp Val Gln  Glu Gln Leu Ser Arg  Leu Lys Asp
        995                 1000                1005
```

```
Glu Glu  Ile Ser Ala Ala Ala  Ile Lys Ala Gln Phe  Glu Lys Gln
    1010                 1015                 1020

Leu Leu  Thr Glu Arg Thr Leu  Lys Thr Gln Ala Val  Asn Lys Leu
    1025                 1030                 1035

Ala Glu  Ile Met Asn Arg Lys  Glu Pro Val Lys Arg  Gly Asn Asp
    1040                 1045                 1050

Thr Asp  Val Arg Arg Lys Glu  Lys Glu Asn Arg Lys  Leu His Met
    1055                 1060                 1065

Glu Leu  Lys Ser Glu Arg Glu  Lys Leu Thr Gln Gln  Met Ile Lys
    1070                 1075                 1080

Tyr Gln  Lys Glu Leu Asn Glu  Met Gln Ala Gln Ile  Ala Glu Glu
    1085                 1090                 1095

Ser Gln  Ile Arg Ile Glu Leu  Gln Met Thr Leu Asp  Ser Lys Asp
    1100                 1105                 1110

Ser Asp  Ile Glu Gln Leu Arg  Ser Gln Leu Gln Ala  Leu His Ile
    1115                 1120                 1125

Gly Leu  Asp Ser Ser Ser Ile  Gly Ser Gly Pro Gly  Asp Ala Glu
    1130                 1135                 1140

Ala Asp  Asp Gly Phe Pro Glu  Ser Arg Leu Glu Gly  Trp Leu Ser
    1145                 1150                 1155

Leu Pro  Val Arg Asn Asn Thr  Lys Lys Phe Gly Trp  Val Lys Lys
    1160                 1165                 1170

Tyr Val  Ile Val Ser Ser Lys  Lys Ile Leu Phe Tyr  Asp Ser Glu
    1175                 1180                 1185

Gln Asp  Lys Glu Gln Ser Asn  Pro Tyr Met Val Leu  Asp Ile Asp
    1190                 1195                 1200

Lys Leu  Phe His Val Arg Pro  Val Thr Gln Thr Asp  Val Tyr Arg
    1205                 1210                 1215

Ala Asp  Ala Lys Glu Ile Pro  Arg Ile Phe Gln Ile  Leu Tyr Ala
    1220                 1225                 1230

Asn Glu  Gly Glu Ser Lys Lys  Glu Gln Glu Phe Pro  Val Glu Pro
    1235                 1240                 1245

Val Gly  Glu Lys Ser Asn Tyr  Ile Cys His Lys Gly  His Glu Phe
    1250                 1255                 1260

Ile Pro  Thr Leu Tyr His Phe  Pro Thr Asn Cys Glu  Ala Cys Met
    1265                 1270                 1275

Lys Pro  Leu Trp His Met Phe  Lys Pro Pro Pro Ala  Leu Glu Cys
    1280                 1285                 1290

Arg Arg  Cys His Ile Lys Cys  His Lys Asp His Met  Asp Lys Lys
    1295                 1300                 1305

Glu Glu  Ile Ile Ala Pro Cys  Lys Val Tyr Tyr Asp  Ile Ser Thr
    1310                 1315                 1320

Ala Lys  Asn Leu Leu Leu Leu  Ala Asn Ser Thr Glu  Glu Gln Gln
    1325                 1330                 1335

Lys Trp  Val Ser Arg Leu Val  Lys Lys Ile Pro Lys  Lys Pro Pro
    1340                 1345                 1350

Ala Pro  Asp Pro Phe Ala Arg  Ser Ser Pro Arg Thr  Ser Met Lys
    1355                 1360                 1365

Ile Gln  Gln Asn Gln Ser Ile  Arg Arg Pro Ser Arg  Gln Leu Ala
    1370                 1375                 1380

Pro Asn  Lys Pro Ser
    1385
```

<210> SEQ ID NO 5

-continued

<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
cggtttgttt gggtttgggt ttgggtttgg gtttgggtt 39

<210> SEQ ID NO 6
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 6
ggcttgcctt acccttaccc ttacccttac ccttaccct 39

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tgtgctggcc catcactttg 20

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
accagccacc actttctgat agg 23